United States Patent
Matsuo et al.

(10) Patent No.: US 11,667,754 B2
(45) Date of Patent: Jun. 6, 2023

(54) TETRACARBOXYLIC DIANHYDRIDE, CARBONYL COMPOUND, POLYIMIDE PRECURSOR RESIN, AND POLYIMIDE

(71) Applicant: JXTG NIPPON OIL & ENERGY CORPORATION, Tokyo (JP)

(72) Inventors: Yusuke Matsuo, Tokyo (JP); Daisuke Watanabe, Tokyo (JP); Takahiro Hasegawa, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 835 days.

(21) Appl. No.: 16/484,886

(22) PCT Filed: Feb. 8, 2018

(86) PCT No.: PCT/JP2018/004410
§ 371 (c)(1),
(2) Date: Aug. 9, 2019

(87) PCT Pub. No.: WO2018/147373
PCT Pub. Date: Aug. 16, 2018

(65) Prior Publication Data
US 2020/0024397 A1    Jan. 23, 2020

(30) Foreign Application Priority Data
Feb. 13, 2017 (JP) .............................. JP2017-024143

(51) Int. Cl.
*C07D 307/93* (2006.01)
*C09D 179/08* (2006.01)
*C08G 73/10* (2006.01)
*C07C 69/753* (2006.01)

(52) U.S. Cl.
CPC ............ *C08G 73/10* (2013.01); *C07C 69/753* (2013.01); *C07D 307/93* (2013.01)

(58) Field of Classification Search
CPC .... C07D 307/93; C09D 179/08; C08G 73/10; C08G 73/1042; C08G 73/105; C08G 73/1078
See application file for complete search history.

(56) References Cited

U.S. PATENT DOCUMENTS

| 2013/0079490 A1 | 3/2013 | Matsumoto et al. |
| 2014/0224318 A1 | 8/2014 | Komatsu et al. |

FOREIGN PATENT DOCUMENTS

| JP | H11-60732 A | 3/1999 |
| JP | 2017-66354 A | 4/2017 |
| JP | 2017-80901 A | 5/2017 |
| JP | 2017-115163 A | 6/2017 |
| JP | 2017-115164 A | 6/2017 |
| WO | 2011/099518 A1 | 8/2011 |
| WO | 2013/021942 A1 | 2/2013 |
| WO | 2017/030019 A1 | 2/2017 |
| WO | WO-2017030019 A1 * | 2/2017 ........... C07C 69/753 |

OTHER PUBLICATIONS

English translation of the claims of WIPO Publication 2017030019-A1 (Year: 2022).*
English translation of the description of WIPO Publication 2017030019-A1 (Year: 2022).*
Apr. 17, 2018 International Search Report issued in International Patent Application No. PCT/JP2018/004410.
Sep. 14, 2022 Office Action issued in Chinese Application No. 201880006006.6.

* cited by examiner

*Primary Examiner* — Joseph R Kosack
*Assistant Examiner* — Sagar Patel
(74) *Attorney, Agent, or Firm* — Oliff PLC

(57) ABSTRACT

A tetracarboxylic dianhydride includes: at least one acid dianhydride (A) selected from the group consisting of compounds each having an endo/exo type three-dimensional structure represented by a particular general formula and their enantiomeric compounds each having an exo/endo type three-dimensional structure; and/or an acid dianhydride (B) having an endo/endo type three-dimensional structure represented by a particular general formula, wherein a content of the acid dianhydride (B) in a total amount of the acid dianhydrides (A) and (B) is 30 to 100% by mole in a mole ratio.

1 Claim, 11 Drawing Sheets

TETRACARBOXYLIC DIANHYDRIDE, CARBONYL COMPOUND, POLYIMIDE PRECURSOR RESIN, AND POLYIMIDE

TECHNICAL FIELD

The present invention relates to a tetracarboxylic dianhydride, a carbonyl compound, a polyimide precursor resin, and a polyimide.

BACKGROUND ART

In general, tetracarboxylic dianhydrides are useful as raw materials for producing polyimide resins, as epoxy curing agents, and as the like. Of the tetracarboxylic dianhydrides, aromatic tetracarboxylic dianhydrides such as pyromellitic dianhydride have been mainly used as raw materials for polyimide resins used in the field of electronic devices or the like. Then, among polyimides obtained by using such aromatic tetracarboxylic dianhydrides, for example, a polyimide (trade name: "Kapton") marketed by DU PONT-TORAY CO., LTD. has been conventionally widely known as a material necessary for cutting-edge industries for aerospace, aviation, and other applications. Conventional polyimides obtained by using aromatic tetracarboxylic dianhydrides have excellent physical properties in terms of heat resistance; however, such polyimides are colored (yellow to brown), and cannot be used in the optical and other applications where transparency is necessary.

Under such circumstances, in order to produce a polyimide which can be used in optical and other applications, research has been conducted on various tetracarboxylic dianhydrides. In recent years, tetracarboxylic dianhydrides have been reported which make it possible to produce polyimides having a sufficiently high light transmittance and also having a sufficiently high heat resistance. For example, International Publication No. WO2011/099518 (PTL 1) discloses a norbornane-2-spiro-α-cycloalkanone-α'-spiro-2"-norbornane-5,5",6,6"-tetracarboxylic dianhydride having a specific structure.

CITATION LIST

Patent Literature

[PTL 1] International Publication No. WO2011/099518

SUMMARY OF INVENTION

Technical Problem

The tetracarboxylic dianhydride as described in PTL 1 above can be used for producing polyimides having a sufficiently highlight transmittance and a sufficiently high heat resistance. However, some of applications and the like of such polyimides require further enhancement of heat resistance while sufficiently maintaining an optical characteristic (light transmittance). For this reason, in the field of polyimides, there is a demand for the advent of an polyimide which can maintain a sufficient optical characteristic (light transmittance) while achieving an even high heat resistance, as compared with polyimides which can be obtained by using the tetracarboxylic dianhydride described in PTL 1 above, and which have a sufficiently high light transmittance and a sufficiently high heat resistance.

The present invention has been made in view of the above-described problems of the conventional techniques, and an object thereof is to provide a tetracarboxylic dianhydride which is usable as a raw material monomer for producing a polyimide having a sufficient light transmittance and a heat resistance at a higher level, a carbonyl compound which can be used for efficiently producing the tetracarboxylic dianhydride, a polyimide which can have a sufficient light transmittance and a heat resistance at a higher level, and a polyimide precursor resin which can be preferably utilized for producing the polyimide.

Solution to Problem

The present inventors have conducted intensive study to achieve the above-described objects, and consequently have found that, first, use of a tetracarboxylic dianhydride represented by the following general formula (A):

[Chem. 1]

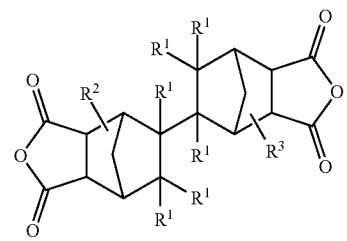

(A)

makes it possible to produce a polyimide having a sufficient light transmittance and a heat resistance at a higher level (note that $R^1$s, $R^2$, and $R^3$ in the formula (A) have the same meanings as those of $R^1$s, $R^2$, and $R^3$ in the general formula (1) to be described later, respectively, and their explanation is omitted here). Based on such knowledge, the present inventors have conducted further study on the tetracarboxylic dianhydrides represented by the general formula (A), and have found that the tetracarboxylic dianhydrides include: at least one stereoisomer A (acid dianhydride (A) to be described later) selected from the group consisting of stereoisomers A1 each having an endo/exo type structure and their enantiomeric stereoisomers A2 each having an exo/endo type structure; and a stereoisomer B (acid dianhydride (B) to be described later) having an endo/endo type structure (note that, regarding the acid dianhydrides, the "endo/exo type" structure and the "exo/endo type" structure cannot be distinguished spectroscopically, and thus the present specification expresses acid dianhydrides having those structures collectively as "acid dianhydrides (A)"). Then, the present inventors have conducted further study and have found that it is possible to surely obtain a polyimide which has a sufficient light transmittance and a heat resistance at a higher level, as compared with conventional polyimides (for example, the polyimide as described in PTL 1 above) and which further achieves one of the highest mechanical strengths among polyimides obtained by using the tetracarboxylic dianhydride represented by the general formula (A) when the polyimide is produced by using: a tetracarboxylic dianhydride comprising: at least one acid dianhydride (A) selected from the group consisting of compounds each having an endo/exo type three-dimensional structure represented by the following general formula (1) and their enantiomeric compounds each having an exo/endo type three-dimensional structure; and/or an acid dianhydride (B) having an endo/endo type three-dimensional structure represented by the following general formula (2), wherein a content of the acid dianhydride (B) in a total amount of the acid dianhydrides (A) and (B) is 30 to 100% by mole in a mole ratio. This finding has led to the completion of the present invention.

Specifically, a tetracarboxylic dianhydride of the present invention comprises at least one acid dianhydride (A) selected from the group consisting of compounds each having an endo/exo type three-dimensional structure represented by the following general formula (1):

[Chem. 2]

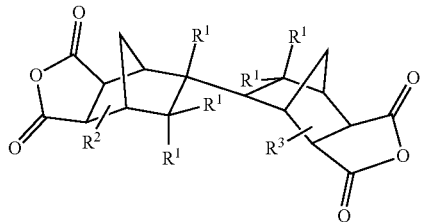

(1)

[in the formula (1), $R^1$s each independently represent one selected from the group consisting of a hydrogen atom, alkyl groups having 1 to 10 carbon atoms, a hydroxy group, and a nitro group, or two $R^1$s connected to a common carbon atom may together form a methylidene group, and $R^2$ and $R^3$ each independently represent one selected from the group consisting of a hydrogen atom and alkyl groups having 1 to 10 carbon atoms] and their enantiomeric compounds each having an exo/endo type three-dimensional structure, and/or an acid dianhydride (B) having an endo/endo type three-dimensional structure represented by the following general formula (2):

[Chem. 3]

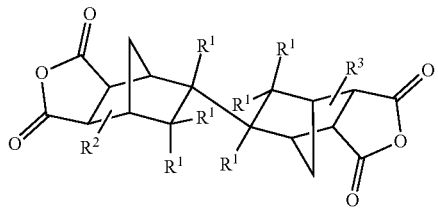

(2)

[in the formula (2), $R^1$s, $R^2$, and $R^3$ have the same meanings as those of $R^1$s, $R^2$, and $R^3$ in the above formula (1), respectively], wherein a content of the acid dianhydride (B) in a total amount of the acid dianhydrides (A) and (B) is 30 to 100% by mole in a mole ratio.

In addition, a carbonyl compound of the present invention comprises at least one carbonyl compound (A) selected from the group consisting of compounds each having an endo/exo type three-dimensional structure represented by the following general formula (3):

[Chem. 4]

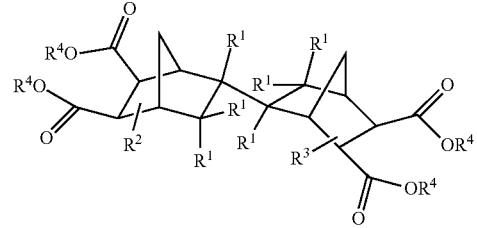

(3)

[in the formula (3), $R^1$s each independently represent one selected from the group consisting of a hydrogen atom, alkyl groups having 1 to 10 carbon atoms, a hydroxy group, and a nitro group, or two $R^1$s connected to a common carbon atom may together form a methylidene group, $R^2$ and $R^3$ each independently represent one selected from the group consisting of a hydrogen atom and alkyl groups having 1 to 10 carbon atoms, and $R^4$s each independently represent one selected from the group consisting of a hydrogen atom, alkyl groups having 1 to 10 carbon atoms, cycloalkyl groups having 3 to 10 carbon atoms, alkenyl groups having 2 to 10 carbon atoms, aryl groups having 6 to 20 carbon atoms, and aralkyl groups having 7 to 20 carbon atoms] and their enantiomeric compounds each having an exo/endo type three-dimensional structure, and/or carbonyl compound (B) having an endo/endo type three-dimensional structure represented by the following general formula (4):

[Chem. 5]

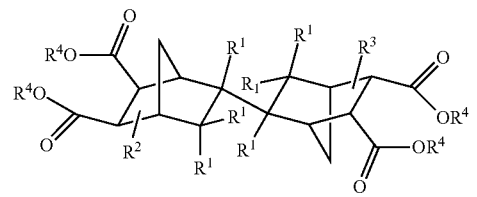

(4)

[in the formula (4), $R^1$s, $R^2$, $R^3$, and $R^4$s have the same meanings as those of $R^1$s, $R^2$, $R^3$, and $R^4$s in the above formula (3), respectively], wherein a content of the carbonyl compound (B) in a total amount of the carbonyl compounds (A) and (B) is 30 to 100% by mole in a mole ratio.

In addition, a polyimide of the present invention comprises at least one repeating unit (A) selected from the group consisting of structural units each having an endo/exo type three-dimensional structure represented by the following general formula (5):

[Chem. 6]

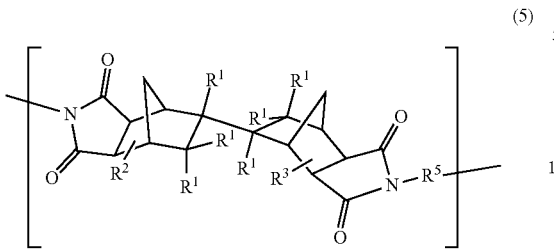

(5)

[in the formula (5), $R^1$s each independently represent one selected from the group consisting of a hydrogen atom, alkyl groups having 1 to 10 carbon atoms, a hydroxy group, and a nitro group, or two $R^1$s connected to a common carbon atom may together form a methylidene group, $R^2$ and $R^3$ each independently represent one selected from the group consisting of a hydrogen atom and alkyl groups having 1 to 10 carbon atoms, and $R^5$ represents an arylene group having 6 to 40 carbon atoms] and their enantiomeric structural units each having an exo/endo type three-dimensional structure, and/or a repeating unit (B) having an endo/endo type three-dimensional structure represented by the following general formula (6):

[Chem. 7]

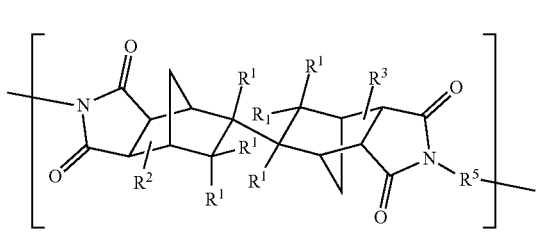

(6)

[in the formula (6), $R^1$s, $R^2$, $R^3$, and $R^5$ have the same meanings as those of $R^1$s, $R^2$, $R^3$, and $R^5$ in the above formula (5), respectively], wherein a content of the repeating unit (B) in a total amount of the repeating units (A) and (B) is 30 to 100% by mole in a mole ratio.

A polyimide precursor resin of the present invention comprises at least one repeating unit (A') selected from the group consisting of structural units each having an endo/exo type three-dimensional structure represented by the following general formula (7):

[Chem. 8]

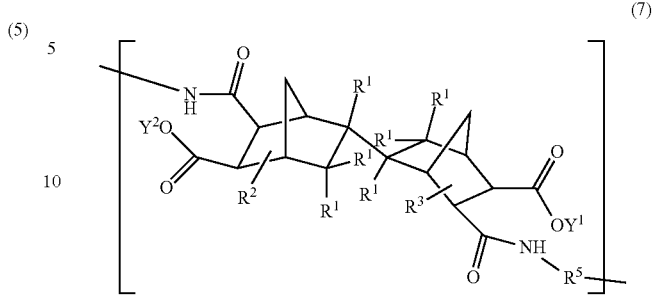

(7)

[in the formula (7), $R^1$s each independently represent one selected from the group consisting of a hydrogen atom, alkyl groups having 1 to 10 carbon atoms, a hydroxy group, and a nitro group, or two $R^1$s connected to a common carbon atom may together form a methylidene group, $R^2$ and $R^3$ each independently represent one selected from the group consisting of a hydrogen atom and alkyl groups having 1 to 10 carbon atoms, $R^5$ represents an arylene group having 6 to 40 carbon atoms, and $Y^1$ and $Y^2$ each independently represent one selected from the group consisting of a hydrogen atom, alkyl groups having 1 to 6 carbon atoms, and alkylsilyl groups having 3 to 9 carbon atoms] and their enantiomeric structural units each having an exo/endo type three-dimensional structure, and/or a repeating unit (B') having an endo/endo type three-dimensional structure represented by the following general formula (8):

[Chem. 9]

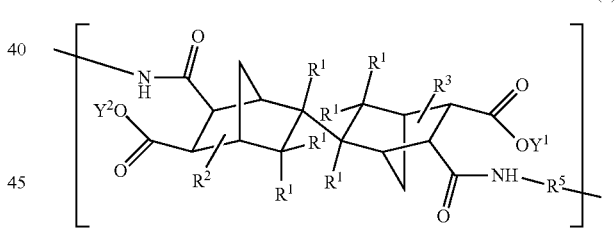

(8)

[in the formula (8), $R^1$s, $R^2$, $R^3$, $R^5$, $Y^1$, and $Y^2$ have the same meanings as those of $R^1$s, $R^2$, $R^3$, $R^5$, $Y^1$, and $Y^2$ in the above formula (7), respectively], wherein a content of the repeating unit (B') in a total amount of the repeating units (A') and (B') is 30 to 100% by mole in a mole ratio.

Note that, regarding the expression of the types of isomers and the like in the present application, the type expression is classified by focusing on one bicyclic ring (norbornane ring) and then checking whether the other bicyclic ring (norbornane ring) is bonded in exo position or endo position. For example, the above acid dianhydride (B) is expressed as the "endo/endo type" because, when seen from the left side or the right side, the endo position of one bicyclic ring is bonded with the other bicyclic ring.

Advantageous Effects of Invention

The present invention makes it possible to provide a tetracarboxylic dianhydride which is usable as a raw material monomer for producing a polyimide having a sufficient light transmittance and a heat resistance at a higher level, a carbonyl compound which can be used for efficiently producing the tetracarboxylic dianhydride, a polyimide which can have a sufficient light transmittance and a heat resistance at a higher level, and polyimide precursor resin which can be preferably utilized for producing the polyimide.

DESCRIPTION OF EMBODIMENTS

Figure 1:
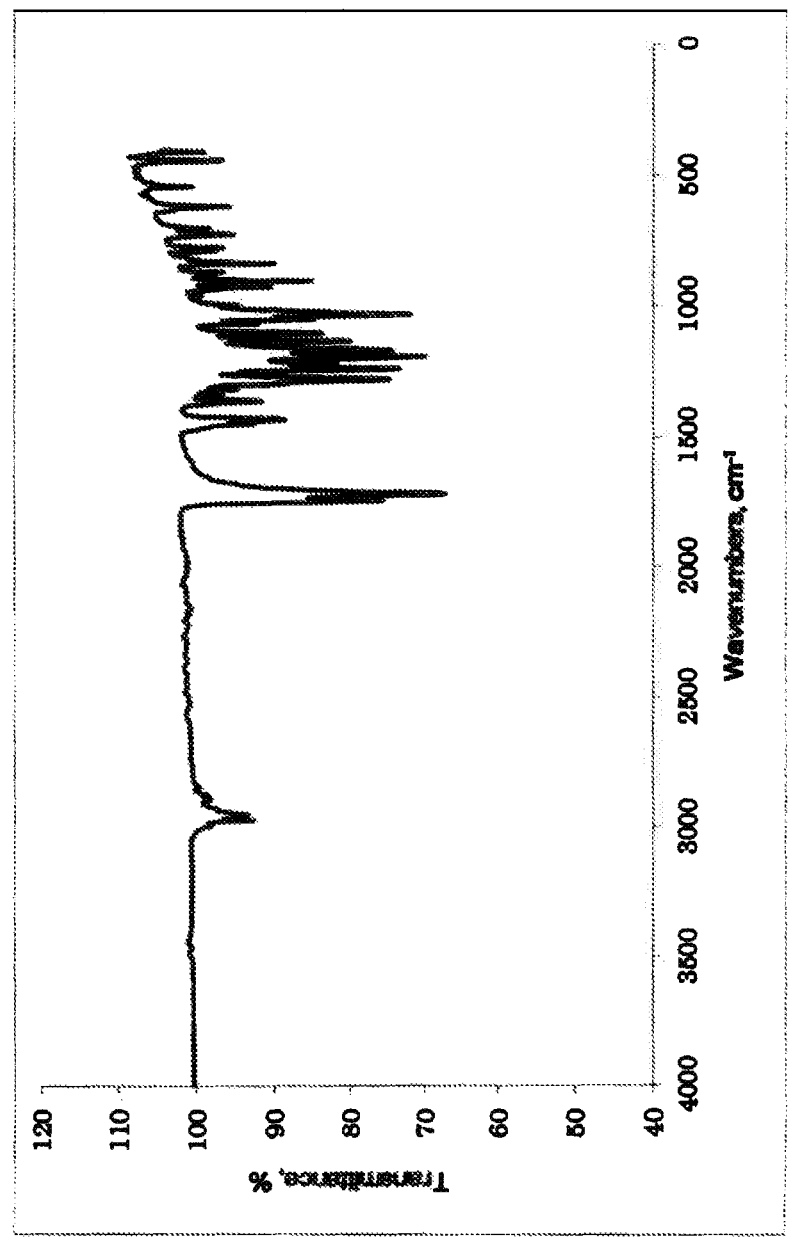
FIG. 1 is a graph showing an IR spectrum of a product obtained in Example 1.

Hereinafter, the present invention will be described in detail based on preferred embodiments thereof.

[Tetracarboxylic Dianhydride]

A tetracarboxylic dianhydride of the present invention comprises: at least one acid dianhydride (A) selected from the group consisting of compounds each having an endo/exo type three-dimensional structure represented by the general formula (1) and their enantiomeric compounds each having an exo/endo type three-dimensional structure; and/or an acid dianhydride (B) having an endo/endo type three-dimensional structure represented by the general formula (2), wherein a content of the acid dianhydride (B) in a total amount of the acid dianhydrides (A) and (B) is 30 to 100% by mole in a mole ratio.

Note that, as described above, the present inventors have found that it is possible to produce a polyimide having a sufficient light transmittance and a heat resistance at a higher level when the polyimide is produced by using the tetracarboxylic dianhydride represented by the general formula (A), and then found that the tetracarboxylic dianhydride represented by the general formula (A) includes two types of isomers: a stereoisomer A (acid dianhydride (A)) composed of a stereoisomer A1 having an endo/exo type structure represented by the general formula (1) and/or its enantiomeric stereoisomer A2 having an exo/endo type structure; and a stereoisomer B (acid dianhydride (B)) having an endo/endo type structure represented by the general formula (2) (note that the stereoisomer A1 and the stereoisomer A2 cannot be distinguished spectroscopically and thus are evaluated as equivalent isomers, which are referred to as "stereoisomer A"). Moreover, the present inventors have found that, by use of an acid dianhydride containing the acid dianhydride (B) in an amount of 30% by mole or more among two types of stereoisomers of the stereoisomer A (acid dianhydride (A)) and the stereoisomer B (acid dianhydride (B)), specifically, by use of a tetracarboxylic dianhydride (tetracarboxylic dianhydride represented by the general formula (A)) containing the acid dianhydride (B) in an amount of 30% by mole or more among tetracarboxylic dianhydrides composed of the acid dianhydride (A) and/or the acid dianhydride (B), it is possible not only to produce a polyimide having a sufficient light transmittance and a heat resistance at a higher level but also to more surely produce a polyimide with a higher mechanical strength among polyimides obtained by using the tetracarboxylic dianhydride represented by the general formula (A).

An alkyl group which may be selected as $R^1$ in the general formula (1) is an alkyl group having 1 to 10 carbon atoms. If the number of carbon atoms exceeds 10, the heat resistance of a polyimide obtained in the use as a monomer for the polyimide is lowered. In addition, the number of carbon atoms of such an alkyl group which may be selected as $R^1$ is preferably 1 to 6, more preferably 1 to 5, further preferably 1 to 4, and particularly preferably 1 to 3 from the viewpoint that a higher heat resistance can be obtained when a polyimide is produced. In addition, such an alkyl group which may be selected as $R^1$ may be linear or branched. Of multiple $R^1$s in the general formula (1), two $R^1$s connected to a common carbon atom may together form a methylidene group ($=CH_2$). To be more specific, two $R^1$s connected to a common carbon atom in the general formula (1) may together be connected to the carbon atom (of the carbon atoms forming a norbornane ring structure, the carbon atom connected with two $R^1$s) as a methylidene group (methylene group) via double bond.

Multiple $R^1$s in the general formula (1) are each independently more preferably a hydrogen atom, a methyl group, an ethyl group, an n-propyl group, and an isopropyl group, and particularly preferably a hydrogen atom and a methyl group, for example, from the viewpoint that a higher heat resistance can be obtained when a polyimide is produced, that the raw material is readily available, and that the purification is easier. In addition, multiple $R^1$s in the formula (1) may be the same as one another or different from one another, and are preferably the same from the viewpoints of ease of purification and the like.

$R^2$ and $R^3$ in the general formula (1) are each independently one selected from the group consisting of a hydrogen atom and alkyl groups having 1 to 10 carbon atoms. If the number of carbon atoms of such an alkyl group which may be selected as $R^2$ and $R^3$ exceeds 10, the heat resistance of a polyimide obtained in the use as a monomer for the polyimide is lowered. In addition, such an alkyl group which may be selected as $R^2$ and $R^3$ is preferably 1 to 6, more preferably 1 to 5, further preferably 1 to 4, and particularly preferably 1 to 3 from the viewpoint that a higher heat resistance can be obtained when a polyimide is produced. In addition, such an alkyl group which may be selected as $R^2$ and $R^3$ may be linear or branched.

$R^2$ and $R^3$ in the general formula (1) are each independently more preferably a hydrogen atom, a methyl group, an ethyl group, an n-propyl group, and an isopropyl group, and particularly preferably a hydrogen atom and a methyl group, for example, from the viewpoint that a higher heat resistance can be obtained when a polyimide is produced, that the raw material is readily available, and that the purification is easier. In addition, the $R^2$ and $R^3$ in the formula (1) may be the same as each other or different from each other, and are preferably the same from the viewpoints of ease of purification and the like.

In addition, each of multiple $R^1$s, $R^2$, and $R^3$ in the general formula (1) is particularly preferably a hydrogen atom. As described above, in the compound represented by the general formula (1), if each of the substituents represented by $R^1$s, $R^2$, and $R^3$ is a hydrogen atom, the yield of the compound tends to increase. In addition, when a polyimide containing the compound as a monomer is produced, a higher heat resistance tends to be obtained.

In the general formula (2), $R^2$, and $R^3$ have the same meanings as those of $R^1$s, $R^2$, and $R^3$ in the general formula (1), respectively, and preferred ones thereof are also the same.

Note that, although the acid dianhydride (A) may contain a compound having an endo/exo type three-dimensional structure and a compound having an exo/endo type three-dimensional structure, the acid dianhydride (A) may contain one of the compounds alone or may contain both of the compounds.

In addition, the tetracarboxylic dianhydride of the present invention comprises: at least one acid dianhydride (A) selected from the group consisting of compounds each having an endo/exo type three-dimensional structure represented by the general formula (1) and their enantiomeric compounds each having an exo/endo type three-dimensional structure; and/or an acid dianhydride (B) having an endo/endo type three-dimensional structure represented by the general formula (2), wherein a content of the acid dianhydride (B) in a total amount of the acid dianhydrides (A) and (B) is 30 to 100% by mole in a mole ratio. If the content of the acid dianhydride (B) is less than the lower limit, a polyimide produced by using that acid dianhydride tends to have a lowered mechanical strength based on the elongation at break.

Moreover, the content of the acid dianhydride (B) is more preferably 40 to 100% by mole, further preferably 60 to 100% by mole, particularly preferably 80 to 100% by mole, and most preferably 90 to 100% by mole. If the content of the acid dianhydride (B) is in the preferable range, a polyimide produced by using that acid dianhydride tends to have a higher mechanical strength based on the elongation at break.

When a polyimide is produced by using such a tetracarboxylic dianhydride of the present invention as a monomer, it is also possible to reduce the loss tangent (tan δ) to a lower value compared to the case where a conventional alicyclic tetracarboxylic dianhydride is utilized. For this reason, for example, it is possible to sufficiently reduce transmission loss when a polyimide containing the tetracarboxylic dianhydride of the present invention as a monomer is produced and the resultant is utilized in interlayer insulating film material for semiconductor, aboard film for a flexible printed circuit board (FPC), and the like.

A method for producing a tetracarboxylic dianhydride of the present invention is not particularly limited. Note that the method for producing a tetracarboxylic dianhydride of the present invention is described later.

[Carbonyl Compound]

A carbonyl compound of the present invention comprises: at least one carbonyl compound (A) selected from the group consisting of compounds each having an endo/exo type three-dimensional structure represented by the general formula (3) and their enantiomeric compounds each having an exo/endo type three-dimensional structure; and/or a carbonyl compound (B) having an endo/endo type three-dimensional structure represented by the general formula (4), wherein a content of the carbonyl compound (B) in a total amount of the carbonyl compounds (A) and (B) is 30 to 100% by mole in a mole ratio. Note that, regarding the carbonyl compounds, the compounds each having an endo/exo type three-dimensional structure and their enantiomeric compounds each having an exo/endo type three-dimensional structure cannot be distinguished spectroscopically, and thus are referred to as the "carbonyl compound (A)."

$R^1$s, $R^2$, and $R^3$ in the general formula (3) are the same as $R^1$s, $R^2$, and $R^3$ in the general formula (1), and preferred ones thereof are also the same as $R^1$s, $R^2$, and $R^3$ in the general formula (1). Note that multiple $R^1$s in the general formula (3) may be the same as one another or different from one another, and are preferably the same from the viewpoint of ease of purification and the like. Moreover, $R^2$ and $R^3$ in the general formula (3) may be the same as each other or different from each other, and are preferably the same from the viewpoint of ease of purification and the like.

Each of multiple $R^1$s, $R^2$, and $R^3$ in the general formula (3) is particularly preferably a hydrogen atom. As described above, in the compound represented by the general formula (3), if each of the substituents represented by $R^1$s, $R^2$, and $R^3$ is a hydrogen atom, the yield of the compound tends to increase. In addition, when an acid dianhydride is formed from the compound and a polyimide containing the obtained acid dianhydride as a monomer is produced, a higher heat resistance tends to be obtained.

In addition, an alkyl group which may be selected as $R^4$ in the general formula (3) is an alkyl group having 1 to 10 carbon atoms. If the number of carbon atoms of such an alkyl group exceeds 10, purification is difficult. In addition, the number of carbon atoms of such an alkyl group which may be selected as multiple $R^4$s is more preferably 1 to 5 and further preferably 1 to 3 from the viewpoint that the purification is easier. In addition, such an alkyl group which may be selected as multiple $R^4$s may be linear or branched.

In addition, a cycloalkyl group which may be selected as $R^4$ in the general formula (3) is a cycloalkyl group having 3 to 10 carbon atoms. If the number of carbon atoms of such a cycloalkyl group exceeds 10, purification is difficult. In addition, the number of carbon atoms of such a cycloalkyl group which may be selected as multiple $R^4$s is more preferably 3 to 8 and further preferably 5 and 6 from the viewpoint that the purification is easier.

Moreover, an alkenyl group which may be selected as $R^4$ in the general formula (3) is an alkenyl group having 2 to 10 carbon atoms. If the number of carbon atoms of such an alkenyl group exceeds 10, purification is difficult. In addition, the number of carbon atoms of such an alkenyl group which may be selected as multiple $R^4$s is more preferably 2 to 5 and further preferably 2 and 3 from the viewpoint that the purification is easier.

In addition, an aryl group which may be selected as $R^4$ in the general formula (3) is an aryl group having 6 to 20 carbon atoms. If the number of carbon atoms of such an aryl group exceeds 20, purification is difficult. In addition, the number of carbon atoms of such an aryl group which may be selected as multiple $R^4$s is more preferably 6 to 10 and further preferably 6 to 8 from the viewpoint that the purification is easier.

In addition, an aralkyl group which may be selected as $R^4$ in the general formula (3) is an aralkyl group having 7 to 20 carbon atoms. If the number of carbon atoms of such an aralkyl group exceeds 20, purification is difficult. In addition, the number of carbon atoms of such an aralkyl group which may be selected as multiple $R^4$s is more preferably 7 to 10 and further preferably 7 to 9 from the viewpoint that the purification is easier.

Moreover, multiple $R^4$s in the general formula (3) are each independently preferably a methyl group, an ethyl group, an n-propyl group, an isopropyl group, an n-butyl group, an isobutyl group, a sec-butyl, a t-butyl, a cyclohexyl group, an allyl group, a phenyl group, or a benzyl group, more preferably a methyl group, an ethyl group, or an n-propyl group, further preferably a methyl group or an ethyl group, and particularly preferably a methyl group from the viewpoint that the purification is easier. Note that multiple $R^4$s in the general formula (3) may be the same as one another or different from one another, and are more preferably the same from the viewpoint of synthesis.

In addition, $R^1$s, $R^2$, $R^3$, and $R^4$s in the general formula (4) are the same as $R^1$s, $R^2$, $R^3$, and $R^4$s in the general formula (3), and preferred ones thereof are also the same.

Note that, although the carbonyl compound (A) may contain a compound having an endo/exo type three-dimensional structure and a compound having an exo/endo type three-dimensional structure, the carbonyl compound (A) may contain one of the compounds alone or may contain both of the compounds.

In addition, the tetracarboxylic dianhydride of the present invention comprises: at least one carbonyl compound (A) selected from the group consisting of compounds each having an endo/exo type three-dimensional structure represented by the general formula (3) and their enantiomeric compounds each having an exo/endo type three-dimensional structure; and/or a carbonyl compound (B) having an endo/endo type three-dimensional structure represented by the general formula (4), wherein a content of the carbonyl compound (B) in a total amount of the carbonyl compounds (A) and (B) is 30 to 100% by mole in a mole ratio. If the content of the carbonyl compound (B) is less than the lower limit, a polyimide, produced by using that carbonyl compound and using a produced acid anhydride, tends to have a lowered mechanical strength based on the elongation at break.

Moreover, the content of the carbonyl compound (B) is more preferably 40 to 100% by mole, further preferably 60 to 100% by mole, particularly preferably 80 to 100% by mole, and most preferably 90 to 100% by mole. If the content of the carbonyl compound (B) is in the preferable range, a polyimide produced by using that carbonyl compound tends to have a higher mechanical strength based on the elongation at break.

(Method for Producing Tetracarboxylic Dianhydride)

A method which can be preferably employed as a method for producing a carbonyl compound of the present invention will be described. Such a method for producing a carbonyl compound is not particularly limited, and it is possible to employ a method for obtaining the carbonyl compound of the present invention, the method including, for example, performing a step (I) of reacting a norbornene-based compound represented by the following general formula (I):

[Chem. 10]

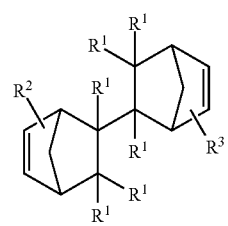

(I)

[in the formula (I), $R^1$s, $R^2$, and $R^3$ have the same meanings as those of $R^1$s, $R^2$, and $R^3$ in the formula (3), respectively (preferred ones thereof also have the same meanings)] with an alcohol and carbon monoxide in the presence of a palladium catalyst and an oxidant, to thereby obtain a carbonyl compound represented by the following general formula (II):

[Chem. 11]

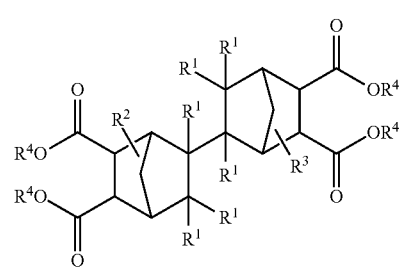

(II)

[in the formula (II), $R^1$s, $R^2$, $R^3$, and $R^4$s have the same meanings as those of $R^1$s, $R^2$, $R^3$, and $R^4$s in the formula (3), respectively (preferred ones thereof also have the same meanings)] (compound containing the carbonyl compound (A) and/or the carbonyl compound (B)), wherein if, of the carbonyl compounds, the content of the carbonyl compound (B), a stereoisomer, is 30% by mole or more, the carbonyl compound obtained by the step (I) may be used directly as the carbonyl compound of the present invention, and on the other hand, if, of the carbonyl compounds, the content of the carbonyl compound (B), a stereoisomer, is less than 30% by mole or if it is necessary to increase the content of the carbonyl compound (B), a property that the carbonyl compound (B) has a higher crystallinity than the carbonyl compound (A) and is easily precipitated by crystallization (conversely, the carbonyl compound (A) is hardly precipitated by crystallization) may be used to dissolve the carbonyl compound obtained in the step (I) in a solvent, followed by crystallization to obtain a carbonyl compound having a higher content of the carbonyl compound (B) and represented by the general formula (II).

In the present invention, the production of the carbonyl compound utilizes the norbornene-based compound represented by the general formula (I) as a raw material compound. The norbornene-based compound (I) may contain at least one norbornene-based compound (A) selected from the group consisting of compounds each having an endo/exo type three-dimensional structure represented by the following general formula (I-1) and their enantiomeric compounds each having an exo/endo type three-dimensional structure, and/or a norbornene-based compound (B) having an endo/endo type three-dimensional structure represented by the following general formula (I-2)

[Chem. 12]

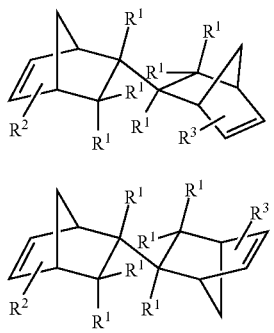

(I-1)

(I-2)

[in the formulae (I-1) and (I-2), $R^1$s, $R^2$, and $R^3$ have the same meanings as those of $R^1$s, $R^2$, and $R^3$ in the formula (3), respectively (preferred ones thereof also have the same meanings)].

Each of the substituents represented by $R^1$s, $R^2$, and $R^3$ in the general formulae (I), (I-1), and (I-2) is preferably a hydrogen atom, which tends to increase the yield of the compounds. In addition, when a polyimide containing the compounds as a monomer is produced, a higher heat resistance tends to be obtained. Here, examples of the compound represented by the general formula (I) include 5,5'-bibicyclo[2.2.1]hept-2-ene (also referred to as: 5,5'-bi-2-norbornene) (CAS number: 36806-67-4), 3-methyl-3'-methylene-2,2'-bis(bicyclo[2.2.1]heptene-5,5'-diene) (CAS number: 5212-61-3), 5,5'-bisbicyclo[2.2.1]hept-5-ene-2,2'-diol (CAS number: 15971-85-4), and the like. The method for producing the compound represented by the general formula (I) is not particularly limited, and may employ as appropriate a known method. Note that, by appropriately changing the production conditions of the norbornene-based compound (I), it is possible to appropriately change the content ratios of the at least one norbornene-based compound (A) selected from the group consisting of compounds each having an endo/exo type three-dimensional structure represented by the general formula (I-1) and their enantiomeric compounds each having an exo/endo type three-dimensional structure, and the norbornene-based compound (B) having an endo/endo type three-dimensional structure represented by the general formula (I-2).

In addition, the alcohol to be reacted with the norbornene-based compound is not particularly limited, and is preferably an alcohol represented by the following general formula (10):

$$R^aOH \qquad (10)$$

[in the formula (10), $R^a$ is an atom or a group other than a hydrogen atom which may be selected as $R^4$ in the general formula (II) (note that $R^4$ in the formula (II) has the same meaning as that of $R^4$ in the formula (3))] from the viewpoint of ease of purification. To be more specific, it is preferable to use, as such an alcohol, alkyl alcohol having 1 to 10 carbon atoms, cycloalkyl alcohol having 3 to 10 carbon atoms, alkenyl alcohol having 2 to 10 carbon atoms, aryl alcohol having 6 to 20 carbon atoms, and aralkyl alcohol having 7 to 20 carbon atoms.

Such an alcohol includes, specifically, methanol, ethanol, butanol, allyl alcohol, cyclohexanol, benzyl alcohol, and the like, of which methanol and ethanol are more preferable and methanol is particularly preferable from the viewpoint that the purification of the obtained compound is easier. Note that one of these alcohols can be used alone, or two or more thereof can be used in combination.

In addition, in the present invention, the reaction of the alcohol (preferably $R^aOH$), carbon monoxide (CO), and the norbornene-based compound represented by the general formula (I) makes it possible to introduce an ester group (regarding such an ester group, $R^4$s at positions for introduction may be the same as one another or different from one another) represented by the following general formula (11):

$$-COOR^a \qquad (11)$$

[in the formula (11), $R^a$ is an atom or a group other than a hydrogen atom which may be selected as $R^4$ in the general formula (II)] into each of the carbon atoms at the olefin portions in the norbornene-based compound represented by the general formula (I) in the presence of a palladium catalyst and an oxidant. This makes it possible to obtain the carbonyl compound represented by the general formula (II). As described above, the present invention makes it possible to obtain the carbonyl compound represented by the general formula (II) by using an alcohol (preferably $R^aOH$) and carbon monoxide (CO) and by utilizing a reaction (hereinafter, such a reaction is sometimes simply referred to as "esterification reaction") to introduce an ester group into each of the carbon atoms at the olefin portions in the carbonyl compound in the presence of a palladium catalyst and an oxidant.

The palladium catalyst used in such an esterification reaction is not particularly limited, and a known catalyst containing palladium can be used as appropriate. Examples include a palladium salt of an inorganic acid, a palladium salt of an organic acid, a catalyst whose support supports palladium, and the like. In addition, preferable examples of such a palladium catalyst include palladium chloride, palladium nitrate, palladium sulfate, palladium acetate, palladium propionate, palladium on carbon, palladium on alumina, palladium black, palladium acetate having nitrite ligand (formula: $Pd_3(CH_3COO)_5(NO_2)$, and the like.

In addition, as such a palladium catalyst, it is preferable to use a palladium catalyst containing palladium acetate having nitrite ligand (catalyst represented by the formula: $Pd_3(CH_3COO)_5(NO_2)$) (hereinafter, sometimes simply referred to as "$Pd_3(OAc)_5(NO_2)$") from the viewpoint that it is possible to more sufficiently suppress the production of by-products and to produce the carbonyl compound represented by the general formula (II) with a higher selectivity.

In addition, in the palladium catalyst containing palladium acetate having such a nitrite ligand ($Pd_3(OAc)_5(NO_2)$), the content of palladium acetate having the nitrite ligand ($Pd_3(OAc)_5(NO_2)$) is preferably 10% by mole or more in terms of metal (in the total amount of palladium in the palladium catalyst). If the content ratio of palladium acetate having such a nitrite ligand is less than the lower limit, it tends to be difficult to sufficiently suppress the production of by-products and to produce the carbonyl compound represented by the general formula (II) with a sufficiently high selectivity. In addition, as the palladium catalyst, the content ratio of palladium acetate having the nitrite ligand ($Pd_3(OAc)_5(NO_2)$) is more preferably 30% by mole or more, further preferably 40% by mole or more, particularly preferably 50% by mole or more, and most preferably 70% by mole to 100% by mole in terms of metal (in the total amount of palladium in the palladium catalyst) from the viewpoint that it is possible to suppress the production of by-products at a higher level and to produce an ester compound with a higher selectivity.

In addition, if the palladium catalyst used in the esterification reaction is one which contains palladium acetate having the nitrite ligand ($Pd_3(OAc)_5(NO_2)$), another catalyst (another palladium catalyst component) which can be contained other than $Pd_3(OAc)_5(NO_2)$ is not particularly limited, and it is possible to use as appropriate a known palladium-based catalyst component (for example, palladium chloride, palladium nitrate, palladium sulfate, palladium acetate, palladium propionate, palladium on carbon, palladium on alumina, palladium black, and the like) usable when reacting the olefin portions with carbon monoxide and an alcohol (during esterification).

In addition, as a component (palladium-based catalyst component) other than palladium acetate having the nitrite ligand which may be contained in such a palladium catalyst, it is preferable to use palladium acetate from the viewpoint of suppressing the production of by-products such as polymerization products and improving selectivity. In addition, as the palladium catalyst, it is possible to more preferably utilize a mixture catalyst of palladium acetate having the nitrite ligand ($Pd_3(OAc)_5(NO_2)$) and palladium acetate, and a catalyst made only of palladium acetate having the nitrite ligand ($Pd_3(OAc)_5(NO_2)$) from the viewpoint of suppressing the production of by-products such as polymerization products and improving selectivity.

Note that a method for producing palladium acetate having such a nitrite ligand ($Pd_3(OAc)_5(NO_2)$) is not particularly limited, and a known method can be used as appropriate. For example, one may use e.g. a method described in pages 1989 to 1992 of Dalton Trans (vol. 11) published on Jun. 7, 2005 (author: Vladimir I, Bakhmutov, et al.).

In addition, the oxidant used in the esterification reaction may be one which can oxidize $Pd^0$ to $Pd^{2+}$, where $Pd^0$ is created by reduction of $Pd^{2+}$ in the palladium catalyst in the esterification reaction. Such an oxidant is not particularly limited, and examples thereof include a copper compound, an iron compound, and the like. In addition, such an oxidant includes, specifically, copper(II) chloride, copper(II) nitrate, copper(II) sulfate, copper(II) acetate, iron(II) chloride, iron (II) nitrate, iron(II) sulfate, iron(II) acetate, and the like.

Moreover, the amount of alcohol used in such an esterification reaction may be an amount which makes it possible to obtain the compound represented by the general formula (II) and is not particularly limited. For example, in order to obtain the compound represented by the general formula (II), the alcohol may be added in an amount equal to or more than theoretically necessary (theoretical value) and surplus alcohol may be used as a solvent as it is.

In addition, in the esterification reaction, it suffices that the carbon monoxide can be supplied to the reaction system in a necessary amount. For this reason, it is unnecessary to use a high-purity gas of carbon monoxide as the carbon monoxide, and a mixture gas in which a gas inert to the esterification reaction (for example, nitrogen) and carbon monoxide are mixed may be used. In addition, the pressure of such a carbon monoxide is not particularly limited, and is preferably normal pressure (approximately 0.1 MPa [1 atm]) or more and 10 MPa or less.

Moreover, the method for supplying the carbon monoxide to the reaction system is not particularly limited, and a known method can be used as appropriate. Examples of the method include a method for supplying by bubbling the carbon monoxide into a mixture liquid of the alcohol, the compound represented by the general formula (I), and the palladium catalyst, and in the case of using a reaction vessel, a method for supplying the carbon monoxide to the reaction system by introducing the carbon monoxide into the atmospheric gas in the vessel, and the like.

In addition, in the case of supplying the carbon monoxide into the mixture liquid containing the alcohol, the compound represented by the general formula (I), and the palladium catalyst, it is preferable to supply the carbon monoxide at a rate (supply rate) of 0.002 to 0.2 mole equivalents/min (more preferably 0.005 to 0.1 mole equivalents/min and further preferably 0.005 to 0.05 mole equivalents/min) to the compound represented by the general formula (I). If the supply rate of carbon monoxide is less than the lower limit, the reaction rate is slow and by-products such as polymerization products tend to be produced. Meanwhile, if the supply rate of carbon monoxide exceeds the upper limit, it tends to be difficult to control the reaction because the reaction rate improves and the reaction rapidly proceeds. Note that theoretically, 4 mole equivalents of carbon monoxide react with 1 mole of the compound represented by the general formula (I) being a raw material, which means that if the rate (supply rate) is 0.1 mole equivalents/min, for example, it takes 40 minutes (4 [mole equivalents]/0.1 [mole equivalents/min]=40 minutes) in order to introduce theoretical value 4 mole equivalents to 1 mole of the compound of the general formula (1). In addition, as a method for supplying carbon monoxide at such a supply rate, it is preferable to employ a method for supplying by bubbling carbon monoxide into a mixture liquid of the alcohol, the compound represented by the general formula (I), and the palladium catalyst.

In addition, in the case of supplying by bubbling the carbon monoxide, a specific method for the bubbling is not particularly limited, and a known bubbling method can be employed as appropriate. For example, carbon monoxide may be supplied by bubbling into a mixture liquid using what is called a bubbling nozzle, a tube provided with numerous pores, or the like as appropriate.

Moreover, a method for controlling the supply rate of the carbon monoxide is not particularly limited, and a known control method may be employed as appropriate. For example, in the case of supplying carbon monoxide by bubbling, a method for controlling the supply rate of carbon monoxide at the rate by using a known apparatus which can supply a gas at a certain rate to the bubbling nozzle, the tube provided with numerous pores, or the like. In addition, in the case of supplying carbon monoxide by bubbling, if a reaction vessel is used, it is preferable to adjust the bubbling nozzle, the tube, or the like to near a bottom portion of the vessel. The purpose of this is to promote contact between the compound represented by the general formula (I) present at the bottom portion and carbon monoxide supplied from the bubbling nozzle or the like.

In addition, in the esterification reaction, the amount of the palladium catalyst used is preferably such an amount that the amount of moles of palladium in the palladium catalyst is 0.001 to 0.1 times (more preferably 0.001 to 0.01 times) the amount of moles of the norbornene-based compound represented by the general formula (I). If the amount of such a palladium catalyst used is less than the lower limit, the reaction rate is lowered and thus the yield tends to be lowered. Meanwhile, if the amount of such a palladium catalyst used exceeds the upper limit, it tends to be difficult to remove palladium from the product and the purity of the product tends to be lowered.

The amount of such an oxidant used is preferably 2 to 16 times (more preferably 2 to 8 times and further preferably 2 to 6 times) the amount of moles of the norbornene-based compound represented by the general formula (I). If the amount of such an oxidant used is less than the lower limit, it is impossible to sufficiently promote the oxidization reaction of palladium and as a result by-products tend to be produced in a large amount. Meanwhile, if the amount of such an oxidant used exceeds the upper limit, purification is difficult and the purity of the products tends to be lowered.

In addition, a solvent may be used in the reaction (esterification reaction) among the norbornene-based compound represented by the general formula (I), the alcohol, and carbon monoxide. Such a solvent is not particularly limited, and a known solvent usable in the esterification reaction can be used as appropriate. Examples thereof include hydrocarbon-based solvents such as n-hexane, cyclohexane, benzene, toluene, and the like.

Moreover, in the esterification reaction, since an acid is produced as a by-product from the oxidant and the like, a base may be added in order to remove such an acid. Such a base is preferably a fatty acid salt such as sodium acetate, sodium propionate, sodium butyrate, or the like. In addition, the amount of such a base used may be adjusted as appropriate depending on e.g. the amount of acid produced.

In addition, the reaction temperature condition in the esterification reaction is not particularly limited, and is preferably 0° C. to 200° C. {more preferably a temperature of 0° C. to 100° C., further preferably about 10 to 60° C., and particularly preferably about 20 to 50° C.}. If such a reaction temperature exceeds the upper limit, the yield tends to be lowered. Meanwhile, if such a reaction temperature is less than the lower limit, the reaction rate tends to be lowered. In addition, the reaction time of the esterification reaction is not particularly limited, and is preferably about 30 minutes to 24 hours.

In addition, the atmospheric gas in the esterification reaction is not particularly limited, and a gas usable in the esterification reaction can be used as appropriate. Examples include a gas inert to the esterification reaction (nitrogen, argon, or the like), carbon monoxide, and a mixture gas of carbon monoxide and another gas (nitrogen, air, oxygen, hydrogen, carbon dioxide, argon, or the like), and preferably carbon monoxide, a gas inert to the esterification reaction, and a mixture gas of carbon monoxide and a gas inert to the esterification reaction from the viewpoint that they do not affect the catalyst or the oxidant. Note that in the case of employing the method for introducing carbon monoxide by bubbling as a method for supplying carbon monoxide into the mixture liquid, the reaction may be caused to proceed such that before the reaction, the atmospheric gas is a gas inert to the esterification reaction, the reaction is started by the aforementioned bubbling, and as a result the atmospheric gas becomes a mixture gas of carbon monoxide and the gas inert to the esterification reaction, for example.

Moreover, the pressure condition in the esterification reaction (pressure condition of atmospheric gas: pressure condition of the gas in the reaction vessel if the reaction is caused to proceed in the vessel) is not particularly limited, and is preferably 0.05 MPa to 15 MPa, more preferably normal pressure (0.1 MPa [1 atm]) to 15 MPa, further preferably 0.1 MPa to 10 MPa, and particularly preferably 0.11 MPa to 5 MPa. If such a pressure condition is less than the lower limit, the reaction rate is lowered and the yield of the target product tends to be lowered. Meanwhile, if such a pressure condition exceeds the upper limit, it tends to be difficult to control the reaction because the reaction rate improves and the reaction rapidly proceeds, and the facility capable of carrying out the reaction tends to be limited.

If the esterification reaction is caused to proceed as described above, it is possible to obtain the carbonyl compound (tetraester compound) represented by the general formula (II) in which each of $R^4$s in the formula (II) is a group other than a hydrogen atom. In addition, in the case of producing the carbonyl compound represented by the general formula (II) in which each of $R^4$s in the formula (II) is a hydrogen atom, one may introduce a group represented by the formula: —COO$R^a$ by the esterification reaction and then, in order to convert such a group to a group represented by the formula: —COOH having a hydrogen atom in place of $R^a$, carry out a hydrolysis process or a transesterification reaction with a carboxylic acid. A method for such a reaction is not particularly limited, and a known method can be employed as appropriate which makes it possible to convert the group represented by the formula —COO$R^a$ (ester group) to the formula: —COOH (carboxy group).

By performing the step (I) as described above, it is possible to obtain the carbonyl compound represented by the general formula (II) having the target structure. Note that the carbonyl compound obtained in the step (I) and represented by the general formula (II) is a compound whose content rates of the carbonyl compound (A) and the carbonyl compound (B) differ depending on the rates of the norbornene-based compound (A) and the norbornene-based compound (B) in the norbornene-based compound used as a raw material. Then, if the content of the carbonyl compound (B) in the carbonyl compound obtained in the step (I) is initially 30% by mole or more and at a desired rate, this can be obtained as it is as the carbonyl compound of the present invention. Note that, by using a raw material compound having a high rate of the norbornene-based compound (B), it is possible to more easily obtain in the step (I) a carbonyl compound of the present invention in which the content of the carbonyl compound (B) is initially 30% by mole or more.

On the other hand, if the content of the carbonyl compound (B) in the carbonyl compound obtained in the step (I) is less than 30% by mole, or is 30% by mole or more but is wished to be adjusted to a desired rate (for example, in the case of eventually producing a polyimide which is wished to have a higher value of the content of the carbonyl compound (B) depending on the intended design), the content of the carbonyl compound (B) may be adjusted to a higher value by appropriately performing a step of, after obtaining the carbonyl compound by the step (I), dissolving the carbonyl compound in a solvent, followed by crystallization by virtue of a property that the carbonyl compound (B) has a higher crystallinity than the carbonyl compound (A) and is easily precipitated by crystallization (conversely, the carbonyl compound (A) has a property that it is hardly precipitated by crystallization). The crystallization step makes it possible to adjust the rates of the carbonyl compound (B) and the carbonyl compound (A) in the carbonyl compound represented by the general formula (II), and to obtain the carbonyl compound of the present invention.

Note that, as the crystallization step, it is possible to use a known method as appropriate. For example, if the carbonyl compound obtained in the step (I) and represented by the general formula (II) is a mixture of the carbonyl compound (A) and the carbonyl compound (B), the carbonyl compound of the present invention can be obtained as follows. After the carbonyl compound (the mixture) represented by the general formula (II) is dissolved in an organic solvent, the solution is appropriately concentrated to deposit precipitates (crystals) in the solution, followed by filtration to separate the precipitates and the filtrate (which basically tends to be oily). Then, the components on the precipitate side have a high content ratio of the easily crystallizable carbonyl compound (B), and on the other hand, the components on the filtrate side have a high content ratio of the hardly crystallizable carbonyl compound (A). Thus, the precipitates (crystals) are collected for purification as appropriate. Note that such concentration and filtration steps may be repeated to thereby adjust the content ratio of the carbonyl compound (B) to a desired value. Note that, since the filtration step increases the content ratio of the carbonyl compound (A) on the filtrate side as described above, the filtrate also makes it possible to obtain a carbonyl compound having a high content ratio of the carbonyl compound (A). For this reason, for example, a carbonyl compound to be used for various applications may be made by preparing in advance a single compound of the carbonyl compound (B) or a carbonyl compound represented by the general formula (II) and having a high content ratio of the carbonyl compound (B) as a stereoisomer, followed by mixing with a carbonyl compound having a high content ratio of the carbonyl compound (A) obtained by using the above-described filtrate, to thereby adjust the rates of the carbonyl compounds (A) and (B) to the desired rates.

(Method for Producing Tetracarboxylic Dianhydride of Present Invention)

A method which can be preferably employed as a method for producing a tetracarboxylic dianhydride of the present invention will be described. As such a method for producing a tetracarboxylic dianhydride of the present invention, it is possible to employ, for example, a method including heating a raw material compound composed of the carbonyl compound of the present invention in a carboxylic acid having 1 to 5 carbon atoms with an acid catalyst being used, to thereby obtain the tetracarboxylic dianhydride of the present invention.

An acid catalyst used in the method is not particularly limited, and may be a homogeneous acid catalyst or an inhomogeneous acid catalyst (solid catalyst). Among such acid catalysts, the homogeneous acid catalyst is preferable from the viewpoint of ease of purification.

Such a homogeneous acid catalyst is not particularly limited, and it is possible to appropriately utilize a known homogeneous acid catalyst which can be used in reacting a carboxylic acid into an anhydride and in reacting an ester compound into an acid anhydride. Examples of such a homogeneous acid catalyst include trifluoromethanesulfonic acid, tetrafluoroethanesulfonic acid, pentafluoroethanesulfonic acid, heptafluoropropanesulfonic acid, heptafluoroisopropanesulfonic acid, nonafluorobutanesulfonic acid, heptafluorodecanesulfonic acid, bis(nonafluorobutanesulfonyl)imide, N,N-bis(trifluoromethanesulfonyl)imide, and chlorodifluoroacetic acid. In addition, such a homogeneous acid catalyst is more preferably trifluoromethanesulfonic acid, tetrafluoroethanesulfonic acid, nonafluorobutanesulfonic acid, and chlorodifluoroacetic acid and further preferably trifluoromethanesulfonic acid and tetrafluoroethanesulfonic acid from the viewpoint of improvement in reaction yield. Note that one of these homogeneous acid catalysts can be used alone, or two or more thereof can be used in combination.

In addition, the amount of the acid catalyst (more preferably a homogeneous acid catalyst) used is not particularly limited, and is preferably such that the amount of moles of the acid of the acid catalyst is 0.001 to 2.00 mole equivalents (more preferably 0.01 to 1.00 mole equivalents) in the amount of the carbonyl compound (raw material compound of the tetracarboxylic dianhydride) of the present invention used (amount of moles). If the amount of such an acid catalyst used is less than the lower limit, the reaction rate tends to be lowered. Meanwhile, if the amount of such an acid catalyst used exceeds the upper limit, purification is rather difficult and the purity of the product tends to be lowered. Note that the amount of moles of the acid of the acid catalyst herein is the amount of moles in terms of the functional groups (for example, a sulfonic acid group (sulfo group) and a carboxylic acid group (carboxy group)) in the acid catalyst.

In addition, the amount of the acid catalyst (more preferably a homogeneous acid catalyst) used is preferably 0.1 to 100 parts by mass and more preferably 1 to 20 parts by mass in 100 parts by mass of the carbonyl compound (raw material compound) of the present invention. If the amount of such an acid catalyst used is less than the lower limit, the reaction rate tends to be lowered. Meanwhile, if the amount of such an acid catalyst used exceeds the upper limit, by-products tend to increase.

Moreover, the method uses a carboxylic acid having 1 to 5 carbon atoms (hereinafter, sometimes simply referred to as "lower carboxylic acid"). If the number of carbon atoms of such a lower carboxylic acid exceeds the upper limit, production and purification are difficult. In addition, examples of such a lower carboxylic acid include formic acid, acetic acid, propionic acid, butyric acid, and the like, of which formic acid, acetic acid, and propionic acid are preferable, and formic acid and acetic acid are more preferable from the viewpoint of ease of production and purification. One of these lower carboxylic acids can be used alone, or two or more thereof can be used in combination. In addition, the amount of such a lower carboxylic acid (for example, formic acid, acetic acid, and propionic acid) used is not particularly limited, and is preferably such that the amount of moles of the lower carboxylic acid is 4 to 100 times the amount of moles of the carbonyl compound represented by the general formula (2). If the amount of such a lower carboxylic acid (for example, formic acid, acetic acid, and propionic acid) used is less than the lower limit, the yield tends to be lowered. Meanwhile, if the amount of such a lower carboxylic acid exceeds the upper limit, the reaction rate tends to be lowered.

In addition, since the method heats the carbonyl compound (raw material compound) of the present invention in the lower carboxylic acid, it is preferable that the carbonyl compound be contained in the lower carboxylic acid. The content of the carbonyl compound of the present invention in such a lower carboxylic acid is preferably 1 to 40% by mass and more preferably 2 to 30% by mass. If the content of such a carbonyl compound is less than the lower limit, the yield tends to be lowered. Meanwhile, if the content of such a carbonyl compound exceeds the upper limit, the reaction rate tends to be lowered.

Note that in the method, if the carbonyl compound (raw material compound) of the present invention is a compound (tetracarboxylic acid) in which all of $R^4$s in the formula are hydrogen atoms, the heating step causes a reaction (forward reaction) to proceed in which the tetracarboxylic dianhydride and water are produced from the carbonyl compound (tetracarboxylic acid). Meanwhile, such a forward reaction and the reverse reaction in which the carbonyl compound (tetracarboxylic acid) is produced from the tetracarboxylic dianhydride and water are equilibrium reactions. In addition, in the method, if the carbonyl compound is a compound in which any of $R^4$s in the formula is a group other than a hydrogen atom, the heating step causes a reaction (forward reaction) to proceed in which the tetracarboxylic dianhydride, an ester compound of the lower carboxylic acid, and water are produced from the carbonyl compound and the lower carboxylic acid. Meanwhile, such a forward reaction and the reverse reaction in which the carbonyl compound and the lower carboxylic acid are produced from the carboxylic anhydride, the ester compound of the lower carboxylic acid, and water are equilibrium reactions. For this reason, in such a heating step, it is also possible to cause the reaction (forward reaction) to proceed efficiently by changing the concentrations and the like of the components in the system, as appropriate.

In addition, the conditions which may be employed in such a heating step (including conditions such as the heating temperature and an atmosphere) are not particularly limited, and if the method (conditions) makes it possible to heat the carbonyl compound (raw material compound) of the present invention in the lower carboxylic acid by using the acid catalyst, to thereby convert an ester group and/or a carboxy group (carboxylic acid group) in the carbonyl compound to an acid anhydride group, those conditions can be employed as appropriate. For example, it is possible to appropriately utilize such a condition that is employed for a known reaction which enables formation of an acid anhydride group.

In addition, in such a heating step, for the purpose of enabling heating in the lower carboxylic acid, it is preferable to first prepare a mixture of the lower carboxylic acid, the carbonyl compound, and the acid catalyst. A method for preparing such a mixture is not particularly limited. Preparation may be performed as appropriate depending on an apparatus and the like for utilization in the heating step. For example, preparation may be performed by adding (introducing) them into the same container.

In addition, in such a heating step, another solvent may be further utilized by being added to the lower carboxylic acid. Examples of the solvent (another solvent) include aromatic solvents such as benzene, toluene, xylene, and chlorobenzene; ether-based solvent such as ether, THF, and dioxane; ester-based solvents such as ethyl acetate; hydrocarbon-based solvents such as hexane, cyclohexane, heptane, and pentane; nitrile-based solvents such as acetonitrile and benzonitrile; halogen-containing solvents such as methylene chloride and chloroform; ketone-based solvents such as acetone and MEK; and amide-based solvents such as DMF, NMP, DMI, and DMAc.

In addition, the temperature condition under which the carbonyl compound (raw material compound) of the present invention is heated in the lower carboxylic acid is not particularly limited, and the upper limit of the heating temperature is preferably 180° C. (more preferably 150° C., further preferably 140° C., and particularly preferably 130° C.), while the lower limit of the heating temperature is preferably 80° C. (more preferably 100° C., and further preferably 110° C.). The temperature range (temperature condition) for the heating is preferably 80 to 180° C., more preferably 80 to 150° C., further preferably 100 to 140° C., and particularly preferably 110 to 130° C. If the temperature condition is lower than the lower limit, the reaction tends to proceed so insufficiently that the target tetracarboxylic dianhydride cannot be produced sufficiently efficiently. Meanwhile, if the temperature condition exceeds the upper limit, the catalytic activity tends to be lowered. In addition, the heating temperature is preferably set to a temperature lower than the boiling point of the homogeneous acid catalyst within the range of the above-described temperature condition. By setting the heating temperature as described above, the product can be obtained more efficiently.

In addition, the heating step may include the step of refluxing the mixture (mixture of the lower carboxylic acid, the carbonyl compound, and the acid catalyst) by heating from the viewpoint of producing the carboxylic anhydride of the present invention more efficiently. As described above, if the heating step includes the refluxing step, it is possible to produce the carboxylic anhydride more efficiently. To be more specific, in the heating step, since the reaction has not sufficiently proceeded at the first stage of heating, by-products such as water are produced in little amount. Thus, by-products (such as water) do not have a very strong influence even if a distillation component (vapor) is not removed until the reaction proceeds to some extent (at the first stage of heating), making it possible to cause the forward reaction for producing the carboxylic dianhydride to proceed efficiently. For this reason, at the first stage of heating in particular, refluxing makes it possible to cause the forward reaction to efficiently proceed by utilizing the lower carboxylic acid more efficiently. This makes it possible to more efficiently produce the carboxylic anhydride.

Here, the progress of the forward reaction can be determined by checking e.g. the amount of by-product (for example, water and an ester compound of the lower carboxylic acid) contained in the vapor. For this reason, the refluxing step may be carried out by appropriately setting the reflux time so that the reaction proceeds efficiently while checking e.g. the amount of by-product (for example, an ester compound of the lower carboxylic acid) in the vapor. Thereafter, the distillation component removal step may be carried out while performing heating. If the distillation component removal step is carried out as described above, it is possible to remove by-products (for example, an ester compound of the lower carboxylic acid and water) from the reaction system and to cause the forward reaction to proceed more efficiently. In addition, during the distillation component removal step, if the lower carboxylic acid is reduced when the distillation component (vapor) is removed by distillation as appropriate (for example, when an ester compound of the lower carboxylic acid and water are produced as by-products, the carboxylic acid is consumed, the vapor is removed by distillation, and as a result the carboxylic acid is reduced), it is preferable to perform heating by appropriately adding (sometimes continuously adding) the lower carboxylic acid in an amount reduced by the removal by distillation. As described above, by adding (sometimes continuously adding) the lower carboxylic acid, it is possible to cause the forward reaction to proceed further efficiently if, for example, the carbonyl compound is e.g. a compound in which any of $R^4$s in the formula is a group other than a hydrogen atom. In addition, if such a heating step includes the step of refluxing the mixture, the condition for the reflux is not particularly limited, can employ as appropriate a known condition, and can be changed as appropriate to a preferable condition depending on the type and the like of the carbonyl compound (raw material compound) to be used.

In addition, the pressure condition for heating the carbonyl compound (raw material compound) of the present invention in the lower carboxylic acid (the pressure condition during the reaction) is not particularly limited. The condition may be normal pressure, a pressurized condition, or a reduced pressure condition, and the reaction can be caused to proceed under any one of these conditions. For this reason, when, for example, the aforementioned refluxing step is employed without particularly controlling the pressure in the heating step, for example, the reaction may be conducted under a pressurized condition by the vapor of the lower carboxylic acid serving as the solvent, or the like. In addition, the pressure condition is preferably 0.001 to 10 MPa, and further preferably 0.1 to 1.0 MPa. If the pressure condition is lower than the lower limit, the lower carboxylic acid tends to be gasified. Meanwhile, if the pressure condition exceeds the upper limit, an ester compound of the lower carboxylic acid produced by the reaction by heating tends not to evaporate, so that it is difficult to cause the forward reaction to proceed.

In addition, an atmospheric gas in which the carbonyl compound (raw material compound) of the present invention is heated in the lower carboxylic acid is not particularly limited, and may be, for example, air or an inert gas (nitrogen, argon, or the like). Note that, to cause the reaction to proceed more efficiently (to shift the transesterification equilibrium reaction more to the product side) by efficiently evaporating by-products (an ester compound of the lower carboxylic acid and water) formed by the reaction, the gas (desirably, an inert gas such as nitrogen or argon) may be bubbled, or stirring may be conducted, while the gas is being passed through the gas phase portion of a reactor (reaction vessel).

In addition, the heating time for which the carbonyl compound (raw material compound) of the present invention is heated in the lower carboxylic acid is not particularly limited, and is preferably 0.5 to 100 hours, and more preferably 1 to 50 hours. If the heating time is less than the lower limit, the reaction tends to proceed so insufficiently that a sufficient amount of the carboxylic anhydride cannot be produced. Meanwhile, if the heating time exceeds the upper limit, the reaction tends not to proceed any further, so that the production efficiency is lowered, and the economical efficiency and the like are lowered.

In addition, when the carbonyl compound (raw material compound) of the present invention is heated in the lower carboxylic acid, the reaction may be caused to proceed while the lower carboxylic acid into which the carbonyl compound is introduced (more preferably the mixture of the lower carboxylic acid, the carbonyl compound, and the acid catalyst) is being stirred from the viewpoint that the reaction is caused to proceed uniformly.

Moreover, in the step of heating the carbonyl compound (raw material compound) of the present invention in the lower carboxylic acid (heating step), it is preferable to utilize an acetic anhydride together with the lower carboxylic acid. The use of acetic anhydride as described above makes it possible to form acetic acid by a reaction of water produced during the reaction with the acetic anhydride, so that water produced during the reaction can be removed efficiently, making it possible to cause the forward reaction to proceed more efficiently. In addition, when acetic anhydride is used as described above, the amount of the acetic anhydride used is not particularly limited, and is preferably such that the amount of moles of the acetic anhydride used is 4 to 100 times that of the carbonyl compound (raw material compound) of the present invention. If the amount of the acetic anhydride used is less than the lower limit, the reaction rate tends to be lowered. Meanwhile, if the amount of the acetic anhydride exceeds the upper limit, the yield tends to decrease.

In addition, also when an acetic anhydride is utilized as described above, it is preferable to employ the conditions described in the aforementioned heating step as conditions and the like such as the temperature condition, the pressure condition, the atmospheric gas condition, and the heating time during heating. In addition, the use of acetic anhydride as described above makes it possible not only to form acetic acid by a reaction of water produced during the reaction with the acetic anhydride, so that water produced during the reaction can be removed efficiently without e.g. removing the vapor by distillation, but also to cause a reaction in which acetic acid is formed from acetic anhydride and water to produce the tetracarboxylic dianhydride (forward reaction) to proceed more efficiently. For this reason, if an acetic anhydride is utilized as described above, it is possible to cause the reaction to proceed efficiently by employing the refluxing step in the heating step. From such a viewpoint, if an acetic anhydride is utilized, the heating step is preferably the step of refluxing the mixture. As described above, if the reflux is carried out by utilizing an acetic anhydride, it is possible to cause the reaction to proceed sufficiently only by carrying out the refluxing step without carrying out a step such as removing the vapor by distillation or adding the lower carboxylic acid depending on the amount used, making it possible to produce the tetracarboxylic dianhydride more efficiently.

Such a heating step makes it possible to efficiently obtain the tetracarboxylic dianhydride of the present invention from the carbonyl compound (raw material compound) of the present invention. Specifically, the use of carbonyl compound (raw material compound) of the present invention makes it possible to efficiently obtain a tetracarboxylic dianhydride of the present invention in which the content of the acid dianhydride (B) in the total amount of the acid dianhydrides (A) and (B) is 30 to 100% by mole in a mole ratio. Note that, from the viewpoint of increasing the content of the acid dianhydride (B) in the obtained tetracarboxylic dianhydride, recrystallization may be carried out in a solution adjusted to a predetermined concentration by the addition of a solvent to the obtained tetracarboxylic dianhydride because it is possible to separate the acid dianhydride (A) and the acid dianhydride (B) to some extent (increase the ratio of one of them) by using a characteristic that the acid dianhydride (B) is easily precipitated by the crystallization. On the other hand, from the viewpoint of increasing the content of the acid dianhydride (A) after obtaining the tetracarboxylic dianhydride, the tetracarboxylic dianhydride may be washed with a solvent followed by drying of the washing liquid for solidification because it is possible to separate the acid dianhydride (A) and the acid dianhydride (B) to some extent (increase the ratio of one of them) by using a characteristic that the acid dianhydride (B) is hardly dissolved into a solvent. As described above, even after preparing the tetracarboxylic dianhydride, it is possible to appropriately change the content ratios of the acid dianhydrides (A) and (B).

[Polyimide]

A polyimide of the present invention comprises: at least one repeating unit (A) selected from the group consisting of structural units (repeating units) each having an endo/exo type three-dimensional structure represented by the general formula (5) and their enantiomeric structural units (repeating units) each having an exo/endo type three-dimensional structure; and/or a repeating unit (B) having an endo/endo type three-dimensional structure represented by the general formula (6), wherein a content of the repeating unit (B) in a total amount of the repeating units (A) and (B) is 30 to 100% by mole in a mole ratio.

$R^1$s, $R^2$, and $R^3$ in the general formulae (5) and (6) are the same as $R^1$s, $R^2$, and $R^3$ in the general formula (1), and preferred ones thereof are also the same as $R^1$s, $R^2$, and $R^3$ in the general formula (1). Note that multiple $R^1$s in the general formulae (5) and (6) may be the same as one another or different from one another, and are preferably the same from the viewpoint of ease of purification and the like. Moreover, $R^2$ and $R^3$ in the general formulae (5) and (6) may be the same as each other or different from each other, and are preferably the same from the viewpoint of ease of purification and the like.

In addition, an arylene group which may be selected as $R^5$ in the general formulae (5) and (6) is an arylene group having 6 to 40 carbon atoms. In addition, the number of carbon atoms of such an arylene group is preferably 6 to 30 and more preferably 12 to 20. If the number of carbon atoms is less than the lower limit, the heat resistance of a polyimide tends to be lowered. Meanwhile, if the number of carbon atoms exceeds the upper limit, the solubility of the obtained polyimide to the solvent is lowered, and formability to a film and the like tend to be lowered.

In addition, $R^5$ in the general formulae (5) and (6) is preferably at least one of the groups represented by the following general formulae (i) to (iv):

[Chem. 13]

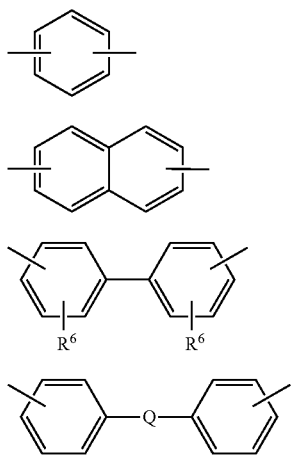

[in the formula (iii), $R^6$ is one selected form the group consisting of a hydrogen atom, a fluorine atom, methyl groups, ethyl groups, and trifluoromethyl groups, and in the formula (iv), Q represents one selected from the group consisting of the groups represented by the formulae: —$C_6H_4$—, —CONH—$C_6H_4$—NHCO—, —NHCO—$C_6H_4$—CONH—, —O—$C_6H_4$—CO—$C_6H_4$—O—, —OCO—$C_6H_4$—COO—, —OCO—$C_6H_4$—$C_6H_4$—COO—, —OCO—, —$NC_6H_5$—, —CO—$C_4H_8N_2$—CO—, —$C_{13}H_{10}$—, —O—, —S—, —CO—, —CONH—, —$SO_2$—, —$C(CF_3)_2$—, —$C(CH_3)_2$—, —$CH_2$—$(CH_2)_2$—, —$(CH_2)_3$—, —$(CH_2)_4$—, —$(CH_2)_5$—, —O—$C_6H_4$—C$(CH_3)_2$—$C_6H_4$—O—, —O—$C_6H_4$—$SO_2$—$C_6H_4$—O—, —$C(CH_3)_2$—$C_6H_4$—$C(CH_3)_2$—, —O—$C_6H_4$—$C_6H_4$—O—, and —O—$C_6H_4$—O—] from the viewpoint of the balance between the heat resistance and the solubility.

$R^6$ in the general formula (iii) is more preferably a hydrogen atom, a fluorine atom, a methyl group, or an ethyl group, and particularly preferably a hydrogen atom from the viewpoint of the heat resistance of the obtained polyimide. In addition, Q in the general formula (iv) is preferably a group represented by the formula: —CONH—, —O—$C_6H_4$—O—, —O—$C_6H_4$—$C_6H_4$—O—, —O—, —$C(CH_3)_2$—, —$CH_2$—, or —O—$C_6H_4$—$C(CH_3)_2$—$C_6H_4$—O—, particularly preferably a group represented by the formula: —CONH—, —O—$C_6H_4$—$C(CH_3)_2$—$C_6H_4$—O—, or —O—, and most preferably a group represented by the formula: —O—$C_6H_4$—$C(CH_3)_2$—$C_6H_4$—O— or —O— from the viewpoint of the balance between the heat resistance and the solubility.

In addition, a group, which may be selected as $R^5$ in the general formulae (5) and (6) and is represented by the general formulae (i) to (iv), is more preferably a group represented by the general formula (iii) or (iv) from the viewpoint that they can provide a sufficiently high temperature of glass transition temperature and a sufficiently low value of linear expansion coefficient, and thus the balance between these characteristics are improved and higher heat resistance can be obtained. Among these, $R^5$ is preferably at least one of a group represented by the general formula (iii) and a group represented by the general formula (iv) in which the Q is represented by —CONH—, —COO—, —CO—, or —$C_6H_4$— (more preferably a group represented by —CONH— or —COO— and particularly preferably a group represented by —CONH—) from the viewpoint that they can provide a lower linear expansion coefficient and an even higher heat resistance. Furthermore, $R^5$ in the general formulae (5) and (6) is preferably a group represented by the general formula (i) or a group represented by the general formula (iv) in which the Q is at least one of the groups represented by —O—, —S—, —$CH_2$—, and —O—$C_6H_4$—O— (more preferably one of the groups represented by —O— and —$CH_2$— and further preferably a group represented by —O—) from the viewpoint that they can provide the obtained polyimide with a higher flexible property (flexibility).

Moreover, the polyimide preferably contains several types (two or more types) of repeating unit with different types of $R^5$ in the general formulae (5) and (6) from the viewpoint that they have a sufficiently high glass transition temperature, a sufficiently low linear expansion coefficient, and a sufficient flexible property (flexibility) in balance at an even higher level. In addition, from the same viewpoint, since a higher effect can be obtained, the polyimide containing the several types of repeating unit is more preferably one which contains a repeating unit (X) in which $R^5$ in the formula is one selected from the group consisting of a group represented by the general formula (iii); and a group represented by the general formula (iv) in which the Q is one of the groups represented by —CONH—, —COO—, —CO—, and —$C_6H_4$— (more preferably the groups represented by —CONH— and —COO— and particularly preferably the group represented by —CONH—) and a repeating unit (Y) in which $R^5$ in the formula is one selected from the group consisting of a group represented by the general formula (i); and a group represented by the general formula (iv) in which the Q is one of the groups represented by —O—, —S—, —$CH_2$—, and —O—$C_6H_4$—O— (more preferably one of the groups represented by —O— and —$CH_2$— and further preferably the group represented by —O—).

In addition, such a repeating unit (Y) is more preferably one in which $R^5$ in the formula is a group represented by the general formula (iv) and Q in the formula (iv) is one of the groups represented by —O—, —$CH_2$—, and —O—$C_6H_4$—O— (more preferably one of the groups represented by —O— and —$CH_2$— and further preferably the group represented by —O—) from the viewpoint of how easily the monomer is obtained in the production.

If such repeating units (X) and (Y) are contained, the content ratio between the repeating unit (X) and the repeating unit (Y) is preferably 9:1 to 6:4 (more preferably 8:2 to 7:3) in a mole ratio ((X):(Y)). If the content ratio of the repeating unit (X) is less than the lower limit, it tends to be difficult to obtain a polyimide with a lower linear expansion coefficient. Meanwhile, if the content ratio of the repeating unit (X) exceeds the upper limit, the flexible property of the obtained board film tends to be lowered. In addition, if the repeating units (X) and (Y) are contained, it is preferable that the configurations of the substituents other than $R^5$ in the general formulae (5) and (6) be the same from the viewpoint that it is possible to prepare the polyimide more efficiently.

Note that the repeating unit (A) may be one containing a structural unit (repeating unit) alone having an endo/exo type three-dimensional structure, may be one containing a structural unit (repeating unit) alone having an exo/endo type three-dimensional structure, or may be one containing both of them.

In addition, the polyimide of the present invention comprises: at least one repeating unit (A) selected from the group consisting of structural units (repeating units) each having an endo/exo type three-dimensional structure represented by the general formula (5) and their enantiomeric structural units (repeating units) each having an exo/endo type three-dimensional structure; and/or a repeating unit (B) having an endo/endo type three-dimensional structure represented by the following general formula (6), wherein a content of the repeating unit (B) in a total amount of the repeating units (A) and (B) is 30 to 100% by mole in a mole ratio.

As described above, the content of the repeating unit (B) having an endo/endo type three-dimensional structure is 30 to 100% by mole in the total amount of moles of the repeating units (A) and (B). If the content of the repeating unit (B) is less than the lower limit, a polyimide tends to have a lowered mechanical strength based on the elongation at break. In addition, the content of the repeating unit (B) in the total amount of moles of the repeating units (A) and (B) is more preferably 40 to 100% by mole, further preferably 60 to 100% by mole, particularly preferably 80 to 100% by mole, and most preferably 90 to 100% by mole from the viewpoint of obtaining a higher mechanical strength.

In addition, the polyimide is preferably one which mainly contains the repeating unit (A) and/or the repeating unit (B) (more preferably, the total amount of the repeating units (A) and (B) is 50 to 100% by mole (further preferably 70 to 100% by mole, particularly preferably 80 to 100% by mole, and most preferably 90 to 100% by mole) in the entire repeating units in the polyimide). Note that the polyimide may contain a different repeating unit as long as the effects of the present invention are not impaired. The different repeating unit is not particularly limited, and includes a known repeating unit and the like which can be used as a repeating unit of the polyimide.

In addition, a preferable example of the different repeating unit is a repeating unit represented by the following general formula (13):

[Chem. 14]

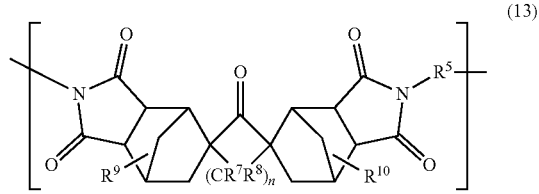

(13)

[in the formula (13), $R^7$, $R^8$, $R^9$, $R^{10}$ each independently represent one selected from the group consisting of a hydrogen atom, alkyl groups having 1 to 10 carbon atoms, and a fluorine atom, $R^5$ represents an aryl group having 6 to 40 carbon atoms, and n represents an integer from 0 to 12].

Note that $R^7$, $R^8$, $R^9$, and $R^{10}$ in the general formula (13) each independently are one selected from the group consisting of a hydrogen atom, alkyl groups having 1 to 10 carbon atoms, and a fluorine atom. The alkyl groups having 1 to 10 carbon atoms which may be selected as $R^7$, $R^8$, $R^9$, and $R^{10}$ are the same as the alkyl group which may be selected as $R^1$ in the general formula (1) (preferred ones thereof are also the same). $R^7$, $R^8$, $R^9$, and $R^{10}$ in the formula (13) are each independently more preferably a hydrogen atom or an alkyl group having 1 to 10 carbon atoms from the viewpoint of the adhesiveness of the obtained polyimide. Among these, $R^7$, $R^8$, $R^9$, and $R^{10}$ in the formula (13) are each independently more preferably a hydrogen atom, a methyl group, an ethyl group, an n-propyl group, or an isopropyl group, and particularly preferably a hydrogen atom or a methyl group from the viewpoint that the raw material is readily available and that the purification is easier. In addition, $R^7$, $R^8$, $R^9$, and $R^{10}$ in the formula are particularly preferably the same as one another from the viewpoint of ease of purification and the like. In addition, $R^5$ in the general formula (13) is the same as $R^5$ in the general formulae (5) and (6) (preferred ones thereof are also the same). In addition, n in the general formula (13) represents an integer from 0 to 12. If the value of n exceeds the upper limit, purification is difficult. In addition, the upper limit value of the numerical range of n in the general formula (13) is more preferably 5 and particularly preferably 3 from the viewpoint that the purification is easier. In addition, the lower limit value of the numerical range of n in the general formula (13) is more preferably 1 and particularly preferably 2 from the viewpoint of stability of the raw material compound. As described above, n in the general formula (13) is particularly preferably an integer of 2 or 3.

In addition, the different repeating unit (including the repeating unit represented by the general formula (13) and the like) can be easily introduced by e.g. using the tetracarboxylic dianhydride of the present invention as well as another tetracarboxylic dianhydride in the production of the polyimide. In this case, the different repeating unit is derived from the other tetracarboxylic dianhydride other than the tetracarboxylic dianhydride of the present invention. Note that the other tetracarboxylic dianhydride is described later. In addition, if the different repeating unit is contained, the mole ratio ([total amount of the repeating units represented by the general formulae (5) and (6)]:[content of the different repeating unit]) may be 99.9:0.1 to 0.1:99.9. Furthermore, in the case where the different repeating unit is contained, the ratio between the total amount of the repeating units represented by the general formulae (5) and (6) and the content of the different repeating unit is preferably 9:1 to 5:5 (more preferably 9:1 to 7:3) in a mole ratio ([total amount of the repeating units represented by the general formulae (5) and (6)]:[content of the different repeating unit]) from the viewpoint of the balance between the heat resistance and the transparency.

The polyimide of the present invention is one having a 5% weight-loss temperature of preferably 350° C. or higher, and more preferably 450 to 550° C. If the 5% weight-loss temperature is lower than the lower limit, it tends to be difficult to achieve a sufficient heat resistance. Meanwhile, if the 5% weight-loss temperature exceeds the upper limit, it tends to be difficult to produce a polyimide having such a property. Note that the 5% weight-loss temperature can be determined by measuring the temperature at which the weight loss of a sample used reaches 5% when the sample is raised from room temperature (25° C.) to a temperature of 40° C. under a nitrogen gas atmosphere in a nitrogen gas stream, and heated under a condition of 10° C./min with a starting temperature of 40° C. Note that in the measurement, the mass of the sample used is preferably 1.0 mg to 10 mg (more preferably 1.5 mg to 4.0 mg). If the mass of the sample is within the aforementioned range, it is possible to measure the same value for the same polyimide even if the measurement is carried out for a different mass of the sample.

In addition, the polyimide is one having a glass transition temperature (Tg) of preferably 200° C. or higher, more preferably 230 to 500° C., and particularly preferably 250 to 500° C. If the glass transition temperature (Tg) is lower than the lower limit, it tends to be difficult to achieve a sufficient heat resistance. Meanwhile, if the glass transition temperature (Tg) exceeds the upper limit, it tends to be difficult to produce a polyimide having such a property. Note that the glass transition temperature (Tg) can be determined by using a thermomechanical analyzer (manufactured by Rigaku Corporation under the trade name of "TMA 8310").

Moreover, the polyimide has a softening temperature of preferably 300° C. or higher, and more preferably 350 to 550° C. If the softening temperature is lower than the lower limit, it tends to be difficult to achieve a sufficient heat resistance. Meanwhile, if the softening temperature exceeds the upper limit, it tends to be difficult to produce a polyimide having such a property. Note that the softening temperature can be determined by using a thermomechanical analyzer (manufactured by Rigaku Corporation under the trade name of "TMA 8310") in a penetration mode. In addition, in the measurement, since the size (length, width, thickness, and the like) of the sample does not affect the measurement value, the size of the sample may be adjusted as appropriate to a size attachable to a jig of the thermomechanical analyzer to be used (manufactured by Rigaku Corporation under the trade name of "TMA 8310").

In addition, the polyimide has a thermal decomposition temperature (Td) of preferably 400° C. or higher, and more preferably 450 to 600° C. If the thermal decomposition temperature (Td) is lower than the lower limit, it tends to be difficult to achieve a sufficient heat resistance. Meanwhile, if the thermal decomposition temperature (Td) exceeds the upper limit, it tends to be difficult to produce a polyimide having such a property. Note that the thermal decomposition temperature (Td) can be determined by measuring the temperature at an intersection of tangent lines drawn to decomposition curves before and after thermal decomposition using a TG/DTA220 thermogravimetric analyzer (manufactured by SII NanoTechnology Inc.) under a nitrogen atmosphere under a condition of a rate of temperature rise of 10° C./min. Note that in the measurement, the mass of the sample used is preferably 1.0 to 10 mg (more preferably 5 mg to 10 mg). If the mass of the sample is within the aforementioned range, it is possible to measure the same value for the same polyimide even if the measurement is carried out for a different mass of the sample. Furthermore, the thermal decomposition temperature (Td) can be measured at the same time under the same conditions (under a nitrogen atmosphere under a condition of a rate of temperature rise of 10° C./min) by using the same apparatus as in the measurement of the 5% weight-loss temperature.

Moreover, the polyimide preferably has a number average molecular weight (Mn) of 1000 to 1000000 in terms of polystyrene. If the number average molecular weight is less than the lower limit, it tends to be difficult to achieve a sufficient heat resistance. Meanwhile, if the number average molecular weight exceeds the upper limit, the polyimide tends to be difficult to process.

In addition, the polyimide preferably has a weight average molecular weight (Mw) of 1000 to 5000000 in terms of polystyrene. If the weight average molecular weight is less than the lower limit, it tends to be difficult to achieve a sufficient heat resistance. Meanwhile, if the weight average molecular weight exceeds the upper limit, the polyimide tends to be difficult to process.

Moreover, the polyimide preferably has a molecular weight distribution (Mw/Mn) of 1.1 to 5.0. If the molecular weight distribution is less than the lower limit, the polyimide tends to be difficult to produce. Meanwhile, if the molecular weight distribution exceeds the upper limit, it tends to be difficult to produce a uniform film. Note that the molecular weights (Mw and Mn) of the polyimide and the distribution (Mw/Mn) of the molecular weights can be determined by using a gel permeation chromatograph as a measuring apparatus and converting the measured data to that of polystyrene.

Note that when the molecular weight of a polyimide is difficult to measure, a polyimide may be selected and used according to the application or the like by estimating the molecular weight and the like on the basis of the viscosity of a polyamic acid used for producing the polyimide.

In addition, the polyimide is one having a total luminous transmittance of more preferably 80% or higher (further preferably 85% or higher and particularly preferably 87% or higher) from the viewpoint of obtaining a higher transparency. In addition, the polyimide is one having a haze (turbidity) of more preferably 5 to 0 (further preferably 4 to 0 and particularly preferably 3 to 0) from the viewpoint of obtaining a higher transparency. Furthermore, the polyimide is one having a yellowness index (YI) of more preferably 5 to 0 (further preferably 4 to 0 and particularly preferably 3 to 0) from the viewpoint of obtaining a higher transparency. Such a total luminous transmittance, haze (turbidity), and yellowness index (YI) can be achieved easily by selecting, as appropriate, the type of the polyimide and the like. Note that values measured as follows can be employed as the total luminous transmittance and the haze (turbidity). Specifically, a measuring apparatus manufactured by NIPPON DENSHOKU INDUSTRIES CO., LTD. under the trade name of "Haze Meter NDH-5000" was used to measure a film comprising a polyimide having a thickness of 5 to 80 μm prepared as a sample for measurement. In addition, a value measured as follows can be employed as the yellowness index. Specifically, a measuring apparatus manufactured by NIPPON DENSHOKU INDUSTRIES CO., LTD. under the trade name of "Spectrophotometer SD6000" was used to measure a film comprising a polyimide having a thickness of 5 to 80 μm prepared as a sample for measurement. Note that it is possible to measure the same value for each of the total luminous transmittance, the haze (turbidity), and the yellowness index (YI) for the same polyimide if the film comprises a polyimide having a thickness of 5 to 80 μm because the thickness is sufficiently thin and thus does not affect the measurement values. For this reason, in the measurement of the total luminous transmittance, the haze (turbidity), and the yellowness index (YI), it suffices to use a film having a thickness within the range. In addition, the sizes in length and width of the measurement sample may be such sizes that can be disposed at a measurement position of the measuring apparatus. The sizes in length and width may be changed as appropriate. Note that the total luminous transmittance is obtained by performing measurement in accordance with JIS K7361-1 (issued in 1997), the haze (turbidity) is obtained by performing measurement in accordance with JIS K7136 (issued in 2000), and the yellowness index (YI) is obtained by performing measurement in accordance with ASTM E313-05 (issued in 2005).

In addition, the polyimide has a linear expansion coefficient of preferably 0 to 100 ppm/K, and more preferably 10 to 80 ppm/K. If the linear expansion coefficient exceeds the upper limit, the polyimide tends to be easily peeled off because of thermal history when a composite material is formed by combining the polyimide with a metal or an inorganic material having a linear expansion coefficient in a range from 5 to 20 ppm/K. Meanwhile, if the linear expansion coefficient is lower than the lower limit, the solubility tends to be lowered, and film characteristics tend to deteriorate.

A method for measuring the linear expansion coefficient of the polyimide is as follows. Specifically, a measurement sample is prepared by forming a polyimide film in a size of 20 mm in length and 5 mm in width (although the thickness of the film is not particularly limited because it does not affect the measurement value, it is preferably 10 to 30 μm). Then, the change in length of the sample in the longitudinal direction is measured from 50° C. to 200° C. by using a thermomechanical analyzer (manufactured by Rigaku Corporation under the trade name of "TMA 8310") as a measuring apparatus and by employing a condition of a rate of temperature rise of 5° C./minute under a nitrogen atmosphere in a tensile mode (49 mN). The average value of changes in length per Celsius degree is determined for the temperature range from 100° C. to 200° C. The thus obtained value is employed as the linear expansion coefficient.

The polyimide has an elongation at break of preferably 10% or more. If the elongation at break is less than the lower limit, there is a tendency that the toughness is low and mechanically brittle. The elongation at break can be measured in accordance with the method described in "JIS K7161" of the Japanese Industrial Standards.

The shape of the polyimide is not particularly limited, and may be, for example, the shape of a film, the form of powder, moreover the shape of a pellet by extrusion molding, and the like. As described above, the polyimide of the present invention can be formed into various shapes as appropriate by a known method such as in the shape of a film and in the shape of a pellet by extrusion molding.

When the polyimide of the present invention is formed into a film shape, the form of the film (polyimide film) is not particularly limited, as long as the form is in a film shape, and the polyimide film may be designed to have any of various shapes (a circular disc shape, a cylindrical shape (a film processed into a tube), or the like), as appropriate. The thickness of the polyimide film (film comprising the polyimide of the present invention) is not particularly limited, and preferably 1 to 500 μm, and more preferably 5 to 200 μm. If the thickness is less than the lower limit, the strength tends to decrease, making the film difficult to handle. Meanwhile, if the thickness exceeds the upper limit, it tends to be necessary to perform application multiple times, or the process tends to be complicated.

In addition, the polyimide of the present invention has a sufficiently high transparency and a higher heat resistance. Note that, although it is not exactly clear why the polyimide of the present invention exhibits a sufficiently high heat resistance and transparency, the present inventors speculate as follows. Specifically, first, regarding the heat resistance, the sufficiently high heat resistance is achieved because the repeating unit of the polyimide of the present invention has a rigid alicyclic structure, and hence the polyimide has a chemically sufficiently stable structure, increasing the heat resistance based on the 5% weight-loss temperature. Note that the present inventors speculate as follows. The polyimide forms a first-order structure in which an acid dianhydride having a rigid alicyclic structure and an aromatic diamine are bonded to each other, and the energy gap between the HOMO orbital and the LUMO orbital is large between the acid dianhydride moiety and the aromatic diamine moiety, making it less likely for electron transfer between molecular chains of the polyimide to occur. Thus, the polyimide has a very high transparency.

In addition, the applications to which the polyimide of the present invention can be used are not particularly limited, and the polyimide of the present invention can be appropriately applied to known applications to which polyimides can be used. In addition, the polyimide of the present invention is especially useful as a material for producing films for flexible wiring boards, heat-resistant insulating tapes, enameled wires, coating agents for semiconductors (for example, protective coating agents for semiconductors), liquid crystal orientation films, transparent electrically conductive films for organic ELs, films for organic EL lighting devices, flexible substrate films, substrate films for flexible organic ELs, front films for flexible displays, back films for flexible displays, polyimide belts, coating agents, barrier films, sealants, interlayer insulating materials, passivation films, TAB (Tape Automated Bonding) tapes, optical waveguides, flexible transparent electrically conductive films, transparent electrically conductive films for organic thin film-type solar cells, transparent electrically conductive films for dye-sensitized-type solar cells, flexible gas barrier films, films for touch panels, seamless polyimide belts (so-called transfer belts) for copiers, transparent electrode substrates (transparent electrode substrates for organic ELs, transparent electrode substrates for solar cells, transparent electrode substrates for electronic paper, and the like), interlayer insulating films, sensor substrates, substrates for image sensors, reflectors for light-emitting diodes (LED) (reflectors for LED illumination: LED reflectors), covers for LED illumination, covers for LED reflector illumination, coverlay films, highly extensible composite substrates, resists for semiconductors, lithium-ion batteries, substrates for organic memories, substrates for organic transistors, substrates for organic semiconductors, color filter base materials, and the like because the polyimide has a sufficiently high transparency and a higher heat resistance. In addition, if the sufficiently high heat resistance is used, the polyimide can be used as appropriate in, for example, parts for automobiles, aerospace parts, bearing parts, sealing materials, bearing parts, gearwheels, valve parts, and the like in addition to the aforementioned applications by e.g. forming the shape into the form of powder and into various formed bodies. Moreover, the polyimide can have a lower value of loss tangent (tan δ) depending on the structure. For this reason, it is possible to sufficiently reduce transmission loss when the polyimide of the present invention is utilized in, for example, interlayer insulating film material for semiconductor, a board film for a flexible printed circuit board (FPC), and the like. For this reason, the polyimide of the present invention can also be preferably utilized in a high frequency band material (for example, a large-scale integration (LSI), an electronic circuit, and the like) and the like. Note that a method for producing the polyimide is described later. As above, the polyimide of the present invention is described, and a polyimide precursor resin of the present invention is hereinafter described.

[Polyimide Precursor Resin]

A polyimide precursor resin of the present invention comprises: at least one repeating unit (A') selected from the group consisting of structural units (repeating units) each having an endo/exo type three-dimensional structure represented by the general formula (7) and their enantiomeric structural units (repeating units) each having an exo/endo type three-dimensional structure; and/or a repeating unit (B') having an endo/endo type three-dimensional structure represented by the general formula (8), wherein a content of the repeating unit (B') in a total amount of the repeating units (A') and (B') is 30 to 100% by mole in a mole ratio.

Note that the polyimide precursor resin is one which enables the formation of the polyimide of the present invention by imidization of the polyimide precursor resin (by, for example, imidization followed by dehydration ring-closure if the polyimide precursor resin is a polyamic acid). A polyimide precursor resin containing the repeating unit (A') and/or (B') can be formed based on the tetracarboxylic dianhydride of the present invention and the aromatic diamine.

$R^1$s, $R^2$, $R^3$, and $R^5$ in the general formulae (7) and (8) are the same as $R^1$s, $R^2$, $R^3$, and $R^5$ in the general formulae (5) and (6). Note that multiple $R^1$s in the general formulae (7) and (8) may be the same as one another or different from one another, and are preferably the same from the viewpoint of ease of purification and the like. Moreover, $R^2$ and $R^3$ in the general formulae (7) and (8) may be the same as each other or different from each other, and are preferably the same from the viewpoint of ease of purification and the like.

In addition, in the general formulae (7) and (8), $Y^1$ and $Y^2$ are each independently any of a hydrogen atom, an alkyl group having 1 to 6 carbon atoms (preferably 1 to 3 carbon atoms), and an alkylsilyl group having 3 to 9 carbon atoms. Regarding $Y^1$ and $Y^2$, the types of the substituents and the introduction rates of the substituents can be changed by appropriately changing their production conditions. The production of polyimide tends to be easy if the $Y^1$ and $Y^2$ are each a hydrogen atom (in the case of the so-called repeating unit of the polyamic acid).

In addition, if $Y^1$ and $Y^2$ in the general formulae (7) and (8) are each an alkyl group having 1 to 6 carbon atoms (preferably 1 to 3 carbon atoms), the storage stability of the polyimide precursor resin tends to be better. In addition, if $Y^1$ and $Y^2$ are each an alkyl group having 1 to 6 carbon atoms (preferably 1 to 3 carbon atoms), $Y^1$ and $Y^2$ are each more preferably a methyl group or an ethyl group.

In addition, if $Y^1$ and $Y^2$ in the general formulae (7) and (8) are each an alkylsilyl group having 3 to 9 carbon atoms, the solubility of the polyimide precursor resin tends to be better. If $Y^1$ and $Y^2$ are each an alkylsilyl group having 3 to 9 carbon atoms as described above, $Y^1$ and $Y^2$ are each more preferably a trimethylsilyl group or a t-butyldimethylsilyl group.

Depending on the types of the substituents $Y^1$ and $Y^2$ in the repeating units, the polyimide precursor resin can be classified into 1) polyamic acid ($Y^1$ and $Y^2$ in the general formulae of the repeating units contained in the polyimide precursor resin are both hydrogen atoms), 2) polyamic acid ester (at least one of $Y^2$ and $Y^2$ is an alkyl group), 3) polyamic acid silyl ester (at least one of $Y^1$ and $Y^2$ is an alkylsilyl group), and the like. Note that the polyimide precursor resin is more preferably a polyamic acid in which all of $Y^1$ and $Y^2$ in the general formula of the repeating unit (A') and/or (B') are hydrogen atoms from the viewpoint that the preparation is easier.

Note that, if the polyimide precursor resin is a polyamic acid, the polyamic acid has an intrinsic viscosity [η] of preferably 0.05 to 3.0 dL/g, and more preferably 0.1 to 2.0 dL/g. If the intrinsic viscosity [η] is lower than 0.05 dL/g, the obtained film tends to be brittle, when a polyimide in the form of a film is produced by using this polyamic acid. Meanwhile, if the intrinsic viscosity [η] exceeds 3.0 dL/g, the viscosity is so high that the processability decreases, for example, making it difficult to form a uniform film when a film is produced. In addition, in the present invention, the intrinsic viscosity [η] employed is a value determined as follows. Specifically, first, N,N-dimethylacetamide is used as a solvent, and the polyamic acid is dissolved in the N,N-dimethylacetamide at a concentration of 0.5 g/dL to obtain a measurement sample (solution). Next, by using the measurement sample, the viscosity of the measurement sample is measured by using a kinematic viscometer under a temperature condition of 30° C., and the determined value is employed as the intrinsic viscosity [η]. Note that, as the kinematic viscometer, an automatic viscometer manufactured by RIGO CO., LTD. (trade name: "VMC-252") is used.

In addition, if groups other than hydrogen atoms (alkyl groups and/or alkylsilyl groups) are introduced as $Y^1$ and $Y^2$ in the general formulae (7) and (8), their introduction rates (rates of $Y^1$ and $Y^2$ being groups other than hydrogen atoms based on the total amount of $Y^1$ and $Y^2$) are not particularly limited. However, if at least one of $Y^1$ and $Y^2$ is an alkyl group and/or alkylsilyl group, the alkyl group and/or the alkylsilyl group is preferably 25% or more (more preferably 50% or more and further preferably 75% or more) in the total amount of $Y^1$ and $Y^2$ (note that, in this case, $Y^1$ and $Y^2$ other than an alkyl group and/or an alkylsilyl group are hydrogen atoms). If the alkyl group and/or the alkylsilyl group is 25% or more in the total amount of $Y^1$ and $Y^2$, the storage stability of the polyimide precursor tends to be better.

In addition, in the polyimide precursor resin (more preferably a polyamic acid) of the present invention, the content of the repeating unit (B') having an endo/endo type three-dimensional structure is 30 to 100% by mole in the total amount of moles of the repeating units (A') and (B'). If the content of the repeating unit (B') is less than the lower limit, a polyimide produced by using that repeating unit tends to have a lowered mechanical strength based on the elongation at break. In addition, the content of the repeating unit (B') in the total amount of moles of the repeating units (A') and (B') is more preferably 40 to 100% by mole, further preferably 60 to 100% by mole, particularly preferably 80 to 100% by mole, and most preferably 90 to 100% by mole from the viewpoint of obtaining a higher mechanical strength.

In addition, the polyimide precursor resin (more preferably a polyamic acid) of the present invention is more preferably one mainly containing a repeating unit composed of the repeating unit (A') and/or the repeating unit (B') (further preferably, the total amount of the repeating unit (A') and the repeating unit (B') is 50 to 100% by mole in the entire repeating units). In addition, in the polyimide precursor resin (more preferably a polyamic acid) of the present invention, the total amount of the repeating unit (A') and the repeating unit (B') is preferably 90% by mole or more, more preferably 95 to 100% by mole, and further preferably 98 to 100% by mole in the entire repeating units contained in the polyimide precursor resin (more preferably a polyamic acid). If the total amount of the repeating unit (A') and the repeating unit (B') is less than the lower limit, the balance of the transparency, high heat resistance, and low loss tangent (tan δ) of the polyimide tends to be lost.

Note that the polyimide precursor resin (more preferably a polyamic acid) may contain a different repeating unit other than the repeating unit (A') and the repeating unit (B') as long as the effects of the present invention are not impaired. The different repeating unit is not particularly limited, and includes a known repeating unit and the like which can be used as a polyimide precursor resin (more preferably a repeating unit of a polyamic acid). Examples thereof include repeating units derived from other tetracarboxylic dianhydrides other than the tetracarboxylic dianhydride of the present invention, and the like. A preferable example of the different repeating unit which may be contained in the polyamic acid is a repeating unit represented by the following general formula (14):

[Chem. 15]

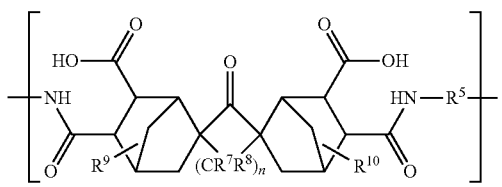

(14)

[$R^5$, $R^7$, $R^8$, $R^9$, $R^{10}$, and n in the general formula (14) have the same meanings as those of $R^5$, $R^7$, $R^8$, $R^9$, $R^{10}$, and n in the general formula (13), respectively (preferred ones thereof are also the same)]. Note that the different repeating unit may be a repeating unit in which, in the repeating unit represented by the general formula (14), one or both of the two groups represented by the formula: —OH are substituted with groups represented by the formula: —$OY^3$ (Here, $Y^3$ represents an alkyl group having 1 to 6 carbon atoms (preferably 1 to 3 carbon atoms) or an alkylsilyl group having 3 to 9 carbon atoms. Note that the alkyl group having 1 to 6 carbon atoms (preferably 1 to 3 carbon atoms) and the alkylsilyl group having 3 to 9 carbon atoms as $Y^3$ have the same meanings as those of the alkyl group having 1 to 6 carbon atoms (preferably 1 to 3 carbon atoms) and the alkylsilyl group having 3 to 9 carbon atoms described for $Y^1$ in the general formulae (7) and (8), and preferred ones thereof are also the same).

If the different repeating unit is contained, the mole ratio ([total amount of the repeating units represented by the general formulae (7) and (8)]:[different repeating unit]) may be 99.9:0.1 to 0.1:99.9. Furthermore, in the case where the different repeating unit is contained, the ratio between the total amount of the repeating units represented by 5) and (8) and the content of the different repeating unit is preferably 9:1 to 5:5 (more preferably 9:1 to 7:3) in a mole ratio ([total amount of the repeating unit represented by the general formula (7)]:[content of the different repeating unit]) from the viewpoints of the heat resistance and transparency of the obtained polyimide.

The polyimide precursor resin (more preferably a polyamic acid) may be dissolved into an organic solvent to form a polyimide precursor resin solution (varnish). As the organic solvent used for the polyimide precursor resin solution (resin solution containing the polyimide precursor resin (more preferably a polyamic acid) of the present invention and the organic solvent), it is possible to prefer-ably use one same as the organic solvents used for producing a polyimide precursor resin to be described later. For this reason, the polyimide precursor resin solution may be prepared by conducting a method for producing a polyimide precursor resin to be described later and employing the reaction liquid obtained after the reaction directly as the polyimide precursor resin solution.

The content of the polyimide precursor resin in the polyimide precursor resin solution is not particularly limited, and is preferably 1 to 80% by mass, and more preferably 5 to 50% by mass. If the content is less than the lower limit, it tends to be difficult to produce a polyimide film. Meanwhile, if the content exceeds the upper limit, it likewise tends to be difficult to produce a polyimide film. Note that the polyimide precursor resin solution can be used preferably for producing the above-described polyimide of the present invention and can be used preferably for producing polyimides with various shapes. For example, a polyimide with the shape of a film is easily produced by applying the polyimide precursor resin solution onto various substrates and curing the resultant by imidization.

(Method for Producing Polyimide Precursor Resin of Present Invention)

A method which can be preferably employed as a method for producing a polyimide precursor resin of the present invention will be described. Note that, depending on the types of $Y^1$ and $Y^2$, the polyimide precursor resin can be classified into 1) polyamic acid ($Y^1$ and $Y^2$ in the general formulae of the repeating units are both hydrogen atoms); 2) polyamic acid ester (at least one of $Y^1$ and $Y^2$ is an alkyl group); and 3) polyamic acid silyl ester (at least one of $Y^1$ and $Y^2$ is an alkylsilyl group). Since preferable production methods differ depending on the class, methods for producing a polyimide precursor will hereinafter be briefly described separately based on the classes. Note that the method for producing a polyimide precursor is not limited to the following production methods.

1) Method Which Can Be Preferably Used for Producing Polyamic Acid

A method which can be preferably used for producing the polyamic acid is a method including reacting the tetracarboxylic dianhydride of the present invention with an aromatic diamine represented by the following formula (15):

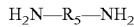 (15)

[in the formula (15), $R^5$ represents an arylene group having 6 to 40 carbon atoms] in the presence of an organic solvent, to thereby obtain a polyamic acid (polyamic acid preferable as the polyimide precursor resin of the present invention) comprising:

the at least one repeating unit (A') selected from the group consisting of structural units (repeating units) each having an endo/exo type three-dimensional structure represented by the general formula (7) and containing hydrogen atoms as both $Y^1$ and $Y^2$ in the formula, and their enantiomeric structural units (repeating units) each having an exo/endo type three-dimensional structure; and/or the repeating unit (B') represented by the general formula (8) and containing hydrogen atoms as both $Y^1$ and $Y^2$ in the formula, wherein the content of the repeating unit (B') in the total amount of the repeating units (A') and (B') is 30 to 100% by mole in a mole ratio. Specifically, the method for producing a polyamic acid is a method including a step (hereinafter, the step is sometimes simply referred to as the "step (I)") of reacting the tetracarboxylic dianhydride of the present invention with the aromatic diamine represented by the general formula (15) in the presence of an organic solvent, to thereby obtain a polyamic acid which is preferable as the polyimide precursor resin of the present invention.

A tetracarboxylic dianhydride used in the method for producing a polyamic acid is the tetracarboxylic dianhydride of the present invention.

In addition, in the aromatic diamine represented by the general formula (15), $R^5$ in the formula (15) is the same as $R^5$ in the general formulae (5) and (6) described for the above-described polyimide of the present invention, and preferred ones thereof are also the same as those of $R^5$ in the general formulae (5) and (6). Examples of the aromatic diamine represented by the general formula (15) include 4,4'-diaminodiphenylmethane, 3,3'-diaminodiphenylmethane, 4,4'-diaminodiphenylethane, 3,3'-diaminodiphenylethane, 3,3'-diaminobiphenyl, 4,4'-diaminodiphenyl ether, 3,3'-diaminodiphenyl ether, 2,2-bis(4-aminophenoxyphenyl)propane, 1,3-bis(4-aminophenoxy)benzene, 1,3-bis(3-aminophenoxy)benzene, bis[4-(4-aminophenoxy)phenyl] sulfone, bis[4-(3-aminophenoxy)phenyl] sulfone, 2,2'-bis(trifluoromethyl)-4,4'-diaminobiphenyl, 3,4'-diaminodiphenyl ether, 4,4'-diaminobenzophenone, 3,3'-diaminobenzophenone, 9,9-bis(4-aminophenyl)fluorene, p-diaminobenzene, m-diaminobenzene, o-diaminobenzene, 4,4'-diaminobiphenyl, 4,4'-diamino-2,2'-dimethylbiphenyl, 4,4'-diamino-3,3'-dimethylbiphenyl, 3,3'-diaminobiphenyl, 2,2'-diaminobiphenyl, 3,4'-diaminobiphenyl, 2,6-diaminonaphthalene, 1,4-diaminonaphthalene, 1,5-diaminonaphthalene, 4,4'-[1,3-phenylenebis(1-methylethylidene)]bisaniline 4,4'-[1,4-phenylenebis(1-methylethylidene)]bisaniline, 3,3'-diaminodiphenyl sulfone, 4,4'-diaminodiphenyl, sulfone, 4,4'-diaminodiphenyl sulfide, 1,4-bis(4-aminophenoxy)benzene, 4,4'-bis(4-aminophenoxy)biphenyl, 4,4'-diaminobenzanilide, o-tolidine sulfone, 2,3,5,6-tetramethyl-1,4-phenylenediamine, 3,3',5,5'-tetramethylbenzidine, 1,5-bis(4-aminophenoxy)pentane, 4,4'-diaminotriphenylamine, 1,4-bis(4-aminobenzoyl) piperazine, 2-phenoxy-1,4-diaminobenzene, bis(4-aminophenyl) terephthalate, bis(4-aminophenyl) terephthalamide, bis(4-aminophenyl) [1,1'-biphenyl]-4,4'-dicarboxylate, 4,4"-diamino-p-terphenyl, N,N'-bis(4-aminobenzoyl)-p-phenylenediamine, bis[4-(4-aminophenoxy)phenyl]ketone, 4-aminophenyl-4-aminobenzoate, [1,1'-biphenyl]-4,4'-diyl bis(4-aminobenzoate), and the like.

A method for producing the aromatic diamine is not particularly limited, and a known method can be employed, as appropriate. In addition, as the aromatic diamine, commercially available one may be used, as appropriate. In addition, one of these aromatic diamines represented by the general formula (15) may be used alone, or two or more thereof may be used in combination.

In addition, the organic solvent used in the step (I) is preferably an organic solvent capable of dissolving both the tetracarboxylic dianhydride of the present invention and the aromatic diamine represented by the general formula (15). Examples of the organic solvent include aprotic polar solvents such as N-methyl-2-pyrrolidone, N,N-dimethylacetamide, N,N-dimethylformamide, dimethyl sulfoxide, γ-butyrolactone, propylene carbonate, tetramethylurea, 1,3-dimethyl-2-imidazolidinone, hexamethylphosphoric triamide, and pyridine; phenol-based solvents such as m-cresol, xylenol, phenol, and halogenated phenols; ether-based solvents such as tetrahydrofuran, dioxane, Cellosolve, and glyme; aromatic solvents such as benzene, toluene, and xylene; and the like. One of these organic solvents may be used alone, or two or more thereof may be used as a mixture.

In addition, the ratio of the tetracarboxylic dianhydride of the present invention and the aromatic diamine represented by the general formula (15) used is not particularly limited, and the acid anhydride groups of the tetracarboxylic dianhydride are preferably 0.2 to 2 equivalents, and more preferably 0.3 to 1.2 equivalents per equivalent of the amino groups of the aromatic diamine. If the preferred ratio of the tetracarboxylic dianhydride and the aromatic diamine used is lower than the lower limit, the polymerization reaction tends not to proceed efficiently, so that a polyamic acid having a high molecular weight cannot be obtained. Meanwhile, if the ratio exceeds the upper limit, a polyamic acid having a high molecular weight tends not to be obtained as in the above described case.

Moreover, the amount of the organic solvent used is preferably such that the total amount of the tetracarboxylic dianhydride of the present invention and the aromatic diamine represented by the general formula (15) can be 1 to 80% by mass (more preferably 5 to 50% by mass) in the total amount of the reaction solution. If the amount of the organic solvent used is less than the lower limit, the polyamic acid tends not to be obtained efficiently. Meanwhile, if the amount of the organic solvent used exceeds the upper limit, the viscosity tends to increase, making the stirring difficult, so that a polymer having a high molecular weight cannot be obtained.

In addition, when the tetracarboxylic dianhydride of the present invention and the aromatic diamine represented by the general formula (15) are reacted with each other, a basic compound may be further added to the organic solvent, from the viewpoints of improving the reaction rate and obtaining a polyamic acid with a high degree of polymerization. The basic compound is not particularly limited, and examples thereof include triethylamine, tetrabutylamine, tetrahexylamine, 1,8-diazabicyclo[5.4.0]-undecene-7, pyridine, isoquinoline, α-picoline, and the like. In addition, the amount of the basic compound used is preferably 0.001 to 10 equivalents, and more preferably 0.01 to 0.1 equivalents per equivalent of the tetracarboxylic dianhydride represented by the general formula (1). If the amount of the basic compound used is less than the lower limit, the effect achieved by the addition tends not to be exhibited. Meanwhile, if the amount of the basic compound used exceeds the upper limit, the basic compound tends to cause color development or the like.

In addition, the reaction temperature for the reaction between the tetracarboxylic dianhydride of the present invention and the aromatic diamine represented by the general formula (15) is not particularly limited, as long as the temperature is adjusted, as appropriate, to a temperature at which these compounds can be reacted with each other. The reaction temperature is preferably 15 to 100° C. In addition, a method for reacting the tetracarboxylic dianhydride of the present invention with the aromatic diamine represented by the general formula (15) is not particularly limited, and it is possible to use, as appropriate, a method by which a polymerization reaction between a tetracarboxylic dianhydride and an aromatic diamine can be conducted. For example, a method may be employed in which the aromatic diamine is dissolved in the solvent under atmospheric pressure in an inert atmosphere of nitrogen, helium, argon, or the like, then the tetracarboxylic dianhydride is added at the reaction temperature, and then the reaction is allowed to proceed for 10 to 48 hours. If the reaction temperature or the reaction time is lower or less than the lower limit, it tends to be difficult to cause the reaction to proceed sufficiently. Meanwhile, if the reaction temperature or the reaction time exceeds the upper limit, the possibility of contamination with a substance (such as oxygen) that degrades the polymerization product tends to increase, so that the molecular weight decreases.

By reacting the tetracarboxylic dianhydride of the present invention with the aromatic diamine represented by the general formula (15) in the presence of an organic solvent as described above, the polyamic acid can be obtained. Note that the ratios of the repeating units (A') and (B') in the polyamic acid are derived from the ratios of the isomers in the tetracarboxylic dianhydride of the present invention as monomers, and basically, the ratios of the acid dianhydride (A) and the acid dianhydride (B) in the tetracarboxylic dianhydride of the present invention are directly values equal to the ratios of the repeating unit (A') and the repeating unit (B').

In addition, in the case where the polyamic acid obtained by the present invention is allowed to contain a different repeating unit other than the repeating units (A') and (B'), a method may be employed in which another tetracarboxylic dianhydride is used together with the tetracarboxylic dianhydride of the present invention in the production of the polyamic acid, and these tetracarboxylic dianhydrides are reacted with the aromatic diamine.

Examples of the other tetracarboxylic dianhydride other than the tetracarboxylic dianhydride of the present invention include aliphatic or alicyclic tetracarboxylic dianhydrides such as butanetetracarboxylic dianhydride, 1,2,3,4-cyclobutanetetracarboxylic dianhydride, 1,2,3,4-cyclopentanetetracarboxylic dianhydride, 2,3,5-tricarboxycyclopentylacetic dianhydride, 3,5,6-tricarboxynorbornane-2-acetic dianhydride, 2,3,4,5-tetrahydrofurantetracarboxylic dianhydride, 1,3,3a,4,5,9b-hexahydro-5-(tetrahydro-2,5-dioxo-3-furanyl)-naphtho[1,2-c]-furan-1,3-dione, 1,3,3a,4,5,9b-hexahydro-5-methyl-5-(tetrahydro-2,5-dioxo-3-furanyl)-naphtho[1,2-c]-furan-1,3-dione, 1,3,3a,4,5,9b-hexahydro-8-methyl-5-(tetrahydro-2,5-dioxo-3-furanyl)-naphtho[1,2-c]-furan-1,3-dione, 5-(2,5-dioxotetrahydrofural)-3-methyl-3-cyclohexene-1,2-dicarboxylic dianhydride, bicyclo[2,2,2]-oct-7-ene-2,3,5,6-tetracarboxylic dianhydride, norbornane-2-spiro-α-cyclopentanone-α'-spiro-2"-norbo rnane-5,5",6, 6"-tetracarboxylic dianhydride, and 5,5'-(1,4-phenylene)bis(hexahydro-4,7-methanoisobenzofuran-1,3-dione);
aromatic tetracarboxylic dianhydrides such as pyromellitic dianhydride, 3,3',4,4'-benzophenonetetracarboxylic dianhydride, 3,3',4,4'-biphenyl sulfonetetracarboxylic dianhydride, 1,4,5,8-naphthalenetetracarboxylic dianhydride, 2,3,6,7-naphthalenetetracarboxylic dianhydride, 3,3',4,4'-biphenyl ether tetracarboxylic dianhydride, 3,3',4,4'-dimethyldiphenylsilanetetracarboxylic dianhydride, 3,3',4,4'-tetraphenylsilanetetracarboxylic dianhydride, 1,2,3,4-furantetracarboxylic dianhydride, 4,4'-bis(3,4-dicarboxyphenoxy)diphenyl sulfide dianhydride, 4,4'-bis(3,4-dicarboxyphenoxy)diphenyl sulfone dianhydride, 4,4'-bis(3,4-dicarboxyphenoxy)diphenylpropane dianhydride, 3,3',4,4'-perfluoroisopropylidenediphthalic dianhydride, 4,4'-(2,2-hexafluoroisopropylidene)diphthalic dianhydride, 3,3',4,4'-biphenyltetracarboxylic dianhydride, 2,3,3',4'-biphenyltetracarboxylic dianhydride, bis(phthalic acid) phenylphosphine oxide dianhydride, p-phenylene-bis(triphenylphthalic) dianhydride, m-phenylene-bis(triphenylphthalic) dianhydride, bis(triphenylphthalic acid)-4,4'-diphenyl ether dianhydride, and bis(triphenylphthalic acid)-4,4'-diphenylmethane dianhydride; and the like.

In addition, as the other tetracarboxylic dianhydride other than the tetracarboxylic dianhydride of the present invention, it is preferable to use the compound represented by following general formula (16):

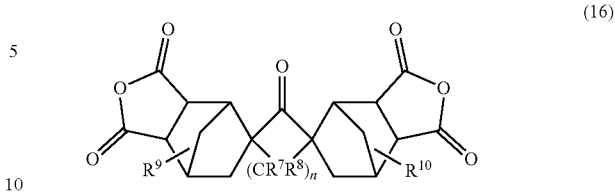

[$R^7$, $R^8$, $R^9$, $R^{10}$, and n in the general formula (16) have the same meanings as those of $R^7$, $R^8$, $R^9$, $R^{10}$, and n in the general formula (13), respectively (preferred ones thereof are also the same)] in the case of, for example, introducing the repeating unit represented by the general formula (14) into the polyamic acid as the other repeating unit (in the case of introducing the repeating unit represented by the general formula (13) into the polyimide obtained by using the polyamic acid). Note that a method for producing the other tetracarboxylic dianhydride represented by the general formula (16) is not particularly limited, and a known method (for example, a method described in International Publication No. WO2011/099517 and a method described in International Publication No. WO2011/099518) can be employed as appropriate.

The compounds and the like listed as examples above can be used as appropriate as the other tetracarboxylic dianhydride other than the tetracarboxylic dianhydride of the present invention. Note that in a case where an aromatic tetracarboxylic acid is used as the other tetracarboxylic dianhydride, the amount of the aromatic tetracarboxylic acid used is preferably changed, as appropriate, within a range where the obtained polyimide can have a sufficient transparency from the viewpoint of preventing color development due to intramolecular CT.

In addition, when the other tetracarboxylic dianhydride as described above is used in the production of the polyimide, the total amount of acid anhydride groups in the tetracarboxylic dianhydride of the present invention and the other tetracarboxylic dianhydride (all tetracarboxylic dianhydrides present in the reaction system) is preferably 0.2 to 2 equivalents (more preferably 0.3 to 1.2 equivalents) per equivalent of the amino groups of the aromatic diamine represented by the general formula (15).

In addition, if the other tetracarboxylic dianhydride is used together with the tetracarboxylic dianhydride of the present invention, the ratio of these used is preferably 9:1 to 5:5 (more preferably 9:1 to 7:3) in a mole ratio ([tetracarboxylic dianhydride of the present invention]:[other tetracarboxylic dianhydride]). If the ratio of the tetracarboxylic dianhydride of the present invention used (mole ratio) is less than the lower limit, the heat resistance of the obtained polyimide tends to be lowered. Meanwhile, if the ratio of the tetracarboxylic dianhydride of the present invention used exceeds upper limit, an effect of physical property of the polyimide tends not to be exhibited when the other tetracarboxylic dianhydride is used.

In addition, when the polyamic acid formed is isolated from the organic solvent after the above-described step (I) is conducted, a method for the isolation is not particularly limited, and a known method capable of isolating a polyamic acid can be employed, as appropriate. For example, a method in which the polyamic acid is isolated as a reprecipitation product or the like may be employed.

2) Method which can be Preferably Used for Producing Polyamic Acid Ester

Next, a method which can be preferably used for producing the polyamic acid ester will be described.

As a method for producing the polyamic acid ester, the following method can be preferably used. Specifically, the method includes first reacting the tetracarboxylic dianhydride of the present invention with any alcohol to obtain a diester dicarboxylic acid, followed by reaction with a chlorinating reagent (for example, thionyl chloride, oxalyl chloride, and the like) to obtain diester dicarboxylic acid chloride (derivative of tetracarboxylic acid). Note that the carbonyl compound of the present invention may be used to prepare the diester dicarboxylic acid chloride (derivative of tetracarboxylic acid). The method next includes preparing a mixture of the aromatic diamine and a monomer component containing the diester dicarboxylic acid chloride thus obtained (component containing the diester dicarboxylic acid chloride and sometimes the tetracarboxylic dianhydride of the present invention) and reacting the monomer component with the aromatic diamine by stirring the mixture in a range of −20 to 120° C. (more preferably −5 to 80° C.) for 1 to 72 hours, to thereby obtain a polyamic acid ester (preferred embodiment of the polyimide precursor resin of the present invention) comprising: the at least one repeating unit (A') selected from the group consisting of structural units (repeating units) represented by the general formula (7) and their enantiomeric structural units (repeating units); and/or the repeating unit (B') represented by the general formula (8) [note that at least one of $Y^1$ and $Y^2$ in the repeating units (A') and (B') represents an alkyl group], wherein the content of the repeating unit (B') in the total amount of the repeating units (A') and (B') is 30 to 100% by mole in a mole ratio.

Note that, if the reaction takes place at a temperature exceeding the upper limit (preferably 80° C.) during stirring, the molecular weight tends to vary depending on the temperature history during polymerization, and also there can be a case where imidization proceeds due to heat. Thus, it tends to be difficult to stably produce the polyimide precursor. In addition, a polyimide precursor composed of the polyamic acid ester can be easily obtained also by dehydration condensation of a diester dicarboxylic acid and the aromatic diamine using a phosphorus-based condensing agent, a carbodiimide condensing agent, or the like. Since a polyimide precursor composed of a polyamic acid ester obtained by the method is stable, a solvent such as water or an alcohol can be added to perform purification such as reprecipitation.

3) Method which can be Preferably Used for Producing Polyamic Acid Silyl Ester

Hereinafter, a method which can be preferably used for producing a polyamic acid silyl ester will be briefly described by dividing the method into the so called indirect method and direct method.

<Indirect Method>

As a method which can be preferably used for producing a polyamic acid silyl ester, the following method (indirect method) can be employed.

Specifically, the method (indirect method) includes first reacting the aromatic diamine with a silylation agent to obtain a silylated product of the aromatic diamine. Note that the silylated aromatic diamine may be purified by distillation or the like as needed. The method next includes dissolving in a dehydrated solvent the silylated aromatic diamine or a mixture of the silylated aromatic diamine and an aromatic diamine (non silylated) to obtain a solution. The method subsequently includes, while stirring the solution, gradually adding the tetracarboxylic dianhydride of the present invention to the solution, followed by stirring in a range of 0 to 120° C. (preferably 5 to 80° C.) for 1 to 72 hours, to thereby obtain a polyamic acid silyl ester (preferred embodiment of the polyimide precursor resin of the present invention) comprising: the at least one repeating unit (A') selected from the group consisting of structural units represented by the general formula (7) and their enantiomeric structural units (repeating units); and/or the repeating unit (B') represented by the general formula (8) [note that at least one of $Y^1$ and $Y^2$ in the repeating units (A') and (B') represents an alkylsilyl group], wherein the content of the repeating unit (B') in the total amount of the repeating units (A') and (B') is 30 to 100% by mole in a mole ratio. The use of the method makes it possible to more efficiently produce a polyamic acid silyl ester.

If the reaction takes place at a temperature exceeding the upper limit (preferably 80° C.) during stirring, the molecular weight tends to vary depending on the temperature history during polymerization, and also there can be a case where imidization proceeds due to heat. Thus, it tends to be difficult to stably produce the polyimide precursor resin. Moreover, the silylation agent used is preferably a silylation agent not containing chlorine atoms. By using a silylation agent not containing chlorine atoms as described above, it becomes unnecessary to purify a silylated aromatic diamine, and thus the process can be further simplified. Examples of the silylation agent not containing chlorine atoms include N,O-bis(trimethylsilyl)trifluoroacetamide, N,O-bis(trimethylsilyl) acetamide, and hexamethyldisilazane. In addition, the silylation agent is particularly preferably N,O-bis(trimethylsilyl) acetamide and hexamethyldisilazane from the viewpoints of low cost and the absence of fluorine atoms. In addition, it is possible to use an amine-based catalyst such as pyridine, piperidine, or triethylamine in the silylation reaction of the aromatic diamine for the purpose of accelerating the reaction. Such an amine-based catalyst can also be used directly as a polymerization catalyst for the polyimide precursor.

<Direct Method>

As the direct method, it is possible to first employ the method which can be preferably used for producing a polyamic acid described above, and the method (direct method) includes preparing the reaction liquid obtained by the step (I) directly as a polyamic acid solution and then mixing the obtained polyamic acid solution with a silylation agent, followed by stirring in a range of 0 to 120° C. (preferably 5 to 80° C.) for 1 to 72 hours, to thereby obtain a polyimide precursor resin composed of the acid silyl ester.

Note that if the reaction takes place at a temperature exceeding the upper limit (preferably 80° C.) during stirring, the molecular weight tends to vary depending on the temperature history during polymerization, and also there can be a case where imidization proceeds due to heat. Thus, it tends to be difficult to stably produce the polyimide precursor. As a silylation agent usable in the direct method, it is preferable to use a silylation agent not containing chlorine atoms because it is unnecessary to purify the silylated polyamic acid or the obtained polyimide. Examples of the silylation agent not containing chlorine atoms include N,O-bis(trimethylsilyl)trifluoroacetamide, N,O-bis(trimethylsilyl)acetamide, and hexamethyldisilazane. In addition, the silylation agent is particularly preferably N,O-bis(trimethylsilyl)acetamide and hexamethyldisilazane from the viewpoints of low cost and the absence of fluorine atoms.

Any of the methods for producing a polyimide precursor described above can be carried out in an organic solvent. In the case of producing a polyimide precursor resin in an organic solvent as described above, it is possible to easily obtain a varnish of the polyimide precursor resin. Then, a polyimide can be easily obtained by applying the thus-obtained varnish onto the surface of a substrate or the like followed by imidization. As a method for such imidization, a method capable of forming an imide bond to prepare a polyimide may be appropriately employed depending on the type of the polyimide precursor resin (in particular, the types of $Y^1$ and $Y^2$ in the formula).

In the foregoing, a method which can be preferably used as a method for producing the polyimide precursor resin of the present invention has been described. Hereinafter, a method which can be preferably used as a method for producing the polyimide of the present invention will be described.

(Method for Producing Polyimide of Present Invention)

A method for producing the polyimide of the present invention is not particularly limited, and it is possible to employ, for example, a method including imidizing a polyamic acid preferable as the polyimide precursor resin of the present invention, to thereby obtain the polyimide of the present invention. Note that the polyamic acid is a polyamic acid comprising: the at least one repeating unit (A') selected from the group consisting of structural units (repeating units) represented by the general formula (7) and containing hydrogen atoms as both $Y^1$ and $Y^2$ in the formula, and their enantiomeric structural units (repeating units); and/or the repeating unit (B') represented by the general formula (8) and containing hydrogen atoms as both $Y^1$ and $Y^2$ in the formula, wherein the content of the repeating unit (B') in the total amount of the repeating units (A') and (B') is 30 to 100% by mole in a mole ratio. The method for preparing the polyamic acid is not particularly limited, and is preferably a method including the step (I) described in the aforementioned method which can be preferably used for producing a polyamic acid.

In addition, a method for the imidization is not particularly limited, as long as imidization of the polyamic acid can be performed by the method. A known method can be employed, as appropriate, and it is preferable to employ, for example, a method in which the imidization is conducted by subjecting the polyamic acid to a heat treatment under a temperature condition of 60 to 400° C. (more preferably 150 to 350° C.) or a method in which the imidization is conducted by using a so-called "imidization agent."

In the case where the method in which the imidization is conducted by a heat treatment is employed, if the heating temperature is lower than 60° C., the progress of the reaction tends to be slow, while if the heating temperature exceeds the upper limit, color development, molecular weight reduction due to thermal decomposition, or the like tends to occur. Meanwhile, when the method in which the imidization is conducted by a heat treatment is employed, the reaction time (heating time) is preferably 0.5 to 5 hours. If the reaction time is less than the lower limit, it tends to be difficult to conduct the imidization sufficiently, while if the reaction time exceeds the upper limit, color development, molecular weight reduction due to thermal decomposition, or the like tends to occur.

On the other hand, when the method in which the imidization is conducted by utilizing a so-called "imidization agent" is employed, it is preferable to perform the imidization of the polyamic acid in a solvent in the presence of an imidization agent. As the solvent, the same solvent as the organic solvent used for the above-described method for producing a polyimidic acid of the present invention can be used preferably.

As the imidization agent, a known imidization agent can be used, as appropriate, and examples thereof include acid anhydrides such as acetic anhydride, propionic anhydride, and trifluoroacetic anhydride; tertiary amines such as pyridine, collidine, lutidine, triethylamine, and N-methylpiperidine; and the like. In addition; when the imidization is conducted by adding the imidization agent, the reaction temperature for the imidization is preferably −40° C. to 200° C., more preferably 0 to 180° C., and further preferably 30 to 150° C. Meanwhile, the reaction time is preferably 0.1 to 48 hours. If the reaction temperature or time is lower or less than the lower limit, it tends to be difficult to conduct the imidization sufficiently. Meanwhile, if the reaction temperature or time exceeds the upper limit, the possibility of contamination with a substance (oxygen or the like) that degrades the polymerization product tends to increase, so that the molecular weight decreases. In addition, the amount of the imidization agent used is not particularly limited, and may be several millimoles to several moles (preferably about 0.05 to 4.0 moles) per mole of the repeating unit in the polyamic acid.

In addition, for the chemical imidization using the imidization agent, it is preferable to employ, as the imidization agent, a combination (combined use) of a condensation agent (such as a carboxylic anhydride, a carbodiimide, an acid azide, or an active ester-forming agent) with a reaction accelerator (such as tertiary amine). The combined use of a condensation agent (a so-called dehydration condensation agent such as a carboxylic anhydride, a carbodiimide, an acid azide, or an active ester-forming agent) with a reaction accelerator (such as tertiary amine) as described above makes it possible to perform the imidization by more efficient dehydration ring-closure of the polyamic acid under a low-temperature condition (more preferably under a temperature condition of about 100° C. or below).

The condensation agent is not particularly limited, and examples thereof include carboxylic anhydrides such as acetic anhydride, propionic anhydride, and trifluoroacetic anhydride; carbodiimides such as N,N'-dicyclohexylcarbodiimide (DCC); acid azides such as diphenylphosphoryl azide (DPPA); active ester-forming agents such as Castro's reagent; and dehydration condensation agents such as 2-chloro-4,6-dimethoxytriazine (CDMT). Of these condensation agents, acetic anhydride, propionic anhydride, and trifluoroacetic anhydride are preferable, acetic anhydride and propionic anhydride are more preferable, and acetic anhydride is further preferable from the viewpoints of reactivity, availability, and practicability. One of these condensation agents may be used alone or two or more thereof may be used in combination.

In addition, the reaction accelerator may be any, as long as the reaction accelerator can be used for conversion of the polyamic acid to a polyimide by condensation, and a known compound can be used, as appropriate. The reaction accelerator can also function as an acid scavenger that captures the acid by-produced during the reaction. For this reason, the use of the reaction accelerator accelerates the reaction and suppresses the reverse reaction due to the by-produced acid, so that the reaction can be caused to proceed more efficiently. The reaction accelerator is not particularly limited, and is more preferably one also having a function of an acid scavenger. Examples of the reaction accelerator include tertiary amines such as triethylamine, diisopropylethylamine, N-methylpiperidine, pyridine, collidine, lutidine, 2-hydroxypyridine, 4-dimethylaminopyridine (DMAP), 1,4-diazabicyclo[2.2.2]octane (DABCO), diazabicyclononene (DBN), and diazabicycloundecene (DBU), and the like. Of these reaction accelerators, triethylamine, diisopropylethylamine, N-methylpiperidine, and pyridine are preferable, triethylamine, pyridine, and N-methylpiperidine are more preferable, and triethylamine and N-methylpiperidine are further preferable from the viewpoints of reactivity, availability, and practicability. One of those reaction accelerators may be used alone or two or more thereof may be used in combination.

In addition, for the chemical imidization using the imidization agent, the chemical imidization may be conducted by, for example, adding a catalytic amount of a reaction accelerator (such as DMAP) and an azeotropic dehydration agent (such as benzene, toluene, or xylene), and removing water produced when the polyamic acid is converted to the imide by azeotropic dehydration. For the chemical imidization (imidization using an imidization agent), the azeotropic dehydration agent may be used, as appropriate, together with the reaction accelerator as described above. The azeotropic dehydration agent is not particularly limited, and an azeotropic dehydration agent may be selected from known azeotropic dehydration agents and used, as appropriate, according to the type of the material used for the reaction and the like.

As described above, the method for producing a polyimide of the present invention preferably comprises: the step (I); and a step (II) of imidizing the polyamic acid obtained in the step (I), to thereby obtain a polyimide of the present invention. When the method comprises the steps (I) and (II) as described above, a polyimide can be produced more efficiently by the continuous steps.

Note that when the method in which the imidization is conducted by a heat treatment is employed for the imidization in a case where the method comprising these steps (I) and (II) is used, the following method may be employed. Specifically, after the step (I) is conducted, the reaction liquid obtained by reacting the tetracarboxylic dianhydride of the present invention with the aromatic diamine represented by the general formula (15) in the organic solvent (the reaction liquid comprising the polyamic acid) is directly used without isolation of the polyamic acid. The solvent is removed from the reaction liquid by subjecting the reaction liquid to a treatment (solvent removal treatment) for removing the solvent by evaporation, and then the imidization is conducted by the heat treatment. This treatment for removing the solvent by evaporation makes it possible to perform a heat treatment or the like after the polyamic acid is isolated in the form of a film or the like. A temperature condition in the method for the treatment for removing the solvent by evaporation (solvent removal treatment) is preferably 0 to 180° C., and more preferably 30 to 150° C. If the temperature condition in the drying treatment is lower than the lower limit, it tends to be difficult to sufficiently remove the solvent by evaporation. Meanwhile, if the temperature condition exceeds the upper limit, the solvent tends to boil, resulting in formation of a film containing air bubbles or voids. In this case, for example, When a polyimide in the form of a film is produced, the obtained reaction liquid may be directly applied onto a base material (for example, a glass plate), followed by the treatment for removing the solvent by evaporation and the heat treatment. Thus, a polyimide in the form of a film can be produced by a simple method. Note that a method for applying the reaction liquid is not particularly limited, and a known method (such as a cast method) can be employed, as appropriate. In addition, when the polyamic acid is used after isolation from the reaction liquid, a method for the isolation is not particularly limited, and a known method capable of isolating a polyamic acid can be employed, as appropriate. For example, a method may be employed in which the polyamic acid is isolated as a reprecipitation product.

In addition, suppose a case where the method comprising the steps (I) and (II) is used and the method in which the imidization is conducted by using the "imidization agent" is employed. In such a case, since the method in which the imidization is conducted by using the "imidization agent" is basically a method in which the imidization is preferably performed in a solvent (more preferably the organic solvent described for the above-described method for producing a polyamic acid of the present invention), it is preferable to employ, for example, a method in which the reaction liquid (the reaction liquid comprising the polyamic acid) obtained by reacting the tetracarboxylic dianhydride of the present invention with the aromatic diamine represented by the general formula (15) in the organic solvent is directly used (the reaction liquid is directly used without isolation of the polyamic acid from the reaction liquid after the step (I) is conducted), and the imidization is conducted by adding the imidization agent to the reaction liquid.

In addition, the solvent used when the method in which the imidization is conducted by using the "imidization agent (preferably a combination of a condensation agent with a reaction accelerator)" is employed is preferably the organic solvent (the solvent used for the polymerization: the polymerization solvent) described for the above-described method for producing a polyamic acid of the present invention, from the viewpoints as described above (the viewpoints of directly using the reaction liquid and the like). Especially, the solvent is preferably N,N-dimethylacetamide, N-methyl-2-pyrrolidone, N,N-dimethylformamide, 1,3-dimethyl-2-imidazolidinone, dimethyl sulfoxide, or the like, and more preferably N,N-dimethylacetamide. One of these organic solvents (polymerization solvents) may be used alone, or two or more thereof may be used as a mixture.

In addition, when the reaction liquid (the reaction liquid comprising the polyamic acid) is directly used and the imidization is conducted by adding the imidization agent to the reaction liquid, the organic solvent (polymerization solvent) is preferably one having a boiling point of 20° C. or higher, and preferably one having a boiling point of 50 to 250° C. If the boiling point is lower than the lower limit, polymerization under atmospheric pressure at normal temperature tends to be difficult, so that the polymerization has to be carried out under a special condition, namely, under pressure or under a low temperature. Meanwhile, if the boiling point exceeds the upper limit, such an organic solvent tends to be difficult to remove in a step of drying an obtained polyimide in the form of powder after washing, so that the solvent remains in the obtained polyimide.

In addition, when a combination of a condensation agent with a reaction accelerator is used as the imidization agent, a temperature condition for the chemical imidization is preferably −40° C. to 200° C., more preferably −20° C. to 150° C., further preferably 0 to 150° C., and particularly preferably 50 to 100° C. If the temperature exceeds the upper limit, an undesirable side reaction tends to proceed, so that the polyimide cannot be obtained. Meanwhile, if the temperature is lower than the lower limit, the reaction rate of the chemical imidization tends to be lowered, or the reaction itself tends not to proceed, so that the polyimide cannot be obtained. As described above, when the condensation agent and the reaction accelerator are used in combination, the imidization can be performed in a relatively low-temperature region of from −40° C. to 200° C. Hence, it is possible to reduce the load on the environment, and the method can be advantageous in terms of the manufacturing process.

In addition, when a combination of a condensation agent with a reaction accelerator is used as the imidization agent, the amount of the condensation agent used is not particularly limited, and is preferably 0.05 to 10.0 moles, and further preferably 1 to 5 moles per mole of the repeating unit in the polyamic acid. If the amount of the condensation agent (imidization agent) used is less than the lower limit, the reaction rate of the chemical imidization tends to be lowered or the reaction itself tends not to proceed sufficiently, so that the polyimide cannot be obtained sufficiently. Meanwhile, if the amount of the condensation agent exceeds the upper limit, the polyimide tends not to be obtained efficiently, for example, because an undesirable side reaction proceeds.

In addition, when a combination of a condensation agent with a reaction accelerator is used as the imidization agent, the amount of the reaction accelerator used is not particularly limited, and is preferably 0.05 to 4.0 moles, and further preferably 0.5 to 2 moles per mole of the repeating unit in the polyamic acid. If the amount of the reaction accelerator used is less than the lower limit, the reaction rate of the chemical imidization tends to be lowered or the reaction itself tends not to proceed sufficiently, so that the polyimide cannot be obtained sufficiently. Meanwhile, if the amount of the reaction accelerator used exceeds the upper limit, the polyimide tends not to be obtained efficiently, for example, because an undesirable side reaction proceeds.

In addition, an atmosphere condition for the chemical imidization is preferably an inert gas atmosphere of nitrogen gas or the like or a vacuum condition, from the viewpoint of preventing color development due to oxygen in the air and molecular weight reduction due to water vapor in the air. In addition, a pressure condition for the chemical imidization is not particularly limited, and is preferably 0.01 hPa to 1 MPa, and more preferably 0.1 hPa to 0.3 MPa. If the pressure is lower than the lower limit, the solvent, the condensation agent, and the reaction accelerator tend to be gasified, so that the stoichiometry is disturbed and an adverse influence is exerted on the reaction, making it difficult to cause the reaction to proceed sufficiently. Meanwhile, if the pressure exceeds the upper limit, an undesirable side reaction tends to proceed, or the solubility of the polyamic acid tends to decease, so that precipitation occurs before the imidization.

In addition, when the polyimide obtained by the present invention is obtained in the form of being dissolved in the organic solvent (polymerization solvent), the polyimide may be precipitated by concentration, as appropriate, or the polyimide may be precipitated by dropwise addition to a solvent in which the polyimide is insoluble, and then collected. Note that it is also possible to obtain the polyimide as a precipitate by dropwise addition to a solvent in which the polyimide is insoluble as described above. In this case, it is also possible to obtain a polyimide in the form of powder (particles).

Note that, in the case of producing a polyimide using the method including the steps (I) and (II), the ratios of the repeating units (A) and (B) in the obtained polyimide are derived from the ratios of the isomers in the tetracarboxylic dianhydride of the present invention as monomers, and basically, the ratios of the acid dianhydride (A) and the acid dianhydride (B) in the tetracarboxylic dianhydride of the present invention are directly equal to the ratios of the repeating unit (A) and the repeating unit (B).

Note that, to obtain a polyimide comprising another repeating unit together with the repeating units (A) and (B) by the present invention, the polyamic acid used for producing the polyimide may be one comprising another repeating unit together with the repeating units (A') and (B'). For example, when the above-described method for producing a polyimide of the present invention comprises the steps (I) and (II), another tetracarboxylic dianhydride is used together with the tetracarboxylic dianhydride of the present invention and these tetracarboxylic dianhydrides are reacted with the aromatic diamine in the step (I), and then the step (II) may be performed. As the other tetracarboxylic dianhydride other than the tetracarboxylic dianhydride of the present invention, it is possible to use, as appropriate, the same tetracarboxylic dianhydride as described in the step (I).

EXAMPLES

Hereinafter, the present invention will be described more specifically on the basis of Examples and Comparative Examples; however, the present invention is not limited to Examples below.

Note that the molecular structures and the like of compounds obtained in Examples and Comparative Examples to be described later were identified by employing as appropriate measurements such as infrared absorption spectrum measurement (IR measurement), nuclear magnetic resonance spectrum measurement (NMR measurement), and the like depending on the type of the compound. Here, the IR measurement and the NMR measurement used, as measuring apparatuses, an IR measuring apparatus (manufactured by Thermo Scientific under the trade name of Nicolet 380 FT-IR Spectrometer) and an NMR measuring apparatus (manufactured by VARIAN under the trade name of UNITY INOVA-600), respectively.

<1> Synthesis of Carbonyl Compound

Example 1

First, in a 3 L eggplant flask, 5,5'-bibicyclo[2.2.1]hept-2-ene (557 g, 2.99 mol: hereinafter, the compound is sometimes simply referred to as "BNB") represented by the following general formula (17):

[Chem. 17]

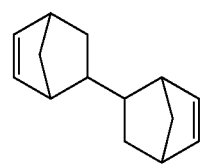

(17)

and toluene (1.8 kg) were added, followed by thorough mixing to obtain a uniform solution (BNB-toluene solution). Note that such BNB includes a stereoisomer A composed of a compound having an endo/exo type three-dimensional structure represented by the following general formula (18) and its enantiomeric compound having an exo/endo type three-dimensional structure (hereinafter sometimes referred to to simply as "BNB-A." Note that endo/exo type and exo/endo type enantiomers cannot be distinguished spectroscopically, and thus are referred to as the "stereoisomer A" together), and a stereoisomer B having an endo/endo type three-dimensional structure represented by the following general formula (19), and the BNB used in the Present Example was one with a BNB-A/BNB-B mole ratio ([BNB-A]/[BNB-B]) of 4/96.

[Chem. 18]

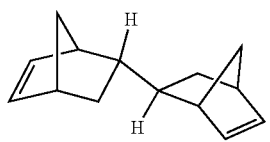

(18)

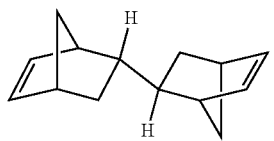

(19)

Next, the atmospheric gas inside a 50 L glass-lined reaction kettle (GL reaction kettle) was replaced with nitrogen, and then methanol (13.1 kg) and $CuCl_2$ (II) (1.65 kg, 12.3 mol) were added to the reaction kettle and stirred to adjust the temperature inside the reaction kettle to 20 to 25° C. Subsequently, the BNB-toluene solution obtained as described above was added to the reaction kettle, followed by further addition of $Pd_3 (OAc)_5(NO_2)$ (3.4 g, 0.0149 mol) to obtain a mixture liquid in the reaction kettle (note that $Pd_3(OAc)_5(NO_2)$ was produced by employing a method described in page 1991 of Dalton Trans (vol. 11), published in 2005). Next, the pressure inside the reaction kettle was reduced to −0.08 MPaG, followed by introduction of carbon monoxide into the reaction kettle to adjust the pressure inside the reaction kettle to 0.03 MPaG. Subsequently, the temperature inside the reaction kettle was adjusted to 25° C. and the mixture liquid was stirred for 4 hours. Thereafter, while continuing the stirring, the temperature inside the reaction kettle was gradually raised to 40° C., and the stirring was continued for a further 4 hours under the temperature condition of 40° C. After that, the stirring of the mixture liquid was stopped, and the mixture liquid was allowed to stand overnight (13.5 hours) to obtain a reaction liquid as a brown suspension.

Next, the pressure was released by removing the atmospheric gas containing carbon monoxide from the inside of the reaction kettle, and the atmospheric gas inside the reaction kettle was replaced with nitrogen. Subsequently, the temperature was raised to 50° C. while allowing nitrogen to flow into the reaction kettle, and it was confirmed that the concentration of carbon monoxide in the gas discharged from the reaction kettle (outlet gas) was 0 ppm. Thereafter, the temperature inside the reaction kettle was further raised to 65° C., and thereby methanol was distilled off from the reaction liquid in the reaction kettle to obtain a solid content. Next, toluene (20 kg) was added to the inside of the reaction kettle having the precipitated solid content therein to obtain a mixture of the solid content and toluene. After that, for the purpose of completely removing methanol from the mixture, the pressure inside the reaction kettle was reduced until the pressure reached −0.07 MPaG, and the temperature was raised to 73° C. to partially distill off the solvent in the mixture. Subsequently, toluene (5.0 kg) was further added to the mixture, then the temperature was raised to 80° C. with stirring, and filtration was performed to separate and collect the precipitate (solid content) and the filtrate. Next, the resultant precipitate was washed with toluene (5.0 kg), and the washing liquid was added to the filtrate. Subsequently, the filtrate was heated, and, while kept at a temperature of 80° C., the filtrate was washed twice with 5% hydrochloric acid (1.0 kg), once with saturated sodium bicarbonate water (10 kg), and once with ion exchanged water (10 kg). After washing as described above, the resultant organic layers were subjected to filter filtration, and the solid content precipitated in the washing liquid was removed (separated) to obtain organic layers. Subsequently, the solid content removed from the washing liquid was washed with toluene (5.0 kg), and then the washing liquid was added to the organic layers. The organic layers were charged again into the 50 L reaction kettle and heated to a temperature of 110° C. with stirring to distill off toluene (the amount of toluene distilled was 23 Kg). After that, the heating was stopped, and the reaction kettle was gradually cooled for recrystallization to precipitate solid content (crystals). The solid content (crystals) thus obtained was collected by filtration, washed four times with toluene (0.6 kg), and vacuum dried at 60° C. By such operations, 873 g of a product (white crystals) was obtained.

To identify the structure of the thus obtained product, IR measurement and NMR ($^1$H-NMR, $^{13}$C-NMR) measurement were carried out, and the obtained product was identified to be 5,5'-bi-2-norbornene-5,5',6,6'-tetracarboxylic acid tetramethyl ester (hereinafter sometimes referred to as "BNBTE") represented by the following formula (20):

[Chem. 19]

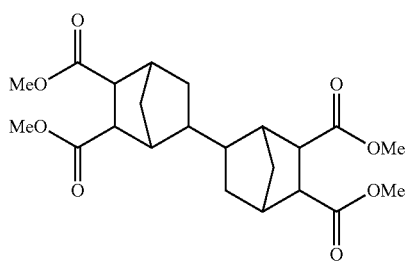

(20)

Figure 2:
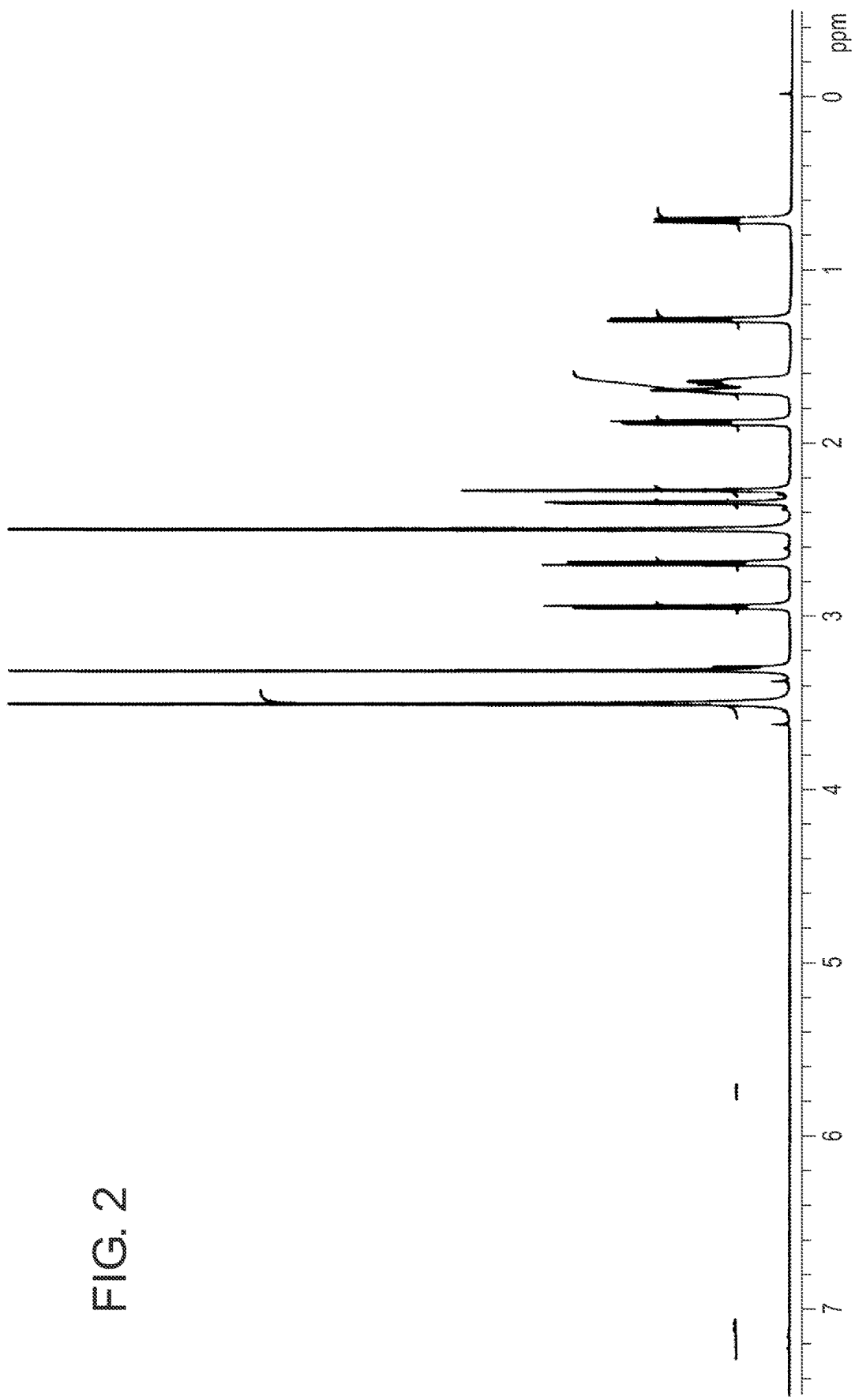
FIG. 2 is a graph showing $^1$H-NMR of the product obtained in Example 1.
Figure 3:
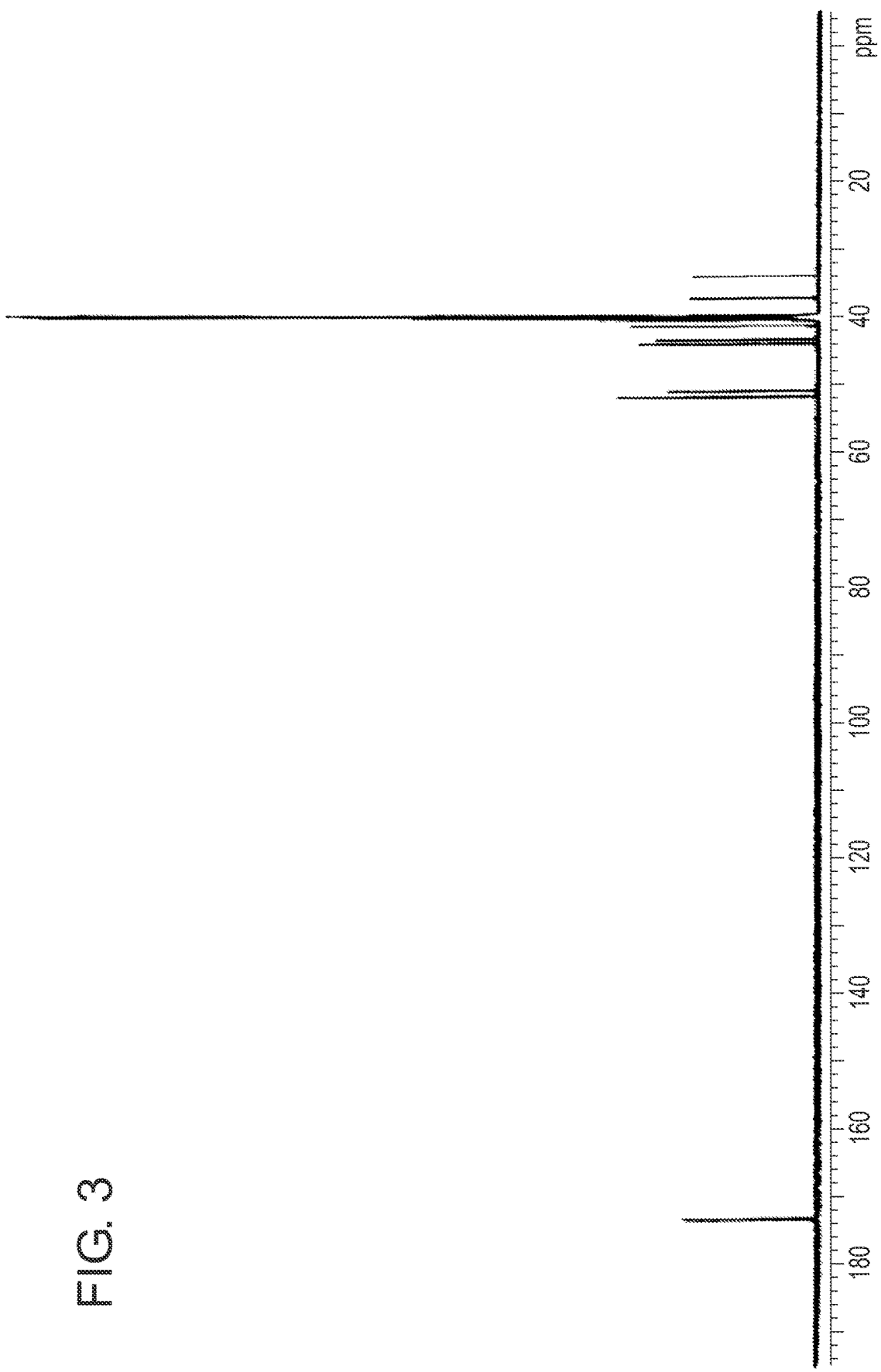
FIG. 3 is a graph showing $^{13}$C-NMR of the product obtained in Example 1.

[in the formula (20), Me represents a methyl group], and the yield was calculated to be 69%. Note that 5,5'-bi-2-norbornene-5,5',6,6'-tetracarboxylic acid tetramethyl ester can include a stereoisomer A composed of a compound having an endo/exo type three-dimensional structure represented by the following general formula (21) and its enantiomeric compound having an exo/endo type three-dimensional structure (hereinafter sometimes referred to as "BNBTE-A." Note that endo/exo type and exo/endo type enantiomers cannot be distinguished spectroscopically, and thus are evaluated as the "stereoisomer A" together in the following description), and a stereoisomer B having an endo/endo type three-dimensional structure represented by the following general formula (22) (hereinafter sometimes referred to as "BNBTE-B"), and, as a result of the above structural identification (IR measurement, NMR measurement), the product obtained as described above was identified to be 5,5'-bi-2-norbornene-5,5',6,6'-tetracarboxylic acid tetramethyl ester containing BNBTE-B as a stereoisomer at a rate of 100% by mole. As a result of IR measurement and NMR measurement of such a product, FIG. 1 shows a graph of an IR spectrum, FIG. 2 shows a graph of $^1$H-NMR, and FIG. 3 shows a graph of $^{13}$C-NMR.

[Chem. 20]

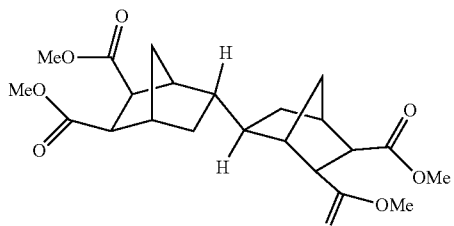
(21)

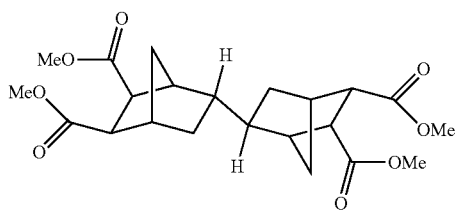
(22)

Moreover, when a GPC analysis was conducted on the obtained product, the content of impurities (a polymerization product in which norbornene rings in the raw material compound are addition-polymerized, a polymerization product in which multiple norbornene rings are bonded at keto groups, and the like) was identified to be 0.17%. Note that the GPC analysis was conducted using a gel permeation chromatography measuring apparatus (GPC, manufactured by Tosoh Corporation under the trade name of HLC-8020/4 columns: manufactured by Tosoh Corporation under the trade name of TSK gel $GMH_{HR}$, and solvent: tetrahydrofuran (THF)).

From these results, it was found that the method employed in Example 1 made it possible to sufficiently efficiently produce BNBTE (5,5'-bi-2-norbornene-5,5',6,6'-tetracarboxylic acid tetramethyl ester) containing BNBTE-B as a stereoisomer at a rate of 100% by mole.

Comparative Example 1

A 300 mL autoclave vessel made of glass was added with methanol (820 mL), $CuCl_2(II)$ (81.7 g, 608 mmol), BNB (20.1 g, 108 mmol) containing BNB-A and BNB-B as stereoisomers at a mole ratio ([BNB-A]/[BNB-B]) of 25/75, and $Pd_3(OAc)_5(NO_2)$ (167 mg, 0.741 mmol in terms of Pd) to obtain a mixture liquid (note that $Pd_3(OAc)_5(NO_2)$ was produced by employing a method described in page 1991 of Dalton Trans (vol. 11), published in 2005).

Subsequently, a glass tube was provided so that bubbling of gas could be performed through the glass tube to the mixture liquid present inside the vessel. Next, the vessel was tightly closed and the inside atmospheric gas was replaced with nitrogen. After that, a vacuum pump was connected to the vessel to reduce the pressure inside the vessel (pressure inside the vessel: 0.015 MPa). Next, the mixture liquid was stirred for 1.5 hours while supplying, by bubbling, carbon monoxide at a rate (flow rate) of 0.015 mole equivalents/min in the raw material compound through the glass tube into the mixture liquid and maintaining the conditions of temperature: 25 to 30° C. and pressure: 0.03 MPaG. After that, the temperature condition was changed and the mixture liquid was further stirred for 3 hours while maintaining the conditions of temperature: 40° C. and pressure: 0.16 MPa. Thereby, the reaction liquid was obtained.

Subsequently, the atmospheric gas containing carbon monoxide was removed from the inside of the vessel. Then, methanol was removed (removed by distillation) from the reaction liquid by concentrating the reaction liquid with an evaporator while maintaining the temperature within a range of 30 to 40° C. Thereby, the reaction product was obtained. After that, the reaction product was added with chloroform (600 ml), followed by Celite® filtration and washing of the filtrate three times with 5% hydrochloric acid (300 ml), twice with saturated sodium bicarbonate water (300 ml), and once with ion exchanged water (300 ml). Thereby, organic layers were collected. Then, the organic layers were added with 90 g of anhydrous sodium sulfate as a desiccant, followed by stirring for 1 hour. Next, the desiccant was separated by filtration from the organic layers. After the desiccant was separated by filtration, the organic layers were concentrated. Thereby, 50.8 g of a brown oily product was obtained.

Next, the oily product was added with isopropyl alcohol (203 mL) to obtain a mixture liquid. Thereafter, the mixture liquid was introduced into the bath of an ultrasonic cleaner whose temperature was adjusted to 40° C., and the oily product was immersed in the isopropyl alcohol for 10 minutes (so called "sonication"). Thereby, a precipitate was deposited in the mixture liquid. The precipitate thus deposited was separated by filtration from the mixture liquid to obtain a filtrate. Then, the resultant filtrate was concentrated to obtain a brown oily product (note that the amount of the precipitate obtained as described above was 20.0 g and the amount of the oily product was 25.2 g).

Figure 4:
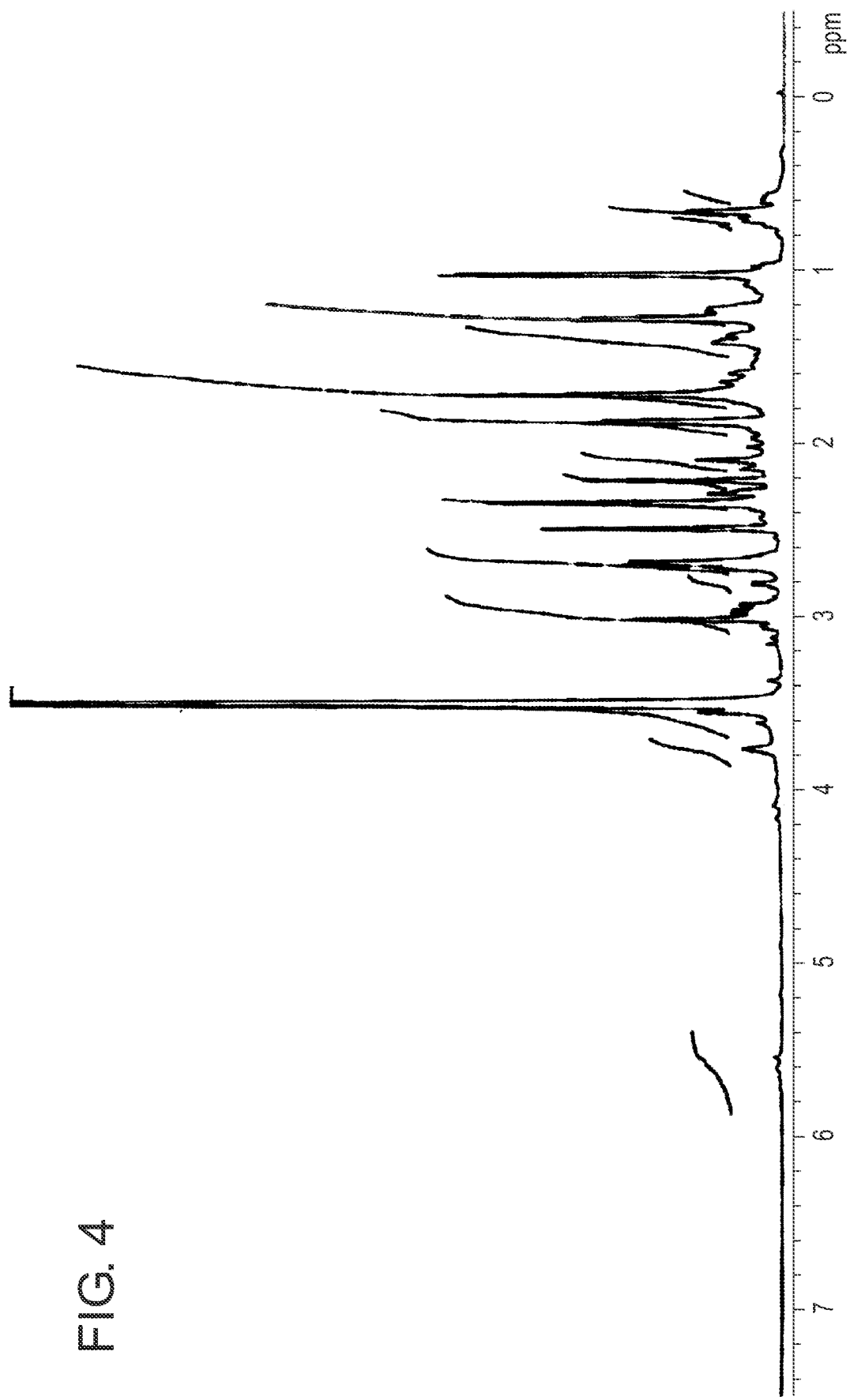
FIG. 4 is a graph showing $^1$H-NMR of an oily product obtained in Comparative Example 1.
Figure 5:
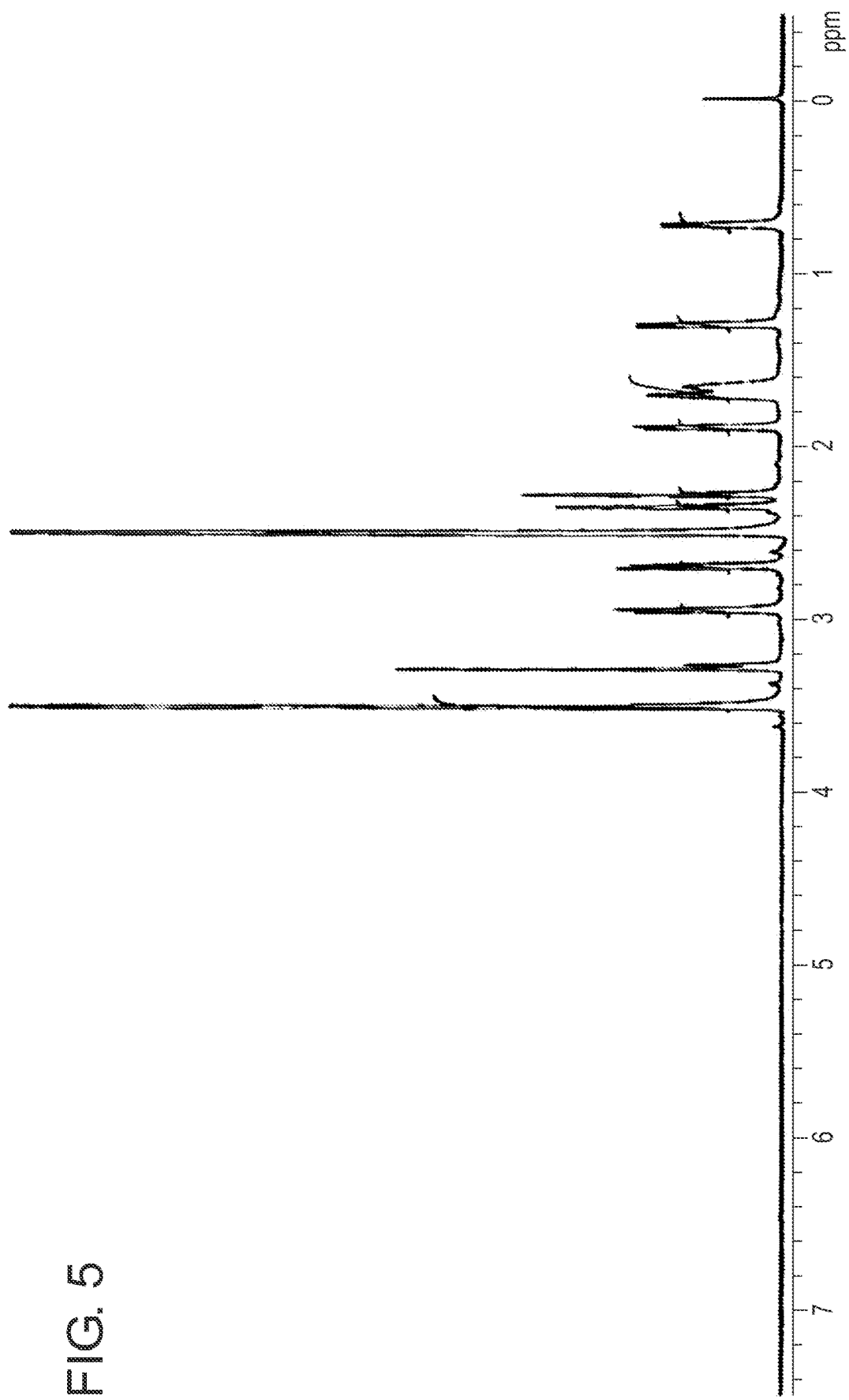
FIG. 5 is a graph showing $^1$H-NMR of a precipitate obtained in Comparative Example 1.

To identify the structure of the thus obtained oily product, $^1$H-NMR measurement was carried out. As a result, the oily product was identified to be a mixture of BNBTE stereoisomers with a BNBTE-A/BNBTE-B mole ratio ([BNBTE-A]/[BNBTE-B]) of 71/29 (BNBTE having a BNBTE-B content of 29% by mole). Note that, when $^1$H-NMR measurement was similarly carried out for structural identification of the precipitate separated when obtaining the filtrate, the precipitate was identified to be a mixture of BNBTE stereoisomers with a BNBTE-A/BNBTE-B mole ratio ([BNBTE-A]/[BNBTE-B]) of 0/100 (BNBTE having a BNBTE-B content of 100% by mole). As described above, the oily product and the precipitate were both a mixture of BNBTE stereoisomers, and their isomer ratios were confirmed to be different. Note that, as the results of $^1$H-NMR measurement, FIG. 4 shows a graph of $^1$H-NMR of the oily product (concentrate of the filtrate) and FIG. 5 shows a graph of $^1$H-NMR of the precipitate (solid).

As described above, in Comparative Example 1, the oily product was collected to obtain BNBTE for comparison with a BNBTE-A/BNBTE-B mole ratio ([BNBTEA]/[BNBTE-B]) of 71/29 (comparative BNBTE having a BNBTE-B content of 29% by mole). Note that, since the precipitate and the oily product are both BNBTE but have different stereoisomer ratios, it was found that BNBTE-A and BNBTE-B have different solubilities to solvents and that it is possible to simultaneously prepare BNBTEs with different BNBTE-A/BNBTE-B content ratios depending on the component collected (solid content or oily product) by the so called crystallization step as employed in Comparative Example 1.

<2> Synthesis of Tetracarboxylic Dianhydride

Example 2

The BNBTE obtained in Example 1 (having a BNBTE-B content of 100% by mole) was used to prepare a tetracarboxylic dianhydride as follows. Specifically, first, a 50 L GL reaction kettle was subjected to replacement with nitrogen, and added with the BNBTE obtained in Example 1 (850 g, 2.01 mol, BNBTE-B content: 100% by mole), acetic acid (12.2 kg), and trifluoromethanesulfonic acid (7.6 g, 0.050 mol) to obtain a mixture liquid. Next, the mixture liquid was heated to 113° C. and maintained at the temperature (113° C.) to carry out a step of distilling a vapor (acetic acid and the like) while adding acetic acid dropwise with a pump so that the amount of liquid in the reaction kettle was constant. Note that, in this step, it was confirmed that a white precipitate was formed in the liquid (in the reaction solution) inside the flask 15 minutes after the start of vapor distillation. In addition, in this step, the distillate distilled out of the system was analyzed every hour by mass measurement and gas chromatograph to confirm the progress of reaction. Note that, by such analysis, it was confirmed that acetic acid, methyl acetate, and water were present in the distillate. Then, 6 hours after the start of vapor distillation in this step, the distillation of methyl acetate stopped. Thus, the heating was stopped for cooling to room temperature (25° C.) to carry out recrystallization. The resultant crystals were filtered, washed once with acetic acid (0.6 kg) and five times with ethyl acetate (0.5 kg), and then dried under vacuum. In this way, 586 g of white powder was obtained.

To identify the structure of the thus obtained white powder (product), IR measurement and NMR ($^1$H-NMR, $^{13}$C-NMR) measurement were carried out, and the product obtained in Example 2 was identified to be 5,5'-bi-2-norbornene-5,5',6,6'-tetracarboxylic acid-5,5',6,6'-dianhydride (hereinafter sometimes referred to as "BNBDA") represented by the following general formula (23):

[Chem. 21]

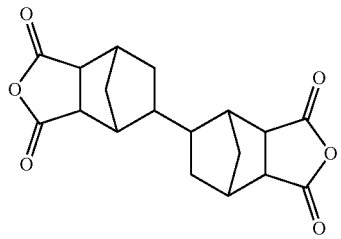

Figure 6:
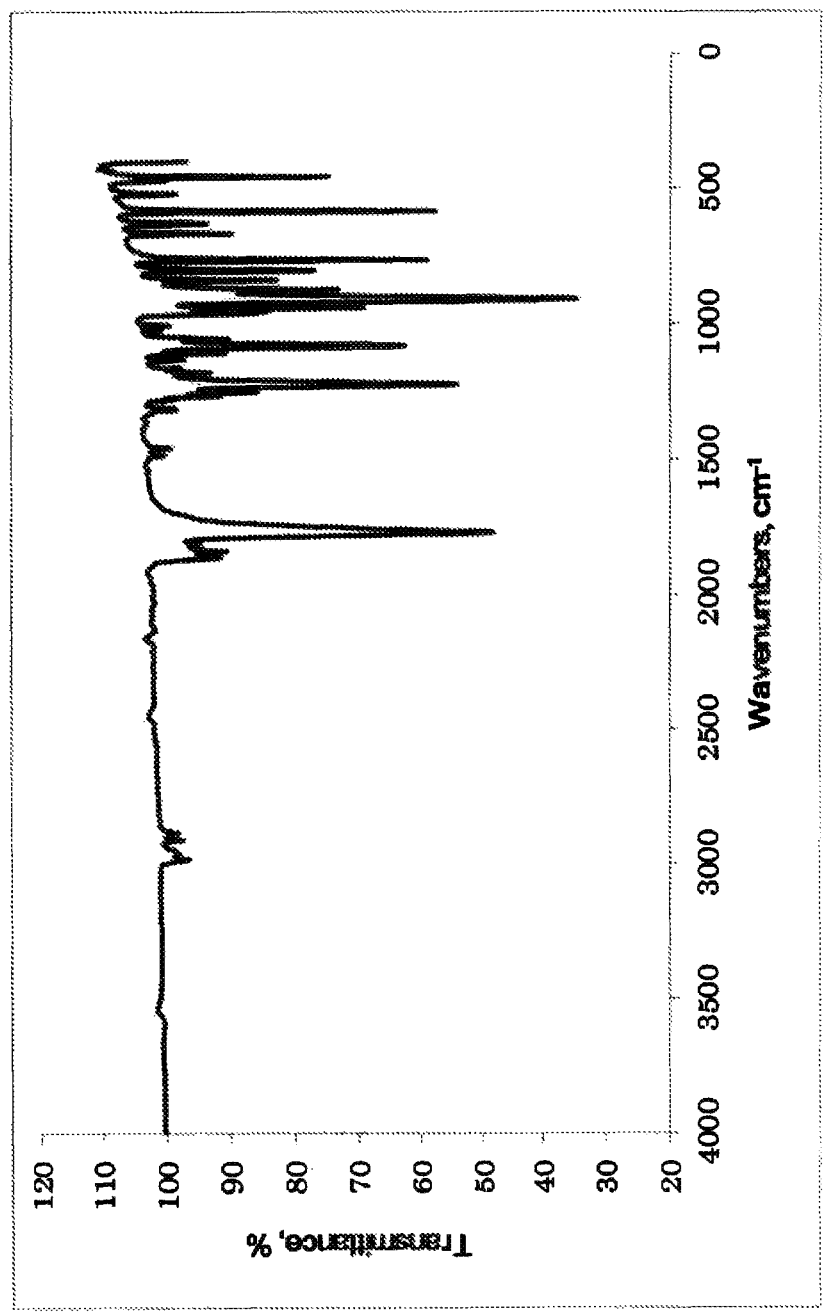
FIG. 6 is a graph showing an IR spectrum of a product obtained in Example 2.
Figure 7:
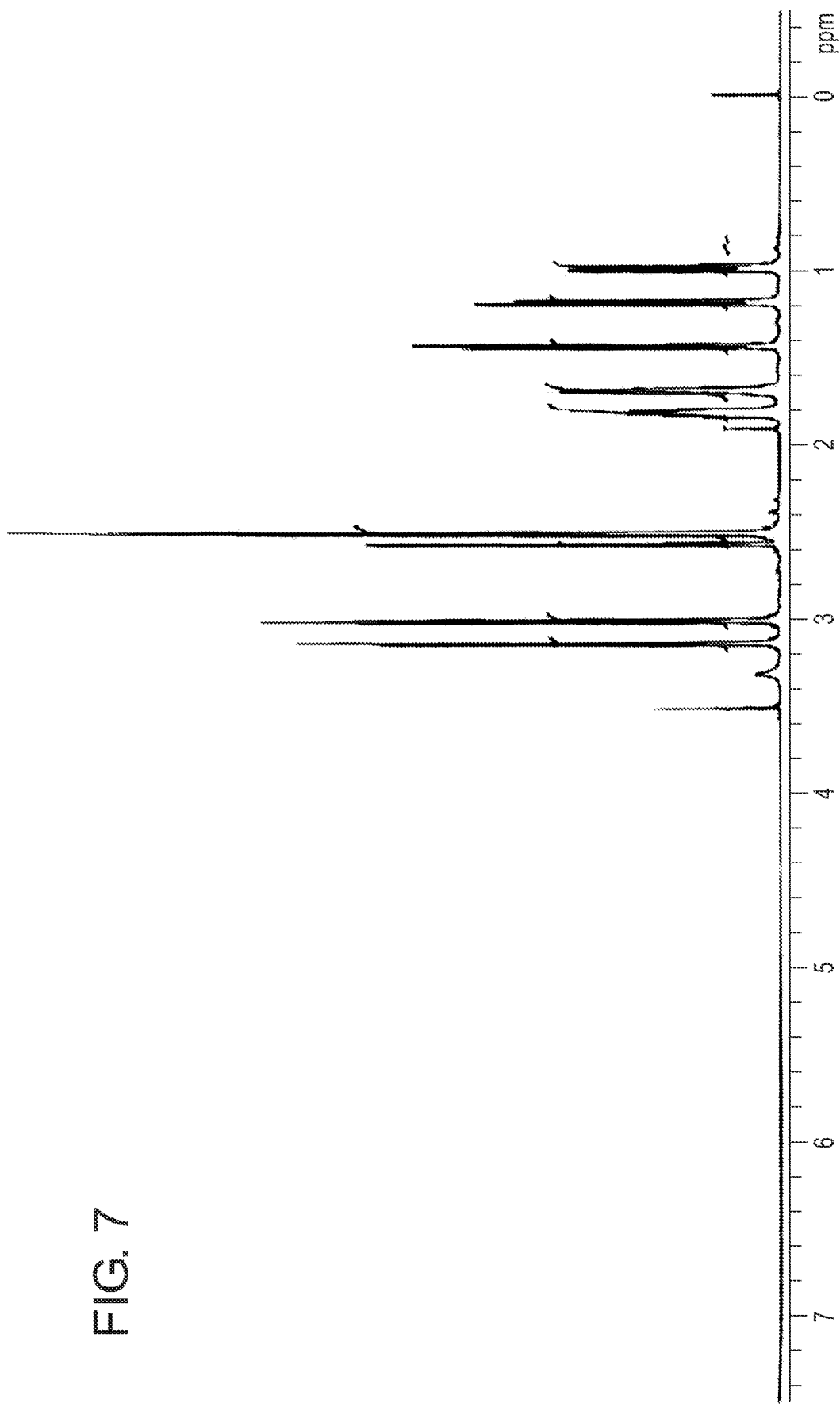
FIG. 7 is a graph showing $^1$H-NMR of the product obtained in Example 2.
Figure 8:
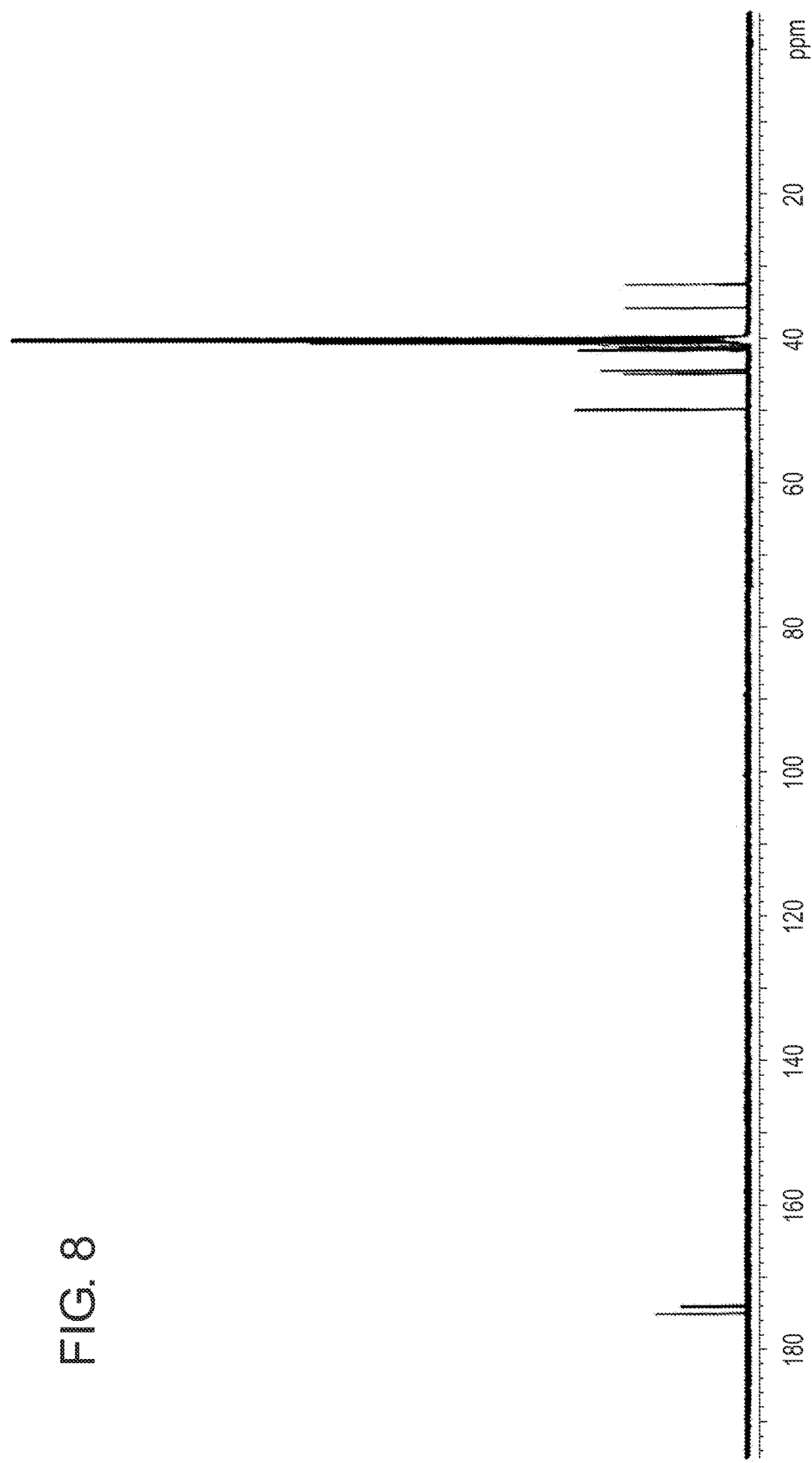
FIG. 8 is a graph showing $^{13}$C-NMR of the product obtained in Example 2.

(23)

and the yield was calculated to be 88%. Note that the above BNBDA can include a stereoisomer A composed of a compound having an endo/exo type three-dimensional structure represented by the following general formula (24) and its enantiomeric compound having an exo/endo type three-dimensional structure (hereinafter sometimes referred to as "BNBDA-A." Note that endo/exo type and exo/endo type enantiomers cannot be distinguished spectroscopically, and thus are evaluated as the "stereoisomer A" together in the following description), and a stereoisomer B having an endo/endo type three-dimensional structure represented by the following general formula (25) (hereinafter sometimes referred to as "BNBDA-B"), and, as a result of the above structural identification (IR measurement, NMR measurement), the product obtained as described above was identified to be BNBDA containing BNBDA-B having an endo/endo type three-dimensional structure as a stereoisomer at a rate of 100% by mole. Note that, as a result of IR measurement and NMR measurement of such a product, FIG. 6 shows a graph of an IR spectrum, FIG. 7 shows a graph of $^1$H-NMR, and FIG. 8 shows a graph of $^{13}$C-NMR.

[Chem. 22]

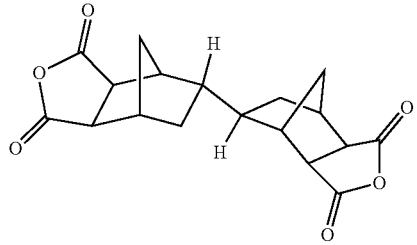

(24)

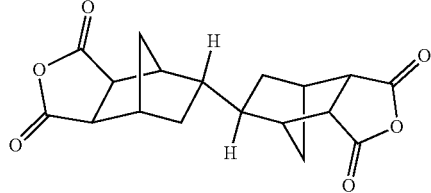

(25)

Comparative Example 2

The BNBTE (25.2 g, 59.7 mmol, brown oily product) with a BNBTE-A/BNBTE-B mole ratio ([BNBTE-A]/[BNBTE-B]) of 71/29 obtained in Comparative Example 1 was dissolved into acetic acid (348 g) to prepare a solution, and the solution was added to a 1-L two-necked flask with a reflux tube. Then, the solution was added with trifluoromethanesulfonic acid (CF$_3$SO$_3$H, 15.0 g, 2.98 mmol) as an acid catalyst (homogeneous acid catalyst) and further with acetic anhydride (24.4 g) to obtain a mixture liquid.

Next, after the atmospheric gas in the flask was replaced with nitrogen, the mixture liquid was heated while being stirred with a magnetic stirrer under a nitrogen stream and under a condition of atmospheric pressure. Refluxing was carried out for 6.5 hours at a temperature of 118° C. inside the flask (refluxing step). After that, the heating was stopped for gradual cooling to room temperature (25° C.), and recrystallization was performed. The resultant crystals were filtered and washed once with acetic acid (80 mL), and then the crystals were heated and dried at 80° C. under vacuum. In this way, 4.86 g of gray powder was obtained as a crude product (crude yield of 25%).

Figure 9:
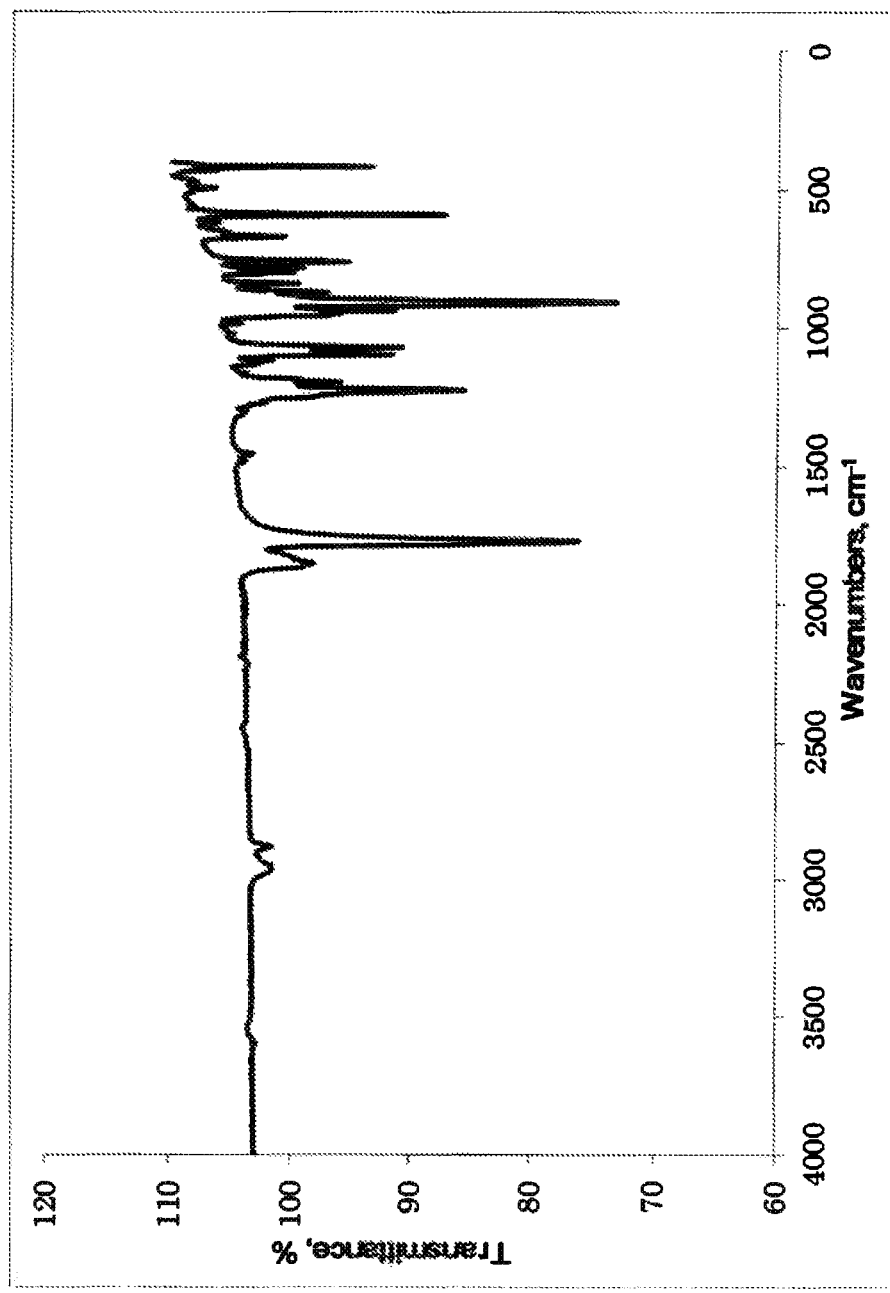
FIG. 9 is a graph showing an IR spectrum of a product obtained in Comparative Example 2.
Figure 10:
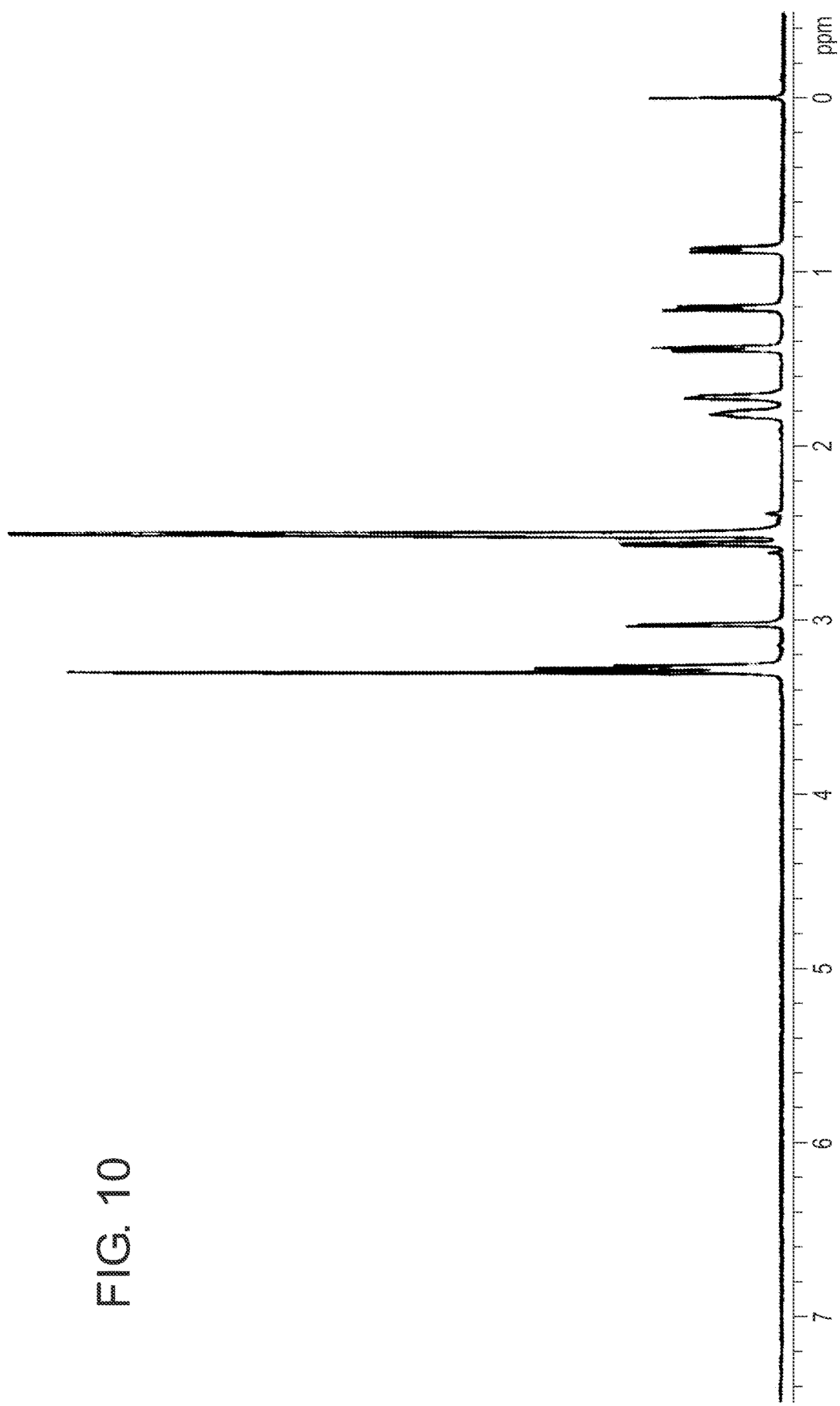
FIG. 10 is a graph showing $^1$H-NMR of the product obtained in Comparative Example 2.
Figure 11:
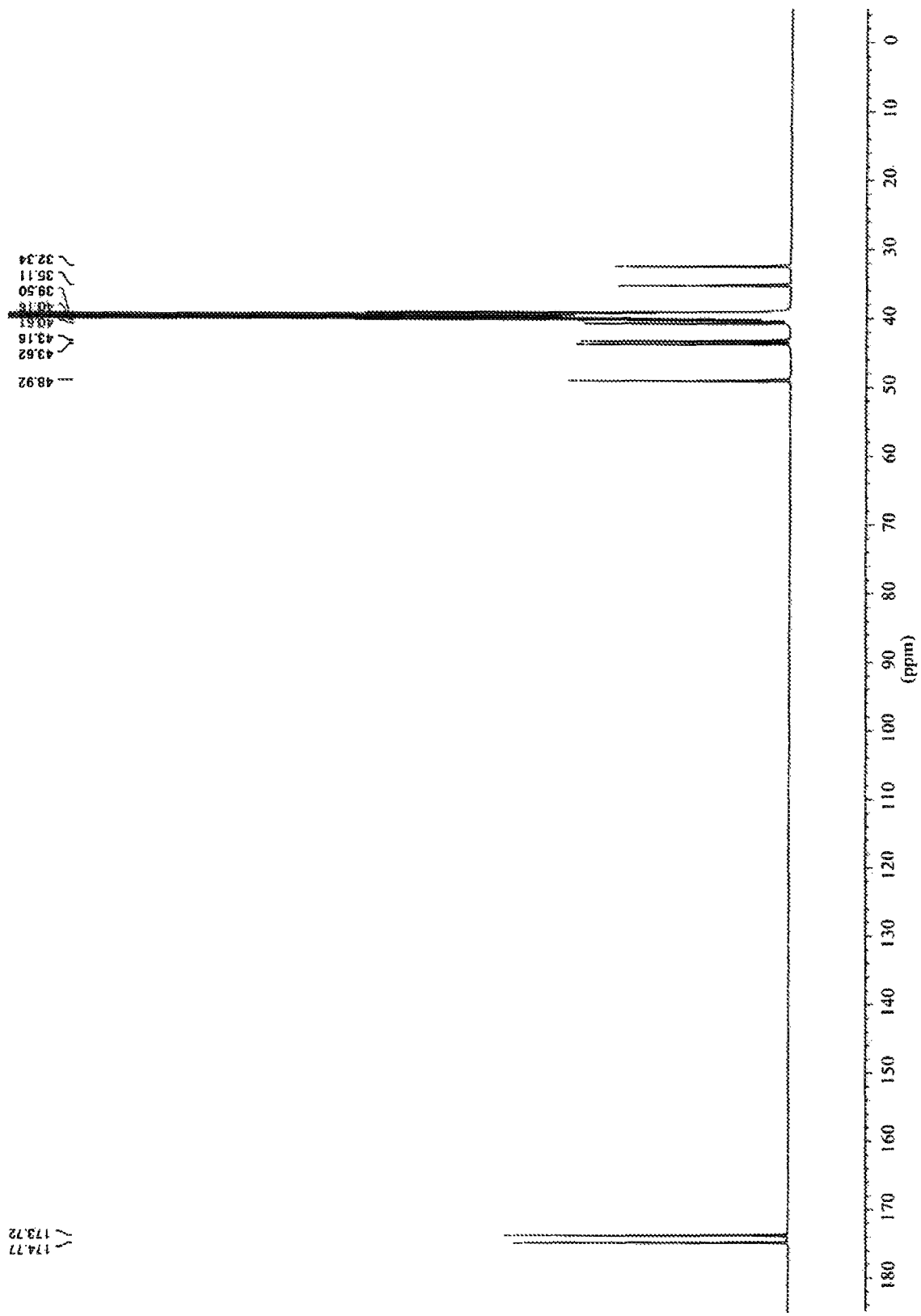
FIG. 11 is a graph showing $^{13}$C-NMR of the product obtained in Comparative Example 2.

Sublimation purification was conducted by the following method on 0.996 g of the crude product thus obtained. Specifically, the crude product was placed and set in a Kugelrohr distillation apparatus (GTO-2000 manufactured by Shibata Scientific Technology Ltd.). Subsequently, the pressure in the apparatus was reduced to 1.2 Torr at room temperature (25° C.), and the temperature was finally raised to 315° C. while gradually raising the temperature stepwise to 200° C. and 250° C. After the temperature was raised and reached 315° C. in this way, heating was continued for one and a half hours, and the temperature was returned to room temperature. Sublimation purification was conducted as described above to obtain a product (0.911 g, sublimation purification yield of 92%, total yield of 23%). Note that, when IR measurement and NMR measurement ($^1$H-NMR, $^{13}$C-NMR) were carried out to identify the structure of the obtained product, it was found that the obtained product was BNBDA having a BNBDA-A content of 100% by mole. Note that, as a result of IR measurement and NMR measurement of such a product, FIG. 9 shows a graph of an IR spectrum, FIG. 10 shows a graph of $^1$H-NMR, and FIG. 11 shows a graph of $^{13}$C-NMR.

Note that, although it is not exactly clear why the product finally obtained by using BNBTE with a BNBTE-A/BNBTE-B mole ratio ([BNBTE-A]/[BNBTE-B]) of 71/29 as a raw material was BNBDA having a BNBDA-A content of 100% by mole, the present inventors speculate the reason as follows. The step of gradually cooling from the reaction temperature (118° C.) to room temperature to perform recrystallization after the refluxing step for obtaining the crude product corresponds to the so-called crystallization step. Here, since the concentration of the solution was low (the concentration was about 6.5 wt %), only part of the components in the dissolved matter (the mixture of BNBDA-A and BNBDA-B) was precipitated. As a result, BNBDA-A being the raw material and the main component was precipitated more, whereas BNBDA-B having a low concentration also in the raw material was precipitated only at an undetectable level, or BNBDA-B was not precipitated. Note that the present inventors speculate that, regarding BNBDA-B in particular, the concentration in the solution was lower than the saturation concentration, so that precipitation did not occur.

<3> Synthesis of Polyimide

Example 3

<Step of Preparing Polyamic Acid>

First, under a nitrogen atmosphere, 6.16 g (15.0 mmol) of 2,2-bis[4-(4-aminophenoxy)phenyl]propane (BAPP: manufactured by Seika Corporation) was introduced as an aromatic diamine into a 20 mL screw cap vial, and also 4.96 g (15.0 mmol) of BNBDA having a BNBDA-B content of 100% by mole obtained in Example 2 was introduced into the screw cap vial. Subsequently, 44.4 g of N-methyl-2-pyrrolidone (N,N-dimethylacetamide) was added into the screw cap vial to obtain a mixture liquid. Next, the obtained mixture liquid was stirred under a nitrogen atmosphere at room temperature (25° C.) for 3.5 hours to produce a polyamic acid, thereby obtaining a reaction liquid containing the polyamic acid (solution of polyamic acid). Note that a measurement sample (solution) was prepared by partially using the thus obtained reaction liquid [a solution of the polyamic acid (solvent: N-methyl-2-pyrrolidone)], removing the solvent to isolate the polyamic acid, and then dissolving the polyamic acid in N,N-dimethylacetamide so that the concentration of the polyamic acid was 0.5 g/dL. The intrinsic viscosity [η] of the polyamic acid was measured as described above, and the result showed that the intrinsic viscosity [η] was 0.54 dL/g.

<Step of Preparing Polyimide (Thermal Imidization Step)>

The reaction liquid obtained in the step of preparing a polyamic acid (solution of polyamic acid) was spin-coated onto a large scale glass slide (manufactured by Matsunami Glass Ind., Ltd. under the trade name of "S9213," length: 76 mm, width 52 mm, and thickness 1.3 mm), thereby forming a coating film on the glass plate. After that, the glass plate having the coating film formed was introduced into an oven and was allowed to stand for 4 hours under a temperature condition of 60° C. under a nitrogen atmosphere. Thereafter, the temperature condition was changed to 300° C. (final heating temperature) and the glass plate was allowed to stand for 1 hour to cure the coating film. Thereby, polyimide-coated glass coated with a thin film made of polyimide (film made of polyimide) on the glass substrate was obtained.

Next, the thus obtained polyimide-coated glass was taken out of the oven and was immersed in hot water of 90° C. for 0.5 hours, and the film was collected by being peeled off of the glass substrate. Thereby, a film made of polyimide having a film thickness of 6 μm was obtained. Note that regarding the obtained film made of polyimide, when the color was checked visually, the color was observed to be transparent.

An IR spectrum of the thus obtained film was measured, and a C═O stretching vibration of imidocarbonyl was observed at 1705 cm$^{-1}$ and 1775 cm$^{-1}$, indicating that the obtained film was made of a polyimide. Note that, from the types of monomers used, it is apparent that the obtained polyimide is a polyimide containing a repeating unit (B) having an endo/endo type three-dimensional structure represented by the general formula (6) at a rate of 100% by mole.

Example 4

First, 0.743 g (2.25 mmol) of BNBDA having a BNBDA-B content of 100% by mole obtained in Example 2 (BNBDA-B content: 100% by mole) and 0.743 g (2.25 mmol) of BNBDA ester having a BNBDA-A content of 100% by mole obtained in Comparative Example 2 (BNBDA-A content: 100% by mole) were mixed to obtain BNBDA with a BNBDA-A/BNBDA-B mole ratio ([BNBDA-A]/[BNBDA-B]) of 50/50.

Subsequently, a polyimide was prepared after preparing a polyamic acid in the same manner as that of Example 3 except that BNBDA in which the mole ratio of BNBDA-A and BNBDA-B obtained as described above ([BNBDA-A]/[BNBDA-B]) was 50/50 was used instead of using BNBDA having a BNBDA-B content of 100% by mole obtained in Example 2. In this way, a film made of a polyimide having a thickness of 11 μm was obtained. Note that the intrinsic viscosity [η] of the polyamic acid thus obtained was measured, and the result showed that the intrinsic viscosity [η] was 0.52 dL/g.

In addition, an IR spectrum of the thus obtained film made of a polyimide was measured, and a C═O stretching vibration of imidocarbonyl was observed at 1705 cm$^{-1}$ and 1775 cm$^{-1}$, indicating that the obtained film was made of a polyimide. Note that, from the types of monomers used, it is apparent that the obtained polyimide is a polyimide containing a repeating unit (A) composed of a structural unit having an endo/exo type three-dimensional structure represented by the general formula (5) and its enantiomeric structural unit having an exo/endo type three-dimensional structure, and a repeating unit (B) having an endo/endo type three-dimensional structure represented by the general formula (6) at a rate of 50:50 in a mole ratio [repeating unit (A):repeating unit (B)].

Comparative Example 3

A polyimide was prepared after preparing a polyamic acid in the same manner as that of Example 3 except that BNBDA having a BNBDA-A content of 100% by mole obtained in Comparative Example 2 was used instead of using BNBDA having a BNBDA-B content of 100% by mole obtained in Example 2. In this way, a film made of a polyimide having a thickness of 30 μm was obtained. Note that the intrinsic viscosity [η] of the polyamic acid thus obtained was measured, and the result showed that the intrinsic viscosity [η] was 0.54 dL/g.

In addition, an IR spectrum of the thus obtained film made of a polyimide was measured, and a C=O stretching vibration of imidocarbonyl was observed at 1705 cm$^{-1}$ and 1777 cm$^{-1}$, indicating that the obtained film was made of a polyimide. Note that, from the types of monomers used, it is apparent that the obtained polyimide is a polyimide containing a repeating unit (A) composed of a structural unit having an endo/exo type three-dimensional structure represented by the general formula (5) and its enantiomeric structural unit having an exo/endo type three-dimensional structure at a rate of 100% by mole.

[Evaluation of Characteristics of Polyimides Obtained in Examples 3 and 4 and Comparative Example 3]

<Measurement of Total Luminous Transmittance, Haze (Turbidity), and Yellowness Index (YI)>

The values of total luminous transmittance (unit: %), haze (turbidity: HAZE), and yellowness index (YI) were obtained by carrying out measurement by use of the polyimides (polyimides in the shape of a film) obtained in Examples and the like as samples for measurement as it is, and by use of a measuring apparatus for the total luminous transmittance and the haze manufactured by NIPPON DENSHOKU INDUSTRIES CO., LTD. under the trade name of "Haze Meter NDH-5000" and a measuring apparatus for the yellowness index manufactured by NIPPON DENSHOKU INDUSTRIES CO., LTD. under the trade name of "Spectrophotometer SD6000." Note that the total luminous transmittance was obtained by performing measurement in accordance with JIS K7361-1 (issued in 1997), the haze (turbidity) is obtained by performing measurement in accordance with JIS K7136 (issued in 2000), and the chromaticity (YI) is obtained by performing measurement in accordance with ASTM E313-05 (issued in 2005). Table 1 shows the obtained results.

<Measurement of 5% Weight-Loss Temperature>

The 5% weight-loss temperature of each of the polyimides obtained in Examples and the like were obtained as follows. The polyimide film produced in each Example was used, and the temperature was raised from room temperature to 40° C. in a nitrogen gas stream. The polyimide film was heated under a condition of 10° C./min with a starting temperature of 40° C. to measure the temperature at which the weight of the sample used was reduced by 5% using a thermogravimetric analyzer ("TG/DTA220" manufactured by SII NanoTechnology Inc.). Table 1 shows the obtained results.

<Elongation at Break (%)>

The elongation at break of each of the polyimides obtained in Examples and the like was measured under a condition of a tensile rate of 5 mm/min in accordance with the method described in the Japanese Industrial Standards "JIS K7161." A tensile tester manufactured by Instron was used as a measuring apparatus. A puncher in accordance with JIS K-7139A22 was used to process the polyimide obtained in each of Examples and the like into a dumbbell-shaped test piece, and then the test piece was set in the apparatus for measurement. Table 1 shows the obtained results.

TABLE 1

|  | Example 3 | Example 4 | Comparative Example 3 |
| --- | --- | --- | --- |
| Type of Acid Dianhydride | BNBDA-B (100% by Mole) | Mixture of BNBDA-A and BNBDA-B (Mole Ratio 50:50) | BNBDA-A (100% by Mole) |
| Type of Aromatic Diamine | BAPP | BAPP | BAPP |
| Type of Solvent Used in Production | NMP | NMP | NMP |
| Calcination Temperature During Polyimide Production (° C.) | 300 | 300 | 300 |
| Intrinsic Viscosity of Polyamic Acid (dL/g) | 0.54 | 0.52 | 0.54 |
| Film Thickness of Polyimide Film (μm) | 6 | 11 | 30 |
| 5% Weight-Loss Temperature (TG-DTA, Unit: ° C.) | 484.3 | 485.6 | 490.8 |
| Total Luminous Transmittance (%) | 90 | 88 | 90 |
| HAZE (%) | 0.3 | 0.4 | 0.3 |
| YI | 0.86 | 1.51 | 1.20 |
| Elongation at Break (%) | 23.3 | 10.7 | 9.6 |

As is apparent from the results shown in Table 1, it was found that each of the polyimides obtained in Examples 3 and 4 and Comparative Example 3 had sufficiently excellent transparency based on the values of total luminous transmittance, haze (turbidity), and yellowness index (YI). In addition, it was found that each of the polyimides obtained in Examples 3 and 4 and Comparative Example 3 had a 5% weight-loss temperature of 484° C. or higher and also a sufficiently high heat resistance based on the 5% weight-loss temperature. As described above, it was confirmed that each of the polyimides obtained in Examples 3 and 4 and Comparative Example 3 had a sufficient light transmittance and a heat resistance at a higher level. On the other hand, it was confirmed that both of the polyimides obtained in Examples 3 and 4 had an elongation at break at a higher level than the polyimide obtained in Comparative Example 3. From such results, it was found that the polyimides of the present invention (Examples 3 and 4) had a heat resistance at a sufficiently high level while having a sufficient light transmittance. In addition, it was confirmed that the polyimides of the present invention (Examples 3 and 4) had a mechanical strength at a higher level based on the elongation at break.

Example 5

A polyimide was prepared after preparing a polyamic acid in the same manner as that of Example 3 except that the amount used of BNBDA having a BNBDA-B content of 100% by mole obtained in Example 2 (BNBDA-B content: 100% by mole) was changed from 0.743 g (2.25 mmol) to 5.95 g (18.0 mmol), 3.61 g (18.0 mmol) of 4,4'-diaminodiphenyl ether (4,4'-DDE: manufactured by Tokyo Chemical Industry Co., Ltd.) was used instead of using 6.16 g (15.0 mmol) of 2,2-bis[4-(4-aminophenoxy)phenyl]propane (BAPP) as an aromatic diamine, 38.2 g of N,N-dimethylacetamide (DMAc) was used instead of using 44.4 g of N-methyl-2-pyrrolidone (NMP), and the final heating temperature during polyimide preparation was changed from 300° C. to 350° C. In this way, a film (film thickness: 9 μm) made of a polyimide was obtained. Note that the intrinsic viscosity [η] of the polyamic acid thus obtained was measured, and the result showed that the intrinsic viscosity [η] was 0.51 dL/g. In addition, an IR spectrum of the thus obtained film made of a polyimide was measured, and a C=O stretching vibration of imidocarbonyl was observed at 1701 cm$^{-1}$ and 1775 cm$^{-1}$, indicating that the obtained film was made of a polyimide. Note that, from the types of monomers used, it is apparent that the obtained polyimide is a polyimide containing a repeating unit (B) having an endo/endo type three-dimensional structure represented by the general formula (6) at a rate of 100% by mole.

The characteristics of the polyimide thus obtained (Example 5) (total luminous transmittance (%), haze (turbidity: %), yellowness index (YI), 5% weight-loss temperature (° C.), and elongation at break (%)) were measured in the same manner as the polyimide or the like obtained in Example 3. As a result, the characteristics of the polyimide obtained in Example 5 were found such that total luminous transmittance: 89%, haze: 0.5%, YI: 1.33, 5% weight-loss temperature: 488.4° C., and elongation at break: 15.1%. Also from these results, it was found that the polyimide of the present invention (Example 5) had a heat resistance at a sufficiently high level while having a sufficient light transmittance.

INDUSTRIAL APPLICABILITY

As described above, the present invention makes it possible to provide a tetracarboxylic dianhydride which is usable as a raw material monomer for producing a polyimide having a sufficient light transmittance and a heat resistance at a higher level, a carbonyl compound which can be used for efficiently producing the tetracarboxylic dianhydride, a polyimide which can have a sufficient light transmittance and a heat resistance at a higher level, and a polyimide precursor resin which can be preferably utilized for producing the polyimide. Therefore, the polyimide of the present invention is particularly useful as a material or the like for producing a polyimide product for use in the various applications described above (such as films for flexible wiring boards).

The invention claimed is:
1. A tetracarboxylic dianhydride comprising
at least one acid dianhydride (A) selected from the group consisting of compounds each having an endo/exo type three-dimensional structure represented by the following general formula (1):

[Chem. 1]

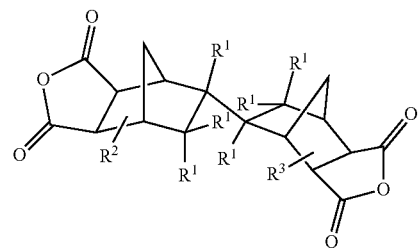

(1)

[in the formula (1), $R^1$s each independently represent one selected from the group consisting of a hydrogen atom, alkyl groups having 1 to 10 carbon atoms, a hydroxy group, and a nitro group, or two $R^1$s connected to a common carbon atom may together form a methylidene group, and
$R^2$ and $R^3$ each independently represent one selected from the group consisting of a hydrogen atom and alkyl groups having 1 to 10 carbon atoms] and their enantiomeric compounds each having an exo/endo type three-dimensional structure, and/or
an acid dianhydride (B) having an endo/endo type three-dimensional structure represented by the following general formula (2):

[Chem. 2]

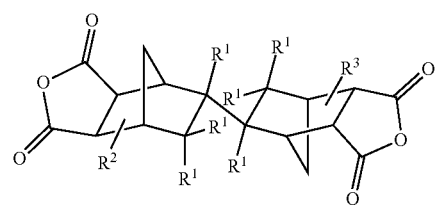

(2)

[in the formula (2), $R^1$s, $R^2$, and $R^3$ have the same meanings as those of $R^1$s, $R^2$, and $R^3$ in the above formula (1), respectively], wherein
a content of the acid dianhydride (B) in a total amount of the acid dianhydrides (A) and (B) is 30 to 100% by mole in a mole ratio.

* * * * *